US011390872B2

(12) United States Patent
Reilly et al.

(10) Patent No.: US 11,390,872 B2
(45) Date of Patent: *Jul. 19, 2022

(54) METHODS AND COMPOSITIONS FOR SECRETION OF HETEROLOGOUS POLYPEPTIDES

(71) Applicant: Genentech, Inc., South San Francisco, CA (US)

(72) Inventors: Dorothea Reilly, South San Francisco, CA (US); Yizhou Zhou, South San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 127 days.

This patent is subject to a terminal disclaimer.

(21) Appl. No.: 16/548,599

(22) Filed: Aug. 22, 2019

(65) Prior Publication Data

US 2020/0181625 A1 Jun. 11, 2020

Related U.S. Application Data

(63) Continuation of application No. 15/125,548, filed as application No. PCT/US2015/020783 on Mar. 16, 2015, now Pat. No. 10,435,694.

(60) Provisional application No. 62/108,476, filed on Jan. 27, 2015, provisional application No. 62/107,981, filed on Jan. 26, 2015, provisional application No. 61/953,629, filed on Mar. 14, 2014.

(51) Int. Cl.
*C12N 15/62* (2006.01)
*C07K 16/00* (2006.01)
*C12N 15/63* (2006.01)
*C12N 15/70* (2006.01)
*C12P 21/02* (2006.01)

(52) U.S. Cl.
CPC ............ *C12N 15/625* (2013.01); *C07K 16/00* (2013.01); *C07K 2317/10* (2013.01); *C07K 2317/14* (2013.01); *C07K 2317/31* (2013.01); *C07K 2319/02* (2013.01); *C12N 15/62* (2013.01); *C12N 15/63* (2013.01); *C12N 15/70* (2013.01); *C12N 2800/00* (2013.01); *C12P 21/02* (2013.01)

(58) Field of Classification Search
CPC .......................... C12N 15/625; C07K 2319/02
See application file for complete search history.

(56) References Cited

U.S. PATENT DOCUMENTS

| | | | |
|---|---|---|---|
| 5,747,662 A | 5/1998 | Simmons | |
| 5,849,576 A | 12/1998 | Skerra | |
| 6,242,177 B1 | 6/2001 | Simmons | |
| 6,979,556 B2 | 12/2005 | Simmons | |
| 7,615,529 B2 | 11/2009 | Kong-Beltran | |
| 8,361,744 B2 * | 1/2013 | Marrichi | C07K 16/00 435/41 |
| 8,536,118 B2 | 9/2013 | Wickramasinghe | |
| 8,735,098 B2 * | 5/2014 | Marrichi | C07K 16/30 435/70.21 |
| 10,227,416 B2 * | 3/2019 | Marrichi | C07K 16/00 |
| 10,435,694 B2 * | 10/2019 | Reilly | C07K 16/00 |
| 2003/0073164 A1 | 4/2003 | Simmons | |
| 2005/0227324 A1 | 10/2005 | Huang | |
| 2005/0271654 A1 | 12/2005 | Rinderknecht | |
| 2006/0270594 A1 | 11/2006 | Kong-Beltran | |
| 2007/0015244 A1 | 1/2007 | Simmons | |
| 2007/0128111 A1 | 6/2007 | Reilly | |
| 2009/0226443 A1 | 9/2009 | Filvaroff | |
| 2010/0028337 A1 | 2/2010 | Kong-Beltran | |
| 2010/0144546 A1 | 6/2010 | Delisa | |
| 2011/0111408 A1 * | 5/2011 | Marrichi | C07K 16/00 435/6.15 |
| 2012/0058906 A1 | 3/2012 | Smider | |
| 2012/0089541 A1 | 4/2012 | Patel | |
| 2012/0289688 A1 | 11/2012 | Blais | |
| 2013/0004481 A1 | 1/2013 | Solca | |
| 2013/0078252 A1 | 3/2013 | Wilson | |
| 2013/0096280 A1 | 4/2013 | Marrichi | |
| 2013/0129718 A1 | 5/2013 | Wong | |
| 2014/0037625 A1 | 2/2014 | Patel | |
| 2014/0371429 A1 | 12/2014 | Marrichi | |
| 2015/0050275 A1 | 2/2015 | Wong | |
| 2015/0056207 A1 | 2/2015 | Filvaroff | |
| 2015/0057186 A1 | 2/2015 | Steiner | |
| 2015/0064191 A1 | 3/2015 | Demeule | |
| 2015/0125452 A1 | 5/2015 | Wilson | |
| 2017/0029825 A1 | 2/2017 | Reilly | |

(Continued)

FOREIGN PATENT DOCUMENTS

| | | |
|---|---|---|
| CA | 2614512 C | 1/2014 |
| CN | 1154736 C | 4/1998 |
| CN | 1549821 A | 11/2004 |

(Continued)

OTHER PUBLICATIONS

Andersen, D.C. et al. (2004, e-pub. Aug. 25, 2004). "Production Technologies for Monoclonal Antibodies and Their Fragments," Curr. Op. Biotechnol. 15:456-462.

(Continued)

*Primary Examiner* — Hong Sang

(74) *Attorney, Agent, or Firm* — Morrison & Foerster LLP

(57) ABSTRACT

The present invention relates generally to the fields of molecular biology and protein technology. More specifically, the invention concerns signal sequences for the secretion of heterologous polypeptide from bacteria. The invention also concerns re-combinant polypeptides and uses thereof.

16 Claims, 7 Drawing Sheets

Specification includes a Sequence Listing.

(56) References Cited

U.S. PATENT DOCUMENTS

2020/0148783 A1 5/2020 Marrichi et al.

FOREIGN PATENT DOCUMENTS

| CN | 1922210 A | 2/2007 |
|---|---|---|
| CN | 101213299 A | 7/2008 |
| CN | 102933600 A | 2/2013 |
| EP | 1908769 A1 | 4/2008 |
| EP | 1356052 B1 | 8/2008 |
| JP | 3375970 B2 | 2/2003 |
| JP | 2004530419 A | 10/2004 |
| JP | 2005517385 A | 6/2005 |
| JP | 2007508032 A | 4/2007 |
| JP | 2008504007 A | 2/2008 |
| JP | 2009500027 A | 1/2009 |
| JP | 2010517532 A | 5/2010 |
| JP | 2013509867 A | 3/2013 |
| KR | 100570422 B1 | 4/2005 |
| RU | 2287574 C2 | 11/2006 |
| RU | 2012123010 A | 12/2013 |
| WO | WO199627016 A1 | 9/1996 |
| WO | WO200206190 A2 | 1/2002 |
| WO | WO200206190 A3 | 6/2002 |
| WO | WO200248376 A2 | 6/2002 |
| WO | WO2003018771 A2 | 3/2003 |
| WO | WO200248376 A3 | 6/2003 |
| WO | WO2003018771 A3 | 3/2004 |
| WO | WO2005038031 A1 | 4/2005 |
| WO | WO2005063816 A2 | 7/2005 |
| WO | WO2005063816 A3 | 8/2005 |
| WO | WO2006042158 A2 | 4/2006 |
| WO | WO2006042158 A3 | 6/2006 |
| WO | WO2007006665 A1 | 1/2007 |
| WO | WO2008094986 A2 | 8/2008 |
| WO | WO2008094986 A3 | 8/2008 |
| WO | WO2008094986 A8 | 8/2008 |
| WO | WO2009021548 A1 | 2/2009 |
| WO | WO2010057097 A1 | 5/2010 |
| WO | WO2011057120 A1 | 5/2011 |

OTHER PUBLICATIONS

Auclair, S.M. et al. (2012, e-pub. Oct. 26, 2011). "Signal Peptidase I: Cleaving the Way to Mature Proteins," Protein Sci. 21(1):13-25.

Bowers, C.W. et al. (Oct. 2003). "Secretion of LamB-LacZ by the Signal Recognition Particle Pathway of *Escherichia coli*," Journal of Bateriology 185(19):5697-5705.

Doud, S.K. et al. (1993). "Titration of Protein Transport Activity by Incremental Changes in Signal Peptide Hydrophobicity," Biochemistry 32(5):1251-1256.

Eisenberg, E.S. et al. (Oct. 15, 1984). "Analysis of Membrane and Surface Protein Sequences With the Hydrophobic Moment Plot," J. Mol. Biol. 179(1):125-142.

Final Office Action, dated Sep. 24, 2018, for U.S. Appl. No. 15/125,548, filed Sep. 12, 2016, 15 pages.

Gion, W.R. et. al. "Expression of Antibodies Using Single Open Reading Frame (sORF) Vector Design: Demonstration of Manufacturing Feasibility," mAbs 5(4):595-607, (2013).

Hikita, C. et al. (Mar. 5, 1992). "Effects of Total Hydrophobicity and Length of the Hydrophobic Domain of a Signal Peptide on in Vitro Translocation Efficiency," The Journal of Biological Chemistry 267(7):4882-4888.

Houdebine, L-M. et al. (1994). "Minireview. Production of Pharmaceutical Proteins from Transgenic Animals," Journal of Biotechnology 34:269-287.

Huber, D. et al. (May 2005). "Use of Thioredoxin as a Reporter to Identify a Subset of *Escherichia coli* Signal Sequences That Promote Signal Recognition Particle-Dependent Translocation," J. Bacteriol. 187(9):2983-2991.

International Search Report dated Feb. 10, 2011, for PCT Application No. PCT/US2010/055702, filed on Nov. 5, 2010, 6 pages.

International Search Report dated Jul. 1, 2015, for PCT Application No. PCT/US2015/020783, filed on Mar. 16, 2015, 8 pages.

Izard, J.W. et al. (1994). "Signal Peptides: Exquisitely Designed Transport Promoters," Mol. Microbiol. 13(5):765-773.

Izard, J.W. et al. (Aug. 30, 1996). "The Amino-Terminal Charge and Core Region Hydrophobicity Interdependently Contribute to the Function of Signal Sequences," The Journal of Biological Chemistry 271(35):21579-21582.

Jackson, R.W. et al. (Nov. 1965). "Effects of Toluene on *Escherichia coli*," Journal of Bacteriology 90(5):1420-1425.

Jonet, M.A. et al., (2012, e-pub. Mar. 23, 2012). "Optimization of a Heterologous Signal Peptide by Site-Directed Mutagenesis for Improved Secretion of Recombinant Proteins in *Escherichia coli*," J. Mol. Microbio. Biotechnol. 22:48-52.

Josefsson, L.-G. et al. (Jul. 1981). "Different Exported Proteins in *E. coli* Show Differences in the Temporal Mode of Processing in Vivo," Cell 25(1):151-157.

Kadokura, H. et al. (Sep. 18, 2009). "Detecting Folding Intermediates of a Protein as It Passes Through the Bacterial Translocation Channel," Cell 138:1164-1173, 20 pages.

Kappell, J.H. et al. (1992)."Regulating Gene Expression in Transgenic Animals," Current Opinions in Biotechnology, 3:548-553.

Karamyshev, A.L. et al. (1998). "Processing of *Escherichia coli* Alkaline Phosphatase: Role of the Primary Structure of the Signal Peptide Cleavage Region," J. Mol. Biol. 277:859-870.

Kendall, D.A. et al. (Jun. 12, 1986). "Idealization of the Hydrophobic Segment of the Alkaline Phosphatase Signal Peptide," Nature 312:706-708.

Kendall, D.A. et al. (May 25, 1988). "A Functional Decaisoleucine-Containing Signal Sequence," The Journal of Biological Chemistry 263(15):7261-7265.

Kipriyanov, S.M. et al. (Jun. 1999). "Generation of Recombinant Antibodies," Mol. Biotech. 12:173-201.

Le Calvez, H. et al. (1996). "Increased Efficiency of Alkaline Phosphatase Production Levels in *Escherichia coli* Using a Degenerate PelB Signal Sequence," Gene 170:51-55.

Lee, H.C. et al. (Mar. 13, 2001, e-pub. Feb. 27, 2001). "The Targeting Pathway of *Escherichia coli* Presecretory and Integral Membrane Proteins is Specified by the Hydrophobicity of the Targeting Signal," Proc. Natl. Acad. Sci. U.S.A. 98(6):3471-3476.

Low, K.O. et al. (May 2013, e-pub. Mar. 26, 2013). "Optimisation of Signal Peptide for Recombinant Protein Secretion in Bacterial Hosts," Appl. Microbiol. Biotechnol. 97(9):3811-3826.

Marrichi, M. et al. (Dec. 12, 2008, e-pub. Sep. 25, 2008). "Genetic Toggling of Alkaline Phosphatase Folding Reveals Signal Peptides for all Major Modes of Transport Across the Inner Membrane of Bacteria," The Journal of Biological Chemistry 283(50):35223-35235.

Marrichi, M.J. et al. (Nov. 10, 2009). "Periplasmic Expression of Full-Length Antibodies and Antibody Derivatives in *Escherichia coli* via Multiple Translocation Pathways," Food, Pharmaceutical & Bioengineering Division, AIChE Annual Meeting, Nashville, TN, Abstract No. 185, 31 pages.

Martens, T. et al., (Oct. 15, 2006). "A Novel One-Armed Anti-c-Met Antibody Inhibits Glioblastoma Growth In vivo," Clin. Cancer Res. 12(20):6144-6152.

Natale, P. et al. (2008, e-pub. Aug. 9, 2007). "Sec- and Tat-Mediated Protein Secretion Across the Bacterial Cytoplasmic Membrane-Distinct Translocases and Mechanisms," Biochimica et Biophysica Acta 1778:1735-1756.

Non-Final Office Action, dated Apr. 11, 2018, for U.S. Appl. No. 15/125,548, filed Sep. 12, 2016, 27 pages.

Notice of Allowance, dated Jun. 25, 2019, for U.S. Appl. No. 15/125,548, filed Sep. 12, 2016, 11 pages.

Notice of Allowance, dated May 24, 2019, for U.S. Appl. No. 15/125,548, filed Sep. 12, 2016, 8 pages.

Oliver, D.B. et al. (Aug. 1982). "Regulation of a Membrane Component Required for Protein Secretion in *Escherichia coli*," Cell 30(1):311-319.

Overbeek, P.A. (1994). "Factors Affecting Transgenic Animal Production," in Transgenic Animal Technology, pp. 96-98.

(56) References Cited

OTHER PUBLICATIONS

Plückthun, A. et al. (Jun. 1997). "New Protein Engineering Approaches to Multivalent and Bispecific Antibody Fragments," Immunotechnology 3:83-105.
Quan, S. et al. (2013). "Isolation of Bacterial Envelope Proteins," Chapter 22 in Bacterial Cell Surfaces: Methods Molecular Biology, Delcour, A.H. (ed)., 966:359-366.
Rakestraw, J.A. et al. (Aug. 15, 2009, e-pub. Apr. 1, 2009). "Directed Evolution of a Secretory Leader for the Improved Expression of Heterologous Proteins and Full-Length Antibodies in Sacccharomyces cerevisiae," Biotechnology and Bioengineering 103(6):1192-1201.
Ravn, P. et al. (2003). "Optimization of Signal Peptide SP310 for Heterologous Protein Production in Lactococcus lactis," Microbiology 149:2193-2201.
Rusch, S.L. et al. (1994). "Signal Peptide Hydrophobicity Is Finely Tailored for Function," Journal of Cellular Biochemistry 55:209-217.
Rusch, S.L. et al. (2002, e-pub. Jul. 13, 2002). "Juxtaposition of Signal-Peptide Charge and Core Region Hydrophobicity is Critical for Functional Signal Peptides," Arch. Microbiol. 178:306-310.
Rusch, S.L. et al. (Jan. 14, 1994). "Transport of an Export-defective Protein by a Highly Hydrophobic Signal Peptide," The Journal of Biological Chemistry 269(2):1243-1248.
Sasaki, S. et al. (Mar. 15, 1990). "In Vitro Kinetic Analysis of the Role of the Postive Charge at the Amino-Terminal Region of Signal Peptides in Translocation of Secretory Protein Across in the Cytoplasmic Membrane in Esherichia coli," The Journl of Biological Chemistry 265(8):4358-4363.
Schierle, C.F. et al. (Oct. 1, 2003). "The DsbA Signal Sequence Directs Efficient, Cotranslational Export of Passenger Proteins to the *Escherichia coli* Periplasm via the Signal Recognition Particle Pathway," Journal of Bacteriology 185(19):5706-5713.
Schlatter, S. et al. "On the Optimal Ratio of Heavy to Light Chain Genes for Efficient Recombinant Antibody Production by CHO Cells," Biotechnol. Prog. 21:122-133, (Jan.-Feb. 2005). Abstract Only.
Schwall, R.H. et al. (Mar. 2004). "Inhibition of cMet activation by a one-armed antibody," Proceedings of the American Association for Cancer Research Abstract No. 1424, 45:327.
Simmons, L.C. et al. (May 1, 2002). "Expression of Full-Length Immunoglobulins in *Escherichia coli*: Rapid and Efficient Production of Aglycosylaled Antibodies," J. Immunol. Meth. 263(1-2):133-147.
Simmons, L.C. et al. (May 1996). "Translational Level is a Critical Factor for the Secretion of Heterologous Proteins in *Escherichia coli*," Nat. Biotechnol. 14(5):629-634.
Steiner, D. et al. (Jul. 2006, e-pub. Jul. 2, 2006). "Signal Sequences Directing Cotranslational Translocation Expand the Range of Proteins Amenable to Phage Display," Nature Biotechnology 24(7):823-831.
Stemmer, W.P.C. et al. (1993). "Increased Antibody Expression from *Escherichia coli* Though Wobble-Base Library Mutagenesis by Enzymatic Inverse PCR," Gene 123:1-7.
Thie, H. et al. (Jun. 2008). "SRP and Sec Pathway Leader Peptides for Antibody Phage Display and Antibody Fragment Production in *E. coli*," New Biotechnology 25(1):49-54.
Vimberg, V. et al. (Oct. 31, 2007). "Translation Initiation Region Sequence Preferences in *Escherichia coli*," BMC Molecular Biotechnology 8(100):1-13.
Wall, R.J. et al. (1996). "Trangenic Livestock: Progress and Prospects for the Future," Theriogenology 45:57-68.
Written Opinion dated Feb. 10, 2011, for PCT Application No. PCT/US2010/055702, filed on Nov. 5, 2010, 8 pages.
Written Opinion dated Jul. 1, 2015, for PCT Application No. PCT/US2015/020783, filed on Mar. 16, 2015, 8 pages.
Zhou, Y. et al. (Apr. 9, 2014). "Signal Recognition Particle and SecA Cooperate during Export of Secretory Proteins with Highly Hydrophobic Signal Sequences," Plos One pp. 1-8.
Finkelstein, A.V. et al. (2012). Protein Physics: A Course of Lectures With Colored and Stereoscopic Illustrations and Tasks: Training Book—4th Edition, p. 23. English Translation.
Overbeek, P.A. (2014). "3-Factors Affecting Transgenic Animal Production," in Transgenic Animal Technology 3rd Edition: A Laboratory Handbook pp. 71-107.
Yarlin, A.A. et al. (1999). "Basic Immunology," M.: Medicine pp. 172-174. English Translation.

\* cited by examiner

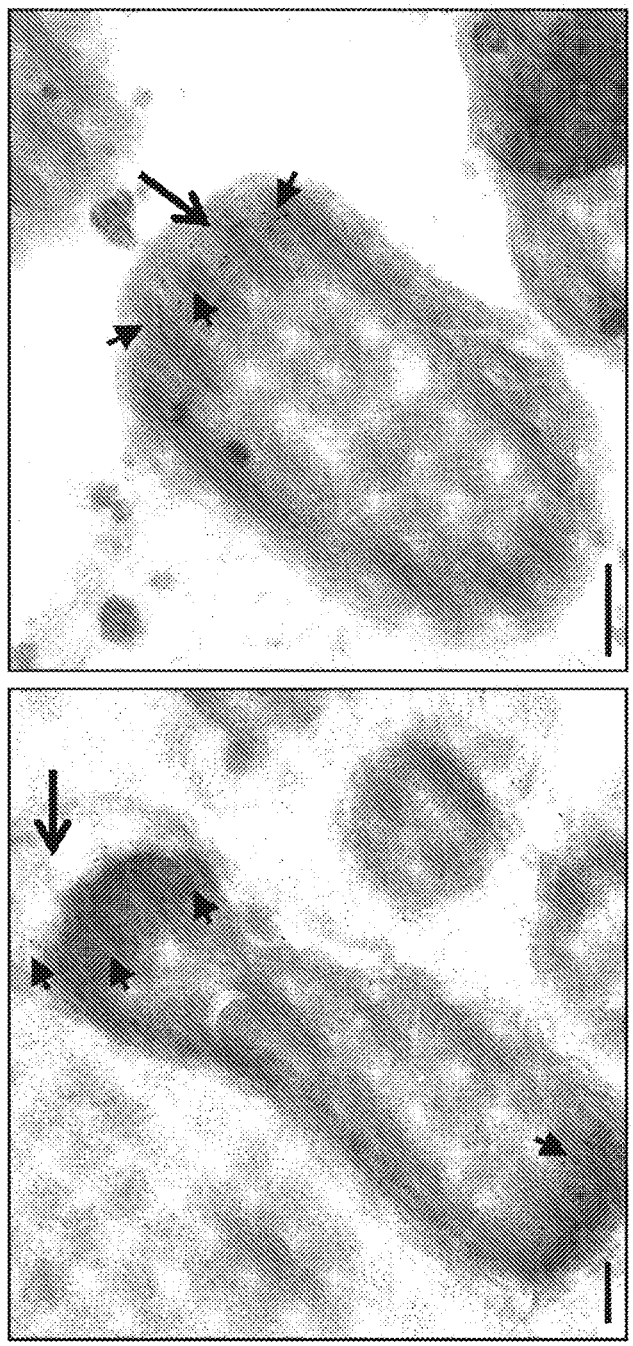

| ssHC | bDsbA1 | bDsbA1 L11I | bDsbA1 L11S | bSTII1 | bSTII1S11L Codon1 | bSTII1S11L Codon2 |

αFc

Periplasmic Extract, Reduced

*FIG. 3A*

| ssLC | mSTII1 | mSTII1 | mSTII1 | mSTII1 | mSTII1 | mSTII1 | mSTII1 | mSTII1 |
| ssHC | bSTII1 | bMalE1 | bDsbA1 | bPhoA1 | bDsbA1 L11I | bDsbA1 L11S | bSTII1 S11L | bSTII1 S11I |

αFc

Periplasmic Extracts, Reduced

*FIG. 3B*

METHODS AND COMPOSITIONS FOR SECRETION OF HETEROLOGOUS POLYPEPTIDES

CROSS REFERENCE TO RELATED APPLICATIONS

This application is a continuation of U.S. patent application Ser. No. 15/125,548, filed Sep. 12, 2016, which adopts the international filing date of Mar. 16, 2015, which is a National Phase filing under 35 U.S.C. § 371 of International Application No. PCT/US2015/020783, filed Mar. 16, 2015, which claims priority to U.S. patent application No. 61/953,629, filed on Mar. 14, 2014, and U.S. patent application No. 62/107,981, filed on Jan. 26, 2015, and U.S. patent application No. 62/108,476, filed on Jan. 27, 2015, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 1463920355001SEQLIST.TXT, date recorded: Feb. 21, 2020, size: 18 KB).

FIELD OF THE INVENTION

The present invention relates generally to the fields of molecular biology and protein technology. More specifically, the invention concerns signal peptides for the secretion of heterologous polypeptides from bacteria. The invention also concerns prokaryotically produced recombinant polypeptides and uses thereof.

BACKGROUND OF THE INVENTION

Recent ears have seen increasing promises of using heterologous polypeptide, for example, antibodies, as diagnostic and therapeutic agents for various disorders and diseases. Many research and clinical applications require large quantities of functional polypeptide, thus calling for scaled-up, yet economic systems for polypeptide production. Particularly useful is the recombinant production of antibodies using a variety of expression hosts, ranging from prokaryotes such as *E. coli* or *B. subtilis*, to yeast, plants, insect cells and mammalian cells. Kipriyanov and Little (1999) *Mol. Biotech.* 12:173-201.

Compared to other polypeptide production systems, bacteria, particularly *E. coli*, provides many unique advantages. The raw materials used (i.e. bacterial cells) are inexpensive and easy to grow, therefore reducing the cost of products. Prokaryotic hosts grow much faster than, e.g., mammalian cells, allowing quicker analysis of genetic manipulations. Shorter generation time and ease of scaling up also make bacterial fermentation a more attractive means for large quantity protein production. The genomic structure and biological activity of many bacterial species including *E. coli* have been well-studied and a wide range of suitable vectors are available, making expression of a desirable antibody more convenient. Compared with eukaryotes, fewer steps are involved in the production process, including the manipulation of recombinant genes, stable transformation of multiple copies into the host, expression induction and characterization of the products. Pluckthun and Pack (1997) *Immunotech* 3:83-105.

Various approaches have been used to make recombinant polypeptides in bacteria. Recombinant proteins can be obtained from bacteria either through refolding of inclusion bodies expressed in the cytoplasm, or through expression followed by secretion to the bacterial periplasm. The choice between secretion and refolding is generally guided by several considerations. Secretion is usually the faster and more commonly used strategy for producing antibodies. Kipriyanov and Little (1999), supra. However, *E. coli* secretion and refolding capacity is often limited to a lower level compared to other expression hosts.

Antibody expression in prokaryotic systems can be carried out in different scales. For general reviews of antibody production in *E. coli*, see Pluckthun and Pack (1997) *Immunotech* 3:83-105; Pluckthun et al. (1996) in ANTIBODY ENGINEERING: A PRACTICAL APPROACH, pp 203-252 (Oxford Press); Pluckthun (1994) in HANDBOOK OF EXP PHARMCOL VOL 3: THE PHARMCOL OF MONOCLONAL ANTIBODIES, pp 269-315 (ed. M. Rosenberg and G. P. Moore; Springer-Verlag, Berlin).

Many biological assays (such as X-ray crystallography) and clinical applications (such as protein therapy) require large amounts of protein. Accordingly, a need exists for high yield yet simple systems for producing properly assembled, soluble and functional heterologous polypeptides, such as antibodies.

All references cited herein, including patent applications and publications, are incorporated by reference in their entirety.

SUMMARY OF THE INVENTION

The invention provides a novel means for increasing production of heterologous proteins such as antibodies. The use of periplasmic secretion as a means for high-level production of heterologous proteins (e.g., antibodies) can be limited by several frequently encountered problems. First, secretion efficiency of the protein of interest may be low. Second, the precursor in many cases is incompletely processed to mature protein. Third, over-expressed heterologous proteins often fold improperly, aggregate into insoluble inclusion bodies, or are proteolyzed by *E. coli* proteases. Fourth, antibodies are complex multimeric proteins made from two different polypeptides, the heavy and light chains, which must be exported into the periplasm, folded properly and form the appropriate disulfide bonds. The complexity of this protein folding and secretion adds to the challenges of antibody manufacturing in *E. coli*. *E. coli* secretion and refolding capacity is often limited to a lower level compared to other expression hosts. While TIR optimization has been shown to be useful for generating more efficient protein secretion, other approaches not been shown to routinely improve tile secretion of heterologous proteins in *E. coli*. For example, optimization of a signal protein was shown to decrease secretion of recombinant cyclodextrin glucanotransferase (CGTase) into the periplasmic space. Janet et al., J Mol Microbiol Biotechnol (2012); 22:48-58.

In the present work, the inventors demonstrate that increasing the average hydrophobicity of the signal peptide increased secretion of soluble antibody to the *E. coli* periplasm. Variant signal peptides with increased average hydrophobicity were developed and the inventors demonstrated increased periplasmic secretion of soluble antibody when signal peptide variants with increased average hydrophobicity were used, and decreased periplasmic section of soluble antibody when signal peptide variants with decreased average hydrophobicity were used.

In one aspect, provided are methods of increasing secretion of an antibody heavy chain and/or an antibody light chain from an *E. coli* host cell, comprising culturing an *E. coli* host cell comprising polynucleotide comprising (1) a first polynucleotide encoding a first signal peptide operably linked to a polynucleotide encoding an antibody heavy chain, wherein the average hydrophobicity of the signal peptide is greater than about 0.5; and/or (2) a second polynucleotide encoding a second signal peptide operably linked to a polynucleotide encoding an antibody light chain, wherein the average hydrophobicity of the second signal peptide is greater than about 0.5, whereby upon expression of the antibody in a host cell, the heavy and light chains are folded and assembled to form a biologically active antibody.

In one aspect, provided are methods of making an antibody heavy chain and/or light chain from an *E. coli* host cell, comprising culturing an *E. coli* host cell comprising polynucleotide comprising (1) a first polynucleotide encoding a first signal peptide operably linked to a polynucleotide encoding an antibody heavy chain, wherein the average hydrophobicity of the signal peptide is greater than about 0.5; and/or (2) a second polynucleotide encoding a second signal peptide operably linked to a polynucleotide encoding an antibody light chain, wherein the average hydrophobicity of the second signal peptide is greater than about 0.5, whereby upon expression of the antibody in a host cell, the heavy and light chains are folded and assembled to form a biologically active antibody. In some embodiments, the method further comprises recovering the heterologous polypeptide from the host cell culture. In some embodiments, the heterologous polypeptide is recovered from the host cell culture medium. In some embodiments, the method further comprises combining the recovered heterologous polypeptide with a pharmaceutically acceptable carrier, excipient, or carrier to prepare a pharmaceutical formulation comprising the heterologous polypeptide.

In one aspect, provided are methods of making an antibody heavy chain and/or light chain from an *E. coli* host cell, comprising culturing an *E. coli* host cell comprising polynucleotide comprising (1) a first polynucleotide encoding a first signal peptide operably linked to a polynucleotide encoding an antibody heavy chain, wherein the average hydrophobicity of the signal peptide is greater than about 0.5; and/or (2) a second polynucleotide encoding a second signal peptide operably linked to a polynucleotide encoding an antibody light chain, wherein the average hydrophobicity of the second signal peptide is greater than about 0.5, whereby upon expression of the antibody in a host cell, the heavy and light chains are folded and assembled to form a biologically active antibody.

In one aspect, provided are methods of translocating an antibody heavy chain and/or light chain from an *E. coli* host cell, comprising culturing an *E. coli* host cell comprising polynucleotide comprising (1) a first polynucleotide encoding a first signal peptide operably linked to a polynucleotide encoding an antibody heavy chain, wherein the average hydrophobicity of the signal peptide is greater than about 0.5; and/or (2) a second polynucleotide encoding a second signal peptide operably linked to a polynucleotide encoding an antibody light chain, wherein the average hydrophobicity of the second signal peptide is greater than about 0.5, whereby upon expression of the antibody in a host cell, the heavy and light chains are folded and assembled to form a biologically active antibody.

In some embodiments, the average hydrophobicity of the first signal peptide is greater than about 0.6. In some embodiments, the average hydrophobicity of the first signal peptide is greater than about 0.7. In some embodiments, the average hydrophobicity of the second signal peptide is greater than about 0.6. In some embodiments, the average hydrophobicity of the second signal peptide is greater than about 0.7. In some embodiments, the average hydrophobicity of the first and second signal peptides is similar (e.g., about equivalent). In some embodiments, the average hydrophobicity of the first and second signal peptides is different.

In some embodiments, the first and/or second signal peptide is a variant co-translational signal peptide. In some embodiments, the first and/or second signal peptide is a variant DsbA signal peptide. In some embodiments, the variant DsbA signal peptide comprises a mutation at residue L11, wherein the variant DsbA signal peptide has a greater average hydrophobicity than a wildtype DsbA signal peptide of SEQ ID NO:3. In some embodiments, wherein the mutation is L11I or S18Y. In some embodiments, the variant DsbA signal peptide comprises sequence of SEQ ID NO:13 or 15.

In some embodiments, the signal peptide is a Sfmc signal peptide. In some embodiments, the Sfmc signal peptide has TIR strength that is different than TIR strength of wild-type Sfmc signal peptide. In some embodiments, the relative translation strength (also termed TIR strength) of the Sfmc signal peptide is about 2, about 3, about 4, about 5, about 6, about 7, or more, such as about 8, about 9, or more. In some embodiments, the relative translation strength of the Sfmc signal peptide is between 1 and 3, between 2 and 4, between 3 and 5, between 4 and 6, between 5 and 7, between 6 and 8. In some embodiments, the relative translation strength of the Sfmc signal peptide is between 2 and 5, between 3 and 7, or between 4 and 8. In some embodiments, the signal peptide is FlgI, NikA, AsmA, TolB, YraI, FecB, CemH, TreA, FocC, TraU, SfmL, or TorT. In some embodiments, the FlgI, NikA, AsmA, TolB, YraI, FecB, CemH, TreA, FocC, TraU, SfmL, or TorT signal peptide has relative translation strength that is different than relative translation strength of wild-type FlgI, NikA, AsmA, TolB, YraI, FecB, CemH, TreA, FocC, TraU, SfmL, or TorT signal peptide. In some embodiments, the TIR strength of the FlgI, NikA, AsmA, TolB, YraI, FecB, CemH, TreA, FocC, TraU, SfmL, or TorT signal peptide is about 2, about 3, about 4, about 5, about 6, about 7, or more, such as about 8, about 9, or more. In some embodiments, the relative translation strength of the FlgI, NikA, AsmA, TolB, YraI, FecB, CemH, TreA, FocC, TraU, SfmL, or TorT signal peptide is between 1 and 3, between 2 and 4, between 3 and 5, between 4 and 6, between 5 and 7, between 6 and 8. In some embodiments, the relative translation strength of the FlgI, NikA, AsmA, TolB, YraI, FecB, CemH, TreA, FocC, TraU, SfmL, or TorT signal peptide is between 2 and 5, between 3 and 7, or between 4 and 8.

In some embodiments, the signal peptide is not Sfmc. In some embodiments, the signal peptide is not TorT. In some embodiments, the signal peptide is not any one or more of FlgI, NikA, AsmA, TolB, YraI, FecB, CemH, TreA, FocC, TraU, SfmL, or TorT.

In some embodiments, the relative translation strength of the first and/or second signal peptide is about 1, about 2, about 3, about 4, about 5, about 6, about 7, or about 8. In some embodiments, the relative translation strength of the first signal peptide is about 5 and the relative translation strength of the second signal sequence is about 8. In some embodiments, the relative translation strength of the first signal peptide is about 8 and the relative translation strength of the second signal sequence is about 5. In some embodiments, the relative translation strength of the Sfmc signal peptide is between 1 and 3, between 2 and 4, between 3 and 5, between 4 and 6, between 5 and 7, between 6 and 8. In some embodiments, the relative translation strength of the Sfmc signal peptide is between 2 and 5, between 3 and 7, or between 4 and 8.

In some embodiments, wherein the polynucleotide in the host cell further comprises a promoter. In some embodiments, the promoter is a prokaryotic promoter selected from the group consisting of phoA, tac, lpp, lac-lpp, lac, ara, and T7 promoter.

In some embodiment, the E. coli host cell is of a strain deficient in endogenous protease activities. In some embodiments, the genotype of the E. coli lacks degP and prc genes and harbors a mutant spr gene. In some embodiments, the host cell further comprises a polynucleotide encoding at least one prokaryotic polypeptide selected from the group consisting of DsbA, DsbC, DsbG and FkpA. In some embodiments, the polynucleotide encodes both DsbA and DsbC.

In some embodiments, the methods further comprise recovering the antibody from the host cell culture. In some embodiments, the antibody is recovered from the host cell culture medium. In some embodiments, the methods further comprise combining the recovered antibody with a pharmaceutically acceptable carrier, excipient, or carrier to prepare a pharmaceutical formulation comprising the antibody. In some embodiments, at least 50% of the immunoglobulin polypeptide complexes that are formed are the antibody. In some embodiments, least 70% of the immunoglobulin polypeptide complexes that are formed are the antibody. In some embodiments, least 80% of the immunoglobulin polypeptide complexes that are formed are the antibody. In some embodiments, least 90% of the immunoglobulin polypeptide complexes that are formed are the antibody.

In some embodiments, the antibody is a monoclonal antibody. In some embodiments, the antibody is a chimeric antibody, an affinity matured antibody, a bispecific antibody, humanized antibody, or a human antibody. In some embodiments, the antibody is a bispecific antibody.

In another aspect, provided are variant DsbA signal peptides, wherein the variant comprises an H region with an average hydrophobicity that is greater than 0.5.

In another aspect, provided are variant DsbA signal peptides comprising a mutation at residue S11, wherein the variant has a greater average hydrophobicity than a DsbA signal peptide of SEQ ID NO:3. In some embodiments, the mutation is L11I and/or S18Y.

In another aspect, provided are variant STII signal peptides comprising a mutation at residue S11, wherein the variant STII signal peptide has a greater average hydrophobicity than a STII signal peptide of SEQ ID NO:1. In some embodiments, the mutation is S11A, S11I or S11L.

In another aspect, provided are variant signal peptides consisting of, consisting essentially of or comprising a sequence of SEQ ID NO:8, 11, 13, 15, 31, or 33.

In another aspect, provided is any of the variant signal peptides disclosed herein fused to a heterologous protein. In some embodiments, the heterologous polypeptide is an antibody heavy chain. In some embodiments, the heterologous polypeptide is an antibody light chain. In some embodiments, the heterologous polypeptide is an antibody light and heavy chain. In some embodiments, the heterologous polypeptide is a multimeric polypeptide. In some embodiments, the heterologous polypeptide is an immunoadhesin.

In another aspect, provided are polynucleotide sequences that encode any of the variant signal peptides disclosed herein.

In another aspect, provided are polynucleotide sequences that encode any of the variant signal peptides disclosed herein, operably linked to a polynucleotide encoding a heterologous polypeptide, whereby upon expression of the heterologous polypeptide in a host cell the heterologous polypeptide is folded and assembled to form a biologically active heterologous polypeptide.

In some embodiments, the host cell is a prokaryotic host cell. In some embodiments, the host cell is E. coli.

In another aspect, provided are polynucleotides encoding an antibody, said polynucleotides comprising (1) a polynucleotide encoding a first signal peptide operably linked to a polynucleotide encoding an antibody heavy chain and (2) a polynucleotide encoding a second signal peptide operably inked to a polynucleotide encoding an antibody light chain, whereby upon expression of the antibody in a host cell the heavy and light chains are folded and assembled to form a biologically active antibody, wherein the first signal peptide is a variant signal peptide of any one of variant signal peptide disclosed herein. In some embodiments, the first signal peptide consists of, consists essentially of, or comprises a sequence of SEQ ID NO:8, 11, 13, 15, 31, 33, or 42. In some embodiments, the first signal peptide is a variant DsbA signal peptide, wherein the variant comprises an H region with an average hydrophobicity that is greater than 0.5. In some embodiments, the first signal peptide is a variant DsbA signal peptide comprising a mutation at residue S11, wherein the variant has a greater average hydrophobicity than a DsbA signal peptide of SEQ ID NO:3. In some embodiments, the mutation is L11I and/or S18Y. In some embodiments, the first signal peptide is a variant STII signal peptide comprising a mutation at residue S11, wherein the variant STII signal peptide has a greater average hydrophobicity than a STII signal peptide of SEQ NO:1. In some embodiments, the mutation is S11A, S11I or S11L.

In some embodiments, the second signal peptide is a signal peptide. In some embodiments, the second signal peptide consists of, consists essentially of, or comprises a sequence of SEQ ID NO:8, 11, 13, 15, 31, 33, or 42. In some embodiments, the second signal peptide is a variant DsbA signal peptide, wherein the variant comprises an H region with an average hydrophobicity that is greater than 0.5. In some embodiments, the second signal peptide is a variant DsbA signal peptide comprising a mutation at residue S11, wherein the variant has a greater average hydrophobicity than a DsbA signal peptide of SEQ ID NO:3. In some embodiments, the mutation is L11I and/or S18Y. In some embodiments, the second signal peptide is a variant STII signal peptide comprising a mutation at residue S11, wherein the variant STII signal peptide has a greater average hydrophobicity than a STII signal peptide of SEQ ID NO:1. In some embodiments, the mutation is S11A, S11I or S11L.

In some embodiments, the polynucleotide encoding an antibody further comprises (3) a polypeptide encoding a third signal peptide operably linked to a polynucleotide encoding an Fc polypeptide. The third signal peptide may be, for example, any of the variant signal peptides disclosed herein. In some embodiments, the third signal peptide consists of, consists essentially of, or comprises a sequence of SEQ ID NO:8, 11, 13, 15, 31, 33, or 42.

In some embodiments, the polynucleotide further comprises a promoter operably linked to the heterologous polypeptide. In some embodiments, the promoter is a prokaryotic promoter selected from the group consisting of phoA, tac, lpp, lac-lpp, lac, ara, trp, and T7 promoter. In some embodiments, the promoter is a phoA promoter.

In some embodiment, the polynucleotide comprises (a) a first promoter, wherein the first promoter is operably linked to a light chain and (b) a second promoter, wherein the second promoter is operably linked to a heavy chain. In some embodiments, the first and second promoters are both phoA promoters.

In some embodiments, the polynucleotide further comprises (c) a third promoter, wherein the third promoter is operably linked to an Fc polypeptide. In some embodiments, the promoter is a phoA promoter.

In some embodiments, wherein the heterologous polypeptide is a protease, an immunoadhesin, an extracellular domain of a receptor, a heteromultimeric protein, or an antibody.

In some embodiments, the antibody is a monoclonal antibody. In some embodiments, the antibody is a chimeric antibody, a bispecific antibody, humanized antibody, an antibody fragment or a human antibody. In some embodiments, the antibody is a bispecific antibody.

A vector comprising a polynucleotide of any of the polynucleotides disclosed herein. In some embodiments, the vector is an expression vector.

A composition comprising any of the polynucleotides disclosed herein.

A host cell comprising any of the polynucleotides disclosed herein. In some embodiments, the host cell is a prokaryotic cell. In some embodiments, the prokaryotic cell is E. coli. In some embodiments, the E. coli is of a strain deficient in endogenous protease activities. In some embodiments, the genotype of the E. coli lacks degP and prc genes and harbors a mutant spr gene. In some embodiments, the host cell further comprises a polynucleotide encoding a prokaryotic chaperone protein. In some embodiments, the prokaryotic chaperone protein is DsbA and/or DsbC. In some embodiments, host cell overexpresses a prokaryotic chaperone protein.

In another aspect, provided are methods of making an a heterologous polypeptide, said method comprising culturing any of the host cells described herein so that the nucleic acid is expressed, whereby upon expression of said polynucleotide in a host cell, the heterologous polypeptide is folded to form a biologically active heterologous polypeptide. In some embodiments, the method further comprises recovering the heterologous polypeptide from the host cell culture. In some embodiments, the heterologous polypeptide is recovered from the host cell culture medium. In some embodiments, the method further comprises combining the recovered heterologous polypeptide with a pharmaceutically acceptable carrier, excipient, or carrier to prepare a pharmaceutical formulation comprising the heterologous polypeptide.

In another aspect, provided are methods of secreting a heterologous polypeptide from a cell, said method comprising culturing any of the host cells provided herein so that the nucleic acid is expressed and the heterologous polypeptide is secreted.

In another aspect, provided are methods of translocating a heterologous polypeptide from a cell, said method comprising culturing any of the host cells provided herein so that the nucleic acid is expressed and the heterologous polypeptide is translocated.

A heterologous polypeptide obtained by any of the methods provided herein. In some embodiments, the polypeptide is an antibody.

In some embodiments, use of the variant signal peptide results in, e.g., increased production of heterologous polypeptide (e.g., antibody, e.g., heavy chain and/or light chain), increased secretion of heterologous polypeptide (e.g., antibody), increased production of mature heterologous polypeptide (e.g., antibody), increased secretion of mature heterologous polypeptide (e.g., antibody), increased production of soluble heterologous polypeptide (e.g., antibody), increased secretion of soluble heterologous polypeptide (e.g., antibody), increased localization of inclusion bodies on the periplasmic side, and/or increased production of a heterologous polypeptide whereby the heterologous polypeptide is secreted, folded and assembled into a biologically active polypeptide (e.g., antibody), e.g., as compared to use of wildtype (non-variant) signal peptide. In some embodiments, the relative translation strength (also termed TIR strength) of the variant signal peptide and wildtype (non-variant) signal peptide is about 1. In some embodiments, the relative translation strength of the variant signal peptide and wildtype (non-variant) signal peptide is about 2, about 3, about 4, about 5, about 6, about 7 or more such about 8 or more. In some embodiments the relative translation strength of the variant signal peptide and wildtype (non-variant) signal peptide is about 4. In some embodiments the relative translation strength of the variant signal peptide and wildtype (non-variant) signal peptide is about 5. In some embodiments the relative translation strength of the variant signal peptide and wildtype (non-variant) signal peptide is about 6. In some embodiments the relative translation strength of the variant signal peptide and wildtype (non-variant signal peptide is about 8. In some embodiments, the relative translation strength of the first and second signal peptides is about equal. In some embodiments, the relative translation strengths of the first and second signal peptides are different.

In one aspect, provided is a polynucleotide sequence that encodes a variant signal peptide of the invention. In some embodiments, the variants are of a PhoA, MalE, DsbA or STII signal peptide. In some embodiments, the polynucleotide sequence encodes an amino acid of SEQ ID NO:8, 11, 12, 13, 14, 15, 31, 32, 33, 34, or 35. In some embodiments, the polynucleotide sequence encodes an amino acid sequence of SEQ ID NO: 8, 11, or 13. In some embodiments, the polynucleotide sequence encodes an amino acid sequence of SEQ ID NO: 14. In some embodiments, the polynucleotide sequence encodes an amino acid sequence of SEQ ID NO: 12 or 15. In some embodiments, the polynucleotide encodes an amino acid sequence of SEQ ID NO: 31 or 33. In some embodiments, the polynucleotide encodes an amino acid sequence of SEQ ID NO: 32, 34, or 35. In some embodiments, the polynucleotide consists of, consists essentially of, or comprises a polynucleotide sequence of SEQ ID NO:23, 24, 25, 26, 27, 28, 29 30, 36, 37, 38, 39 or 40. In some embodiments, the polynucleotide consists of, consists essentially of, or comprises a polynucleotide sequence of SEQ ID NO:23, 24, 25, 26, or 28. In some embodiments, the polynucleotide consists of, consists essentially of, or comprises a polynucleotide sequence of SEQ ID NO:29. In some embodiments, the polynucleotide consists of, consists essentially of, or comprises a polynucleotide sequence of one of SEQ ID NO:27 or 30. In some embodiments, the polynucleotide consists of, consists essentially of, or comprises a polynucleotide sequence of SEQ ID NO: 36 or 38. In some embodiments, the polynucleotide consists of, consists essentially of, or comprises a polynucleotide sequence of SEQ ID NO: 37, 39 or 40.

In another aspect, the invention provides a polynucleotide comprising a polynucleotide encoding a variant signal peptide of the invention operably linked to a polynucleotide encoding a heterologous polypeptide, whereby upon expression of the heterologous polypeptide in a host cell (e.g., a prokaryotic host cell, e.g., an *E. coli* host cell), the heterologous polypeptide is folded and assembled to form a biologically active heterologous polypeptide. Examples of heterologous polypeptides are further disclosed herein. In some embodiments, the heterologous polypeptide is an antibody heavy chain. In some embodiments, the heterologous polypeptide is an antibody light chain. In some embodiments, the heterologous polypeptide is an Fc polypeptide. In some embodiments, the heterologous polypeptide is a multimeric polypeptide. In some embodiments, the heterologous polypeptide is a heteromultimer. In some embodiments, signal peptide is any one of the variant signal peptides disclosed here. In some embodiments, the signal peptide consists of, consists essentially of, or comprises an amino acid sequence of SEQ ID NO:8, 11, 12, 13, 14, 15, 31, 32, 33, 34, or 35. In some embodiments, the signal peptide consists of, consists essentially of, or comprises an amino acid sequence of SEQ ID NO: 8, 11, or 13. In some embodiments, the signal peptide consists of, consists essentially of, or comprises an amino acid sequence of SEQ ID NO: 14. In some embodiments, the signal peptide consists of, consists essentially of, or comprises an amino acid sequence of SEQ NO: 12 or 15. In some embodiments, the signal peptide consists of, consists essentially or, or comprises an amino acid sequence of SEQ ID NO: 31 or 33. In some embodiments, the signal peptide consists of, consists essentially or, or comprises amino acid sequence of SEQ ID NO: 32, 34, or 35. In some embodiments, the polynucleotide encoding a variant signal peptide consists of, consists essentially of, or comprises sequence of SEQ ID NO:23, 24, 25, 26, 27, 28, 29 30, 31, 32, 33, 34, 35, 36, 37, 38, 39, 40, 44, 45, or 46. In some embodiments, the polynucleotide encoding a variant signal peptide consists of, consists essentially of, or comprises sequence of SEQ ID NO:23, 26, 28, 30, 36, 37, 38, 45 or 46. In some embodiments, the polynucleotide encoding a variant signal peptide consists of, consists essentially of, or comprises sequence of SEQ ID NO:29. In some embodiments, the polynucleotide encoding a variant signal peptide consists of, consists essentially of, or comprises sequence of SEQ NO:27 or 30. In some embodiments, the polynucleotide encoding a variant signal peptide consists of, consists essentially of, or comprises a polynucleotide sequence of SEQ ID NO: 36 or 38. In some embodiments, the polynucleotide encoding a variant signal peptide consists of, consists essentially of, or comprises a polynucleotide sequence of SEQ ID NO: 37, 39 or 40. In some embodiments, the polynucleotide encoding a variant signal peptide consists of, consists essentially of, or comprises a polynucleotide sequence of SEQ ID NO: 45 or 46.

In another aspect, the invention provides a polynucleotide comprising (1) a polynucleotide encoding a first signal peptide operably linked to a polynucleotide encoding a first heterologous polypeptide and (2) a polynucleotide encoding a second signal peptide operably linked to a polynucleotide encoding an second heterologous, whereby upon expression of the antibody in a host cell, the first and second heterologous polypeptides are folded and assembled to form a biologically active polypeptide complex.

In another aspect, the invention provides a polynucleotide encoding an antibody, said polynucleotide comprising (1) a polynucleotide encoding a first signal peptide operably linked to a polynucleotide encoding an antibody heavy chain and (2) a polynucleotide encoding a second signal peptide operably linked to a polynucleotide encoding an antibody light chain, whereby upon expression of the antibody in a host cell (e.g., a prokaryotic host cell, e.g., an *E. coli* host cell), the heavy and light chains are folded and assembled to form a biologically active antibody.

In some embodiments, the first signal peptide is a signal peptide (e.g., any signal peptide known in the art). In some embodiments, the signal peptide is a co-translational signal peptide. In some embodiments, the first signal peptide is a DsbA signal peptide. In some embodiments, the first signal peptide is a STII signal peptide. In some embodiments, the first signal peptide is any one of the variant signal peptides disclosed here. In some embodiments, the first signal peptide consists of, consists essentially of, or comprises an amino acid sequence of SEQ ID NO:8, 11, 12, 13, 14, 15, 31, 32, 33, 34, or 35. In some embodiments, the first signal peptide consists of, consists essentially of, or comprises an amino acid sequence of SEQ ID NO: 8, 11, or 13. In some embodiments, the first signal peptide consists of, consists essentially of, or comprises an amino acid sequence of SEQ ID NO: 14. In some embodiments, the first signal peptide consists of, consists essentially of, or comprises an amino acid sequence of SEQ ID NO: 12 or 15. In some embodiments, the first signal peptide consists of, consists essentially of, or comprises an amino acid sequence of SEQ ID NO: 31 or 33. In some embodiments, the first signal peptide consists of, consists essentially of, or comprises an amino acid sequence of SEQ ID NO: 32, 34, or 35. In some embodiments, the polynucleotide encoding a first signal peptide consists of, consists essentially of, or comprises sequence of SEQ ID NO:23, 24, 25, 26, 27, 28, 29 30, 31, 32, 33, 34, or 35. In some embodiments, the polynucleotide encoding a first signal peptide consists of, consists essentially of, or comprises sequence of SEQ ID NO:23, 24, 25, 26, 28, 36, 37, 38, 39 or 40. In some embodiments, the polynucleotide encoding a first signal peptide consists of, consists essentially of, or comprises sequence of SEQ ID NO:29. In some embodiments, the polynucleotide encoding a first signal peptide consists of, consists essentially of, or comprises sequence of SEQ ID NO:27 or 30. In some embodiments, the polynucleotide encoding a first signal peptide consists of, consists essentially of, or comprises sequence of SEQ ID NO: 36 or 38. In some embodiments, the polynucleotide encoding a first signal peptide consists of, consists essentially of, or comprises sequence of SEQ ID NO: 37, 39 or 40.

In some embodiments, the second signal peptide is a signal peptide (e.g., any signal peptide known in the art). In some embodiments, the second signal peptide is a DsbA signal peptide. In some embodiments, the second signal peptide is a STII signal peptide. In some embodiments, the second signal peptide is any one of the variant signal peptides disclosed here. In some embodiments, the second signal peptide consists of, consists essentially of, or comprises an amino acid sequence of SEQ ID NO:8, 11, 12, 13, 14, 15, 31, 32, 33, 34, or 35. In some embodiments, the second signal peptide consists of, consists essentially of, or comprises an amino acid sequence of SEQ ID NO: 8, 11, or 13. In some embodiments, the second signal peptide consists of, consists essentially of, or comprises an amino acid sequence of SEQ ID NO: 14. In some embodiments, the second signal peptide consists of, consists essentially of, or comprises an amino acid sequence of SEQ ID NO: 12 or 15. In some embodiments, the second signal peptide consists of, consists essentially of, or comprises an amino acid sequence of SEQ ID NO: 31 or 33. In some embodiments, the second signal peptide consists of, consists essentially of, or comprises an amino acid sequence of SEQ ID NO: 32, 35, or 35. In some embodiments, the polynucleotide encoding a second signal peptide consists of, consists essentially of, or comprises sequence of SEQ ID NO:23, 24, 25, 26, 27, 28, 29 30, 36, 37, 38, 39 or 40. In some embodiments, the polynucleotide encoding a second signal peptide consists of, consists essentially of, or comprises sequence of SEQ ID NO:23, 24, 25, 26, or 28. In some embodiments, the polynucleotide encoding a second signal peptide consists of, consists essentially of, or comprises sequence of SEQ NO:29. In some embodiments, the polynucleotide encoding a second signal peptide consists of, consists essentially of, or comprises sequence of SEQ ID NO:27 or 30. In some embodiments, the polynucleotide encoding a second signal peptide consists of, consists essentially of, or comprises sequence of SEQ ID NO:36 or 38. In some embodiments, the polynucleotide encoding a second signal peptide consists of, consists essentially of, or comprises sequence of SEQ ID NO:37, 39 or 40.

In some embodiments, the first signal peptide consists of, consists essentially of or comprises a signal peptide (e.g., any signal peptide known in the art), and the second signal peptide consists of, consists essentially of, or comprises a signal peptide disclosed herein, e.g., a signal peptide of any one of SEQ ID NO: 8, 11, 12, 13, 14, 15, 31, 32, 33, 34, and 35 (in some embodiments, any one of SEQ ID NO: 8, 11, and 13, and in some embodiments, any one of SEQ ID NO: 36 and 38). In some embodiments, the second signal peptide consists of, consists essentially of, or comprises an amino acid sequence of SEQ ID NO:8, 11, 12, 13, 14, 15, 31, 32, 33, 34, or 35. In some embodiments, the second signal peptide consists of, consists essentially of, or comprises an amino acid sequence of SEQ ID NO: 8, 11, or 13. In some embodiments, the second signal peptide consists of, consists essentially of, or comprises an amino acid sequence of SEQ ID NO: 14. In some embodiments, the second signal peptide consists of, consists essentially of, or comprises an amino acid sequence of SEQ ID NO: 12 or 15. In some embodiments, the second signal peptide consists of, consists essentially of, or comprises an amino acid sequence of SEQ ID NO:36 or 38. In some embodiments, the second signal peptide consists of, consists essentially of, or comprises an amino acid sequence of SEQ ID NO:37, 39 or 40. In some embodiments, the polynucleotide encoding a second signal peptide consists of, consists essentially of, or comprises sequence of SEQ ID NO:23, 24, 25, 26, 27, 28, 29 30, 36, 37, 38, 39 or 40. In some embodiments, the polynucleotide encoding a second signal peptide consists of, consists essentially of, or comprises sequence of SEQ ID NO:23, 24, 25, 26, or 28. In some embodiments, the polynucleotide encoding a second signal peptide consists of, consists essentially of, or comprises sequence of SEQ ID NO:29. In some embodiments, the polynucleotide encoding a second signal peptide consists of, consists essentially of, or comprises sequence of SEQ ID NO:27 or 30. In some embodiments, the polynucleotide encoding a second signal peptide consists of, consists essentially of, or comprises sequence of SEQ ID NO: 36 or 38. In some embodiments, the polynucleotide encoding a second signal peptide consists of, consists essentially of, or comprises sequence of SEQ ID NO:37, 39 or 40.

In some embodiments, the second signal peptide consists of, consists essentially of or comprises a signal peptide (e.g., any signal peptide known in the art), and the first signal peptide consists of, consists essentially of, or comprises a signal peptide disclosed herein, e.g., a signal peptide comprising, consisting of, or consisting essentially of an amino acid sequence of any one of SEQ ID NO: 8, 11, 12, 13, 14, 15, 31, 32, 33, 34, and 35 (in some embodiments, any one of SEQ ID NO: 8, 11, and 13, and in some embodiments, any one of SEQ ID NO: 31 and 33). In some embodiments, the first signal peptide consists of, consists essentially of, or comprises an amino acid sequence of SEQ ID NO:8, 11, 12, 13, 14, 15, 31, 32, 33, 35 or 35. In some embodiments, the first signal peptide consists of, consists essentially of, or comprises an amino acid sequence of SEQ ID NO: 8, 11, or 13. In some embodiments, the first signal peptide consists of, consists essentially of, or comprises an amino acid sequence of SEQ ID NO: 14. In some embodiments, the first signal peptide consists of, consists essentially of, or comprises an amino acid sequence of SEQ ID NO: 12 or 15. In some embodiments, the first signal peptide consists of, consists essentially of, or comprises an amino acid sequence of SEQ ID NO: 31 or 33. In some embodiments, the first signal peptide consists of, consists essentially of, or comprises an amino acid sequence of SEQ ID NO: 33, 34 or 35. In some embodiments, the polynucleotide encoding a first signal peptide consists of, consists essentially of, or comprises sequence of SEQ ID NO:23, 24, 25, 26, 27, 28, 29.30, 36, 37, 38 39 or 40. In some embodiments, the polynucleotide encoding a first signal peptide consists of, consists essentially of, or comprises sequence of SEQ ID NO:23, 24, 25, 26, 28, 36, 37, 38, 39 or 40. In some embodiments, the polynucleotide encoding a first signal peptide consists of, consists essentially of, or comprises sequence of SEQ ID NO:29. In some embodiments, the polynucleotide encoding a first signal peptide consists of, consists essentially of, or comprises sequence of SEQ ID NO:27 or 30. In some embodiments, the polynucleotide encoding a first signal peptide consists of, consists essentially of, or comprises sequence of SEQ ID NO: 36 or 38. In some embodiments, the polynucleotide encoding a first signal peptide consists of, consists essentially of, or comprises sequence of SEQ ID NO:37, 39 or 40.

In some embodiments, the polynucleotide encoding an antibody further comprises (3) a polypeptide encoding a third signal peptide operably linked to a polynucleotide encoding a Fc polypeptide. In some embodiments, the third signal peptide consists of, consists essentially of, or comprises a signal peptide disclosed herein, e.g., a signal peptide comprising, consisting of, or consisting essentially of an amino acid sequence of any one of 8, 11, 12, 13, 14, 15, 31, 32, 33, 34, and 35 (in some embodiments, any one of SEQ ID NO: 8, 11, and 13, and in some embodiments, any one of SEQ ID NO: 31 and 33). In some embodiments, the first signal peptide consists of, consists essentially of, or comprises an amino acid sequence of SEQ ID NO: 8, 11, or 13. In some embodiments, the first signal peptide consists of, consists essentially of, or comprises an amino acid sequence of SEQ ID NO: 14. In some embodiments, the third signal peptide consists of, consists essentially of, or comprises an amino acid sequence of SEQ ID NO: 12 or 15. In some embodiments, the third signal peptide consists of, consists essentially of, or comprises an amino acid sequence of SEQ ID NO: 31 or 33. In some embodiments, the polynucleotide encoding a third signal peptide consists of, consists essentially of, or comprises sequence of SEQ ID NO:23, 24, 25, 26, 27, 28, 29, 30, 36, 37, 38 39 or 40. In some embodiments, the polynucleotide encoding a third signal peptide consists of, consists essentially of, or comprises sequence of SEQ ID NO:23, 24, 25, 26, 28, 36, 37, 38, 39 or 40. In some embodiments, the polynucleotide encoding a third signal peptide consists of, consists essentially of, or comprises sequence of SEQ ID NO:29. In some embodiments, the polynucleotide encoding a third signal peptide consists of, consists essentially of, or comprises sequence of SEQ ID NO:27 and 30. In some embodiments, the polynucleotide encoding a third signal peptide consists of, consists essentially of, or comprises sequence of SEQ ID NO:36 or 38. In some embodiments, the polynucleotide encoding a third signal peptide consists of, consists essentially of, or comprises sequence of SEQ ID NO:37, 39 or 40. In some embodiments, the third signal peptide is a signal peptide (e.g., any signal peptide known in the art).

In some embodiments, e.g., of the polynucleotide encoding an antibody that further comprises (3) a polynucleotide encoding a third signal peptide, the first signal peptide comprises a signal peptide (e.g., any signal peptide known in the art) and the second signal peptide comprises a signal peptide (e.g., any signal peptide known in the art). In some embodiments, the first signal peptide consists of, consists essentially of, or comprises a signal peptide and the second signal peptide consists of, consists essentially of, or comprises a signal peptide disclosed herein, e.g., a signal peptide of any one of SEQ ID NO: 8, 11, 12, 13, 14, 15, 36, 37, 38, 39 and 40 (in some embodiments, any one of SEQ ID NO: 8, 11, and 13, and in some embodiments, any one of SEQ ID NO: 31 and 33). In some embodiments, the second signal peptide consists of, consists essentially of, or comprises a signal peptide and the first signal peptide consists of, consists essentially of, or comprises a signal peptide disclosed herein, e.g., a signal peptide of any one of SEQ ID NO: 8, 11, 12, 13, 14, 15, 36, 37, 38, 39 and 40 (in some embodiments, any one of SEQ ID NO: 8, 11, and 13, and in some embodiments, any one of SEQ ID NO: 31 and 33). In some embodiments, e.g., of the polynucleotide encoding an antibody that further comprises (3) a polynucleotide encoding a third signal peptide, the first signal peptide consists of, consists essentially of, or comprises a signal peptide disclosed herein, e.g., a signal peptide of any one of SEQ ID NO: 8, 11, 12, 13, 14, 15, 36, 3, 38, 39 and 40 (in some embodiments, any one of SEQ ID NO: 8, 11, and 13, and in some embodiments, any one of SEQ ID NO: 31 and 33) and the second signal peptide consists of, consists essentially of, or comprises a signal peptide disclosed herein, e.g., a signal peptide of arty one of 8, 11, 12, 13, 14, 15, 36, 37, 38, 39 and 40 (in some embodiments, any one of SEQ ID NO: 8, 11, and 13, and in some embodiments, any one of SEQ ID NO: 31 and 33).

In some embodiments, use of the variant signal peptide results in, e.g., increased production of heterologous polypeptide (e.g., antibody), increased secretion of heterologous polypeptide (e.g., antibody), increased production of mature heterologous polypeptide (e.g., antibody), increased secretion of mature heterologous polypeptide (e.g., antibody), increased production of soluble heterologous polypeptide (e.g., antibody), increased secretion of soluble heterologous polypeptide (e.g., antibody), increased production of a heterologous polypeptide whereby the heterologous polypeptide is secreted, folded and assembled into a biologically active polypeptide (e.g., antibody), e.g., as compared to use of wildtype (non-variant) signal peptide. In some embodiments, use of the variant signal peptide results in, e.g., increased production of heterologous polypeptide (e.g., antibody), increased secretion of heterologous polypeptide (e.g., antibody), increased production of mature heterologous polypeptide (e.g., antibody), increased secretion of mature heterologous polypeptide (e.g., antibody), increased production of soluble heterologous polypeptide (e.g., antibody), increased secretion of soluble heterologous polypeptide (e.g., antibody), increase production of a heterologous polypeptide whereby the heterologous polypeptide is secreted, folded and assembled into a biologically active polypeptide (e.g., antibody), e.g., as compared to use of wildtype (non-variant) signal peptide, wherein the relative translation strength of the variant signal peptide and wildtype (non-variant) signal peptide are approximately equivalent. In some embodiments, the relative translation strength of the variant signal peptide and wildtype (non-variant) signal peptide is about 1. In some embodiments, the relative translation strength of the variant signal peptide and wildtype (non-variant) signal peptide is about 2, about 3, about 4, about 5, about 6, about 7 or more such about 8 or more. In some embodiments the relative translation strength of the variant signal peptide and wildtype (non-variant) signal peptide is about 4. In some embodiments the relative translation strength of the variant signal peptide and wildtype (non-variant) signal peptide is about 5. In some embodiments the relative translation strength of the variant signal peptide and wildtype (non-variant) signal peptide is about 6. In some embodiments the relative translation strength of the variant signal peptide and wildtype (non-variant) signal peptide is about 8. In some embodiments, the relative translation strength of the first and second signal peptides are approximately equal. In some embodiments, the relative translation strengths of the first and second signal peptides are different.

In one aspect, the invention provides uses of a heterologous polypeptide generated using the methods of the invention, in the preparation of a medicament for the therapeutic and/or prophylactic treatment of a disease, such as a cancer, a tumor, a cell proliferative disorder, and/or an immune (such as autoimmune) disorder. The heterologous polypeptide can be of any form described herein, including antibody, antibody fragment, polypeptide (e.g., an oligopeptide), or combination thereof.

In one aspect, the invention provides use of a signal peptide disclosed herein or polynucleotide encoding a signal peptide disclosed herein in the preparation of a medicament for the therapeutic and/or prophylactic treatment of a disease, such as a cancer, a tumor, a cell proliferative disorder and/or an immune (such as autoimmune) disorder.

In one aspect, the invention provides use of an expression vector disclosed herein in the preparation of a medicament for the therapeutic and/or prophylactic treatment of a disease, such as a cancer, a tumor, a cell proliferative disorder and/or an immune (such as autoimmune) disorder.

In one aspect, the invention provides use of a host cell disclosed herein in the preparation of a medicament fix the therapeutic and/or prophylactic treatment of a disease, such as a cancer, a tumor, a cell proliferative disorder and/or an immune (such as autoimmune) disorder.

In one aspect, the invention provides use of an article of manufacture disclosed herein in the preparation of a medicament for the therapeutic and/or prophylactic treatment of a disease, such as a cancer, a tumor, a cell proliferative disorder, an immune (such as autoimmune) disorder and/or an angiogenesis-related disorder (wound healing).

In one aspect, the invention provides use of a kit disclosed herein in the preparation of a medicament for the therapeutic and/or prophylactic treatment of a disease, such as a cancer, a tumor, a cell proliferative disorder and/or an immune (such as autoimmune) disorder).

BRIEF DESCRIPTION OF THE DRAWINGS

FIGS. 1A, 1B, and 1C: depict effects of signal peptide variants on 5D5 full-length antibody and heavy chain levels.

Figures 1A, 1C:
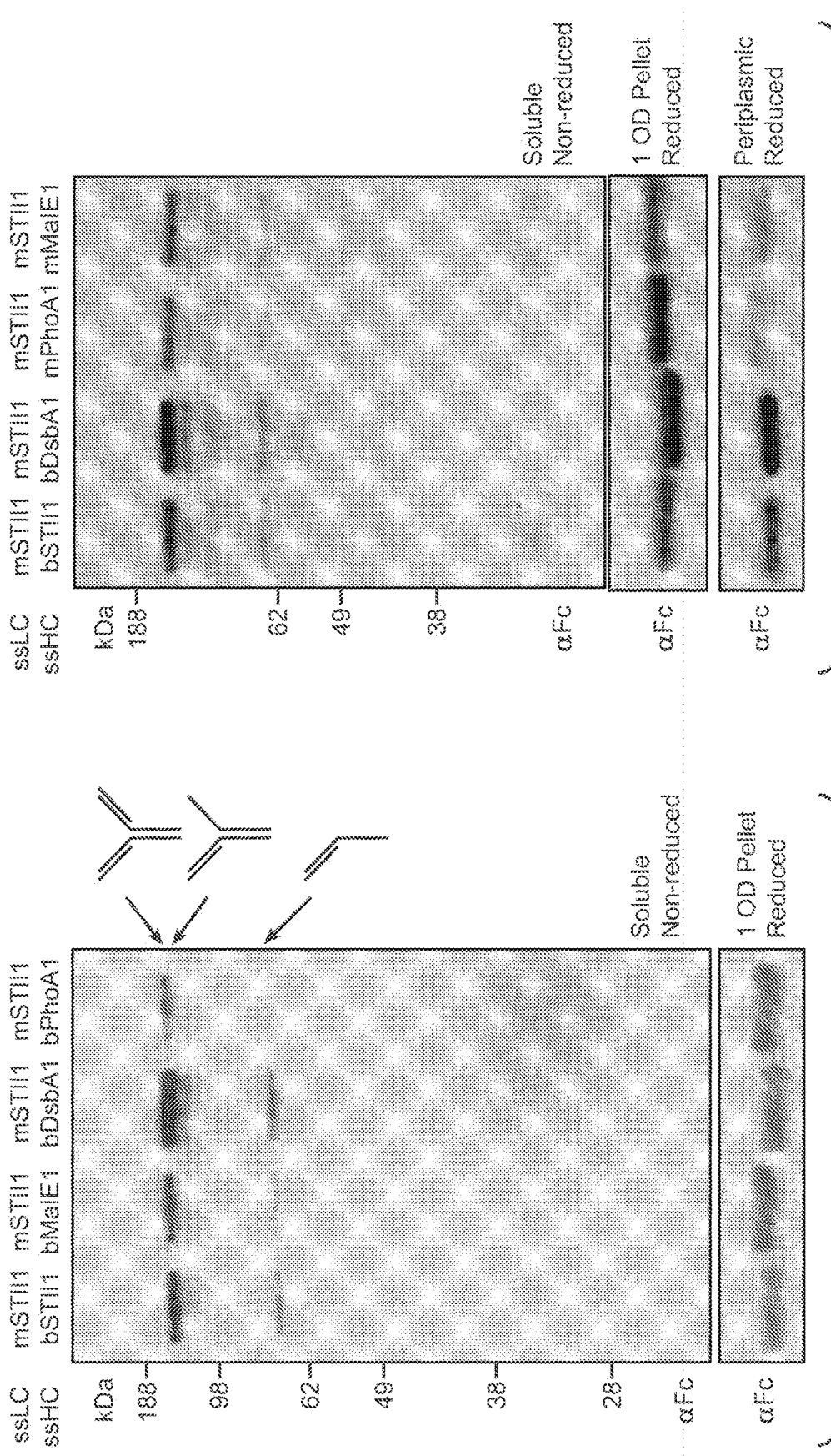

E. coli host strain 64B4 harboring the expression vector was grown in complete C.R.A.P. phosphate limiting media in a shake flask for 24 hrs and end point samples were normalized by $OD_{550}$. (1A) Top panel: Western blot of soluble heavy chain-containing species. 64B4 cells carrying pBR-mSTII1-bSTII1-5D5 (mSTII1, bSTII1), pBR-mSTII1-bMalE1-5D5 (mSTII1, bMalE1), pBR-mSTII1-bDsbA1-5D5 (mSTII1, bDsbA1), or pBR-mSTII1-bPhoA1-5D5 (mSTII1, bPhoA1) were lysed and the aqueous soluble fraction was separated by non-reducing SDS-PAGE electrophoresis followed by Western blot probing with HRP conjugated ale antibody. The resulting blot shows heavy chain-containing species corresponding to full-length 5D5 antibody, heavy chain-heavy chain-light chain, and heavy chain-light chain from top to bottom. Bottom panel: end point samples were normalized to 1 $OD_{550}$ and pelleted. Total proteins were denatured and reduced by mixing with tricine sample buffer containing 0.2M DTT. Heavy chain migrated as a single band on SDS-PAGE at a molecular weight of around 49 kDa and were probed by αFc antibody. Heavy chain bands that migrated slower on the gel contained precursors, as confirmed by the Edman protein sequencing. (1B) Levels of soluble heavy chain in the periplasm. End point samples of 64B4 cells harboring pBR-mSTII1-bSTII1-5D5 (mSTII1, bSTII1), pBR-mSTII1-bMalE1-5D5 (mSTII1, bMalE1), pBR-mSTII1-bDsbA1-5D5 (mSTII1, bDsbA1), pBR-mSTII1-bPhoA1-5D5 (mSTII1, bPhoA1) were treated by osmotic shock. The supernatant was collected, denatured and reduced by tricine buffer containing 0.2 M DTT. Reduced heavy chain migrated as a single band at around 49 kDa and was probed with αFc. (1C) Top panel: Non-reducing western blot of 64B4 cells carrying pBR-mSTII1-bSTII1-5D5 (mSTII1, bSTII1), pBR-mSTII1-bDsbA1-5D5 (mSTII1, bDsbA1), pBR-mSTII1-mPhoA1-5D5 (mSTII1, mPhoA1), and pBR-mSTII1-mMalE1-5D5 (mSTII1, mMalE1). Middle panel: Total heavy chain in the 1 $OD_{550}$ pellet of the same samples were reduced by DTT and analyzed by Western blot. Bottom panel: Periplasmic extracts of the same samples were reduced and analyzed by Western blot with αFc antibody. All the expression plasmids are named as such that the first signal peptide TIR variant is for light chain and the second signal peptide TIR variant is for heavy chain. For instance, mSTII1-bSTII1-5D5 means STII signal sequence with a TIR of 1 for light chain and a mluI restriction site upstream; bSTII1 means an STII signal sequence with a TIR of 1 for HC with a bst signal sequence upstream; 5D5 is the antibody name.

FIGS. 2A and 2B: depict the effect of use of different signal peptides on the cellular localization of heavy chain by immunogold electron microscopy. A64B4 cells carrying constructs expressing various signal peptides were cultured in shake flasks for 24 hrs. End point samples were fixed, embedded, and cryosectioned. The cryosections were probed with HRP-conjugated αFc antibody and gold conjugated αHRP secondary antibody. Immunostained samples were visualized by transmission electron microscope (TEM). (2A) shows A64B4 cells carrying pBR-mSTII1-bSTII1-5D5 (mSTII1, bSTII1). (2B) shows A64B4 cells carrying pBR-mSTII1-bDsbA1-5D5 (mSTII1, bDsbA1). The periplasmic space is pointed out by black arrows. Immunogold signals are pointed out by black arrowheads.

FIGS. 3A and 3B: depict the effect of signal peptide hydrophobicity on heavy chain accumulation in the periplasm. (3A) shows the levels of periplasmic soluble heavy chain in the absence of light chain. Periplasmic extracts from 64B4 cells carrying pBR-bDsbA1-5D5HC (bDsbA1), pBR-bDsbA1 L11I-5D5HC (bDsbA1 L11I), pBR-bDsbA1 L11S-5D5HC (bDsbA1 L11S), pBR-bSTII1-5D5HC (bSTII1), pBR-bSTII1 S11L codon1-5D5HC (bSTII1 codon1), or pBR-bSTII1 S11L codon2-5D5HC (bSTII1 codon2) were analyzed by Western blot. Reduced heavy chain migrated at around 49 kDa and was probed by αFc antibody. (3B) shows the levels of periplasmic soluble heavy chain with co-expression of light chain. Periplasmic extracts from 64B4 carrying pBR-mSTII1-bSTII1-5D5 (mSTII1, bSTII1), pBR-mSTII1-bMalE1-5D5 (mSTII1, bMalE1), pBR-mSTII1-bDsbA1-5D5 (mSTII1, bDsbA1), pBR-mSTII1-bPhoA1-5D5 (mSTII1, bPhoA1), pBR-mSTII1-bDsbA1 L11I-5D5 (mSTII1, bDsbA1 L11I), pBR-mSTII1-bDsbA1 L11S-5D5 (mSTII1, bDsbA1 L11S), pBR-mSTII1-bSTII1 S11L-5D5 (mSTII1, bSTII1 S11L), or pBR-mSTII1-bSTII1 S11I-5D5 (mSTII1, bSTII1 S11I) were analyzed by Western blot. Reduced heavy chain was detected by αFc antibody.

Figure 4A:
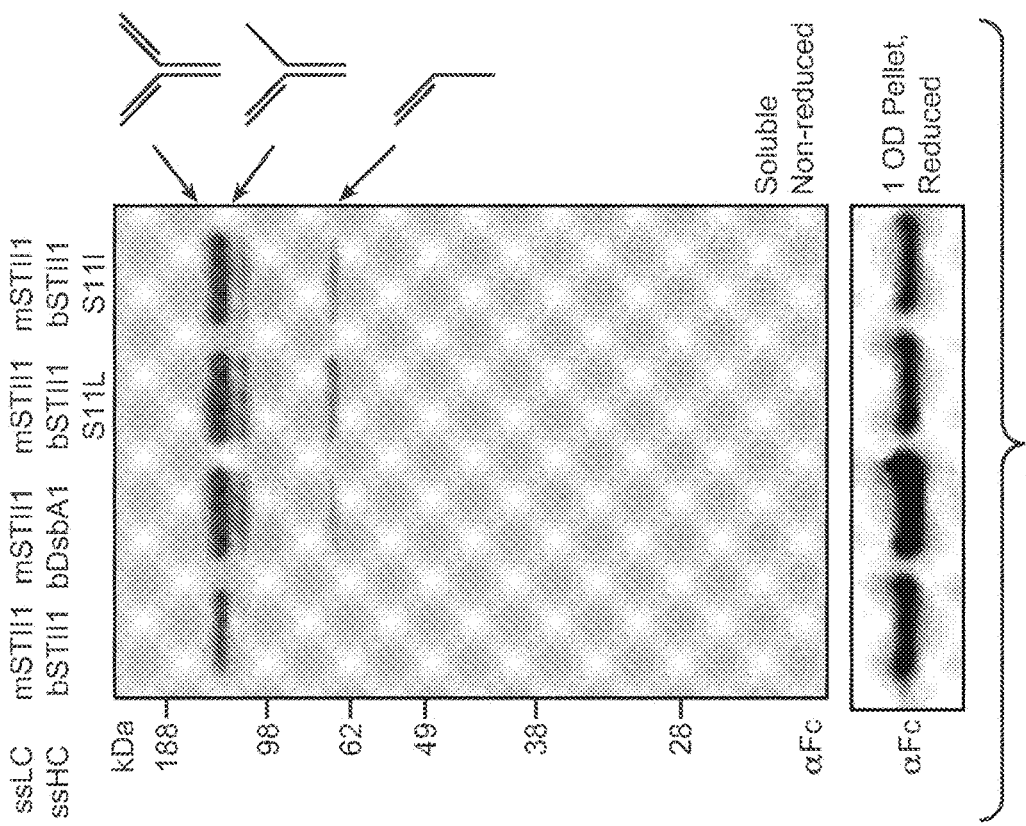
Figure 4B:
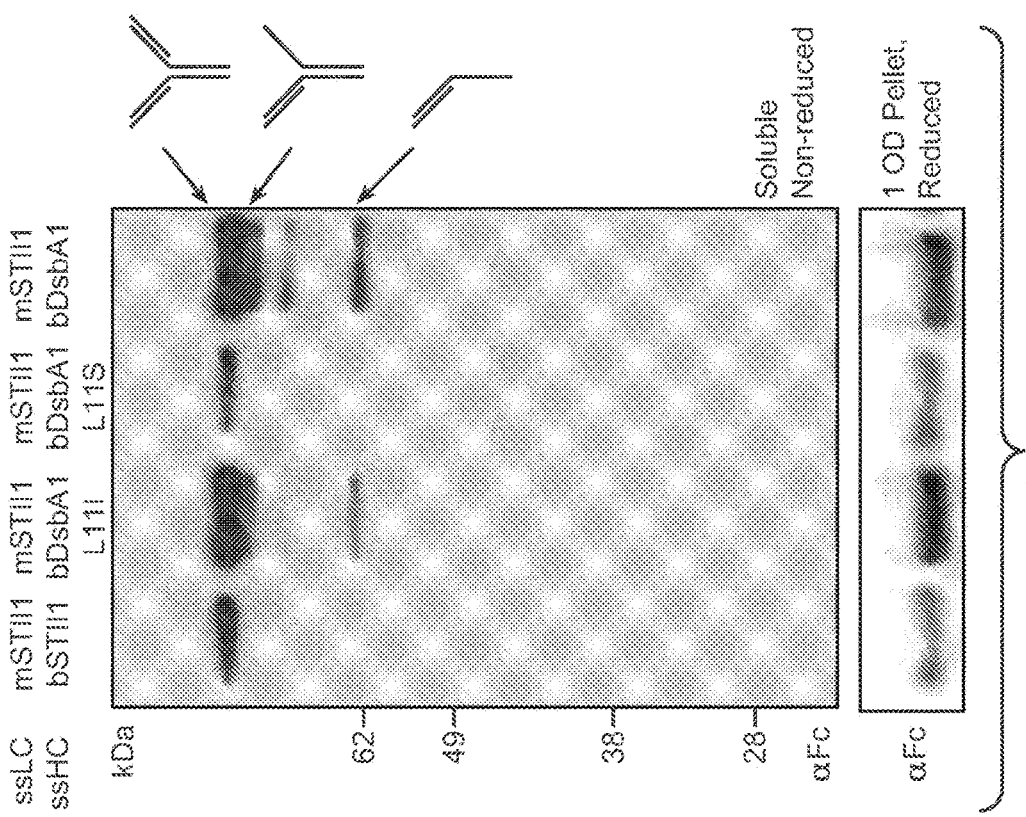

FIGS. 4A and 4B: depict the effect of signal peptide hydrophobicity on full-length 5D5 level. Top panels: whole cell lysates from 64B4 harboring (A) pBR-mSTII1-bSTII1-5D5 (mSTII1, bSTII1), pBR-mSTII1-bDsbA1 L11I-5D5 (mSTII1, bDsbA1 L11I), pBR-mSTII1-bDsbA1 L11S-5D5 (mSTII1, bDsbA1 L11S), pBR-bDsbA1-5D5HC (bDsbA1) (B) pBR-mSTII1-bSTII1-5D5 (mSTII1, bSTII1), pBR-bDsbA1-5D5HC (bDsbA1), pBR-mSTII1-bSTII1 S11L-5D5 (mSTII1, bSTII1 S11L), or pBR-mSTII1-bSTII1 S11I-5D5 (mSTII1, bSTII1 S11I) were analyzed by non-reducing SDS-PAGE gel followed by Western blot probing with αFc antibody. Heavy chain-containing species are pointed out. Bottom panels: total heavy chain protein in the 1 $OD_{550}$ pellet from the same samples used in the top panels were analyzed by reducing SDS-PAGE gel and Western blot. Heavy chain migrating at 49 kDa was probed with αFc antibody.

Figure 5:
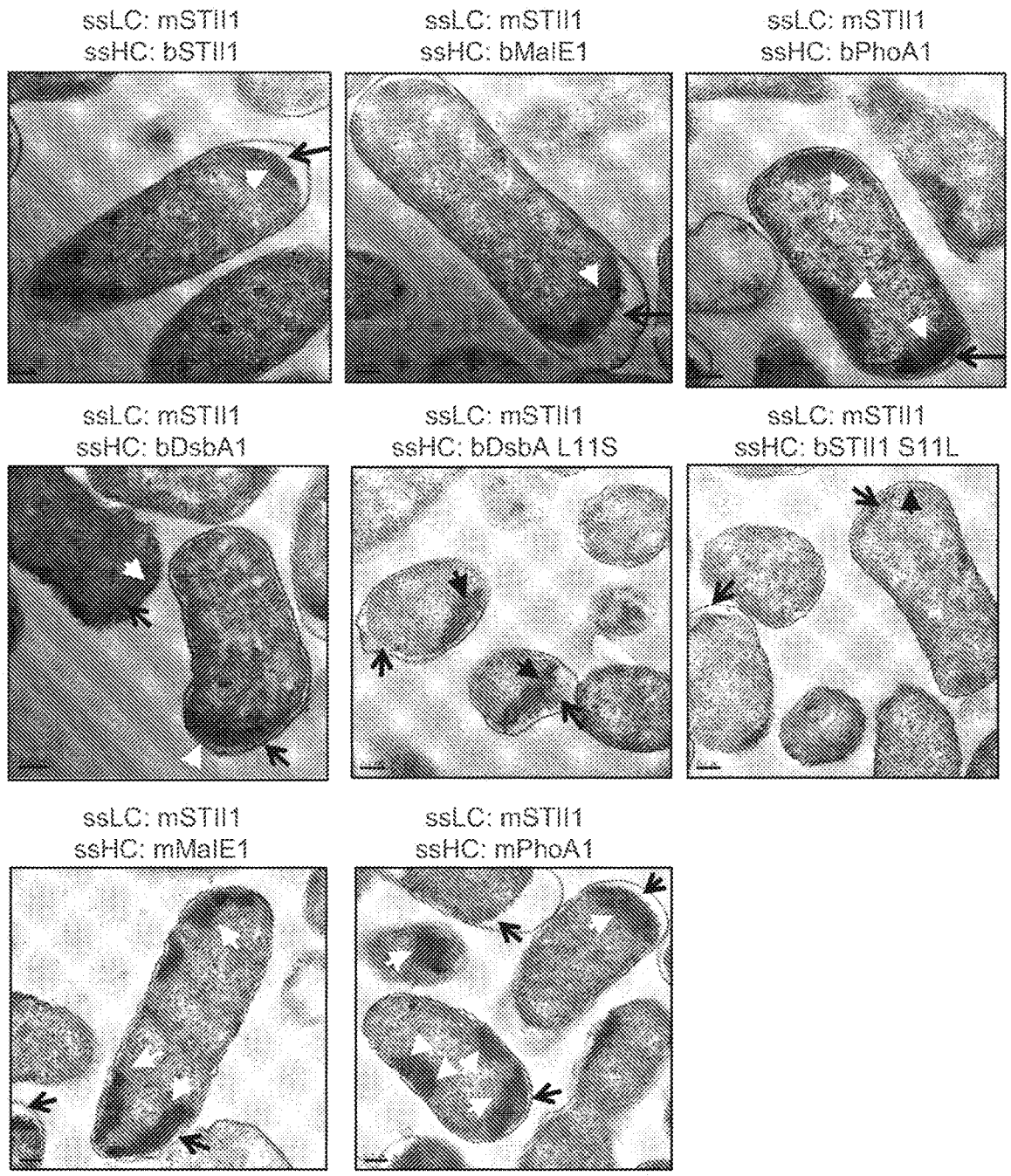

FIG. 5: depicts the effect of the signal peptide and its hydrophobicity on the cellular localization of inclusion bodies. End point samples from cultures of 64B4 carrying pBR-mSTII1-bSTII1-5D5 (mSTII1, bSTII1), pBR-mSTII1-bMalE1-5D5 (mSTII1, bMalE1), pBR-mSTII1-bPhoA1-5D5 (mSTII1, bPhoA1), pBR-mSTII1-bDsbA1-5D5 (mSTII1, bDsbA1), pBR-mSTII1-bDsbA1 L11S-5D5 (mSTII1, bDsbA1 L11S), pBR-mSTII1-bSTII1 S11L-5D5 (mSTII1, bSTII1 S11L), pBR-mSTII1-mMalE1-5D5 (mSTII1, mMalE1), or pBR-mSTII1-mPhoA1-5D5 (mSTII1, mPhoA1) were fixed, embedded, sectioned into ultrathin slices, and visualized under TEM. The periplasmic space is pointed out by arrows and the inclusion bodies are pointed out by arrowheads.

Figure 6:
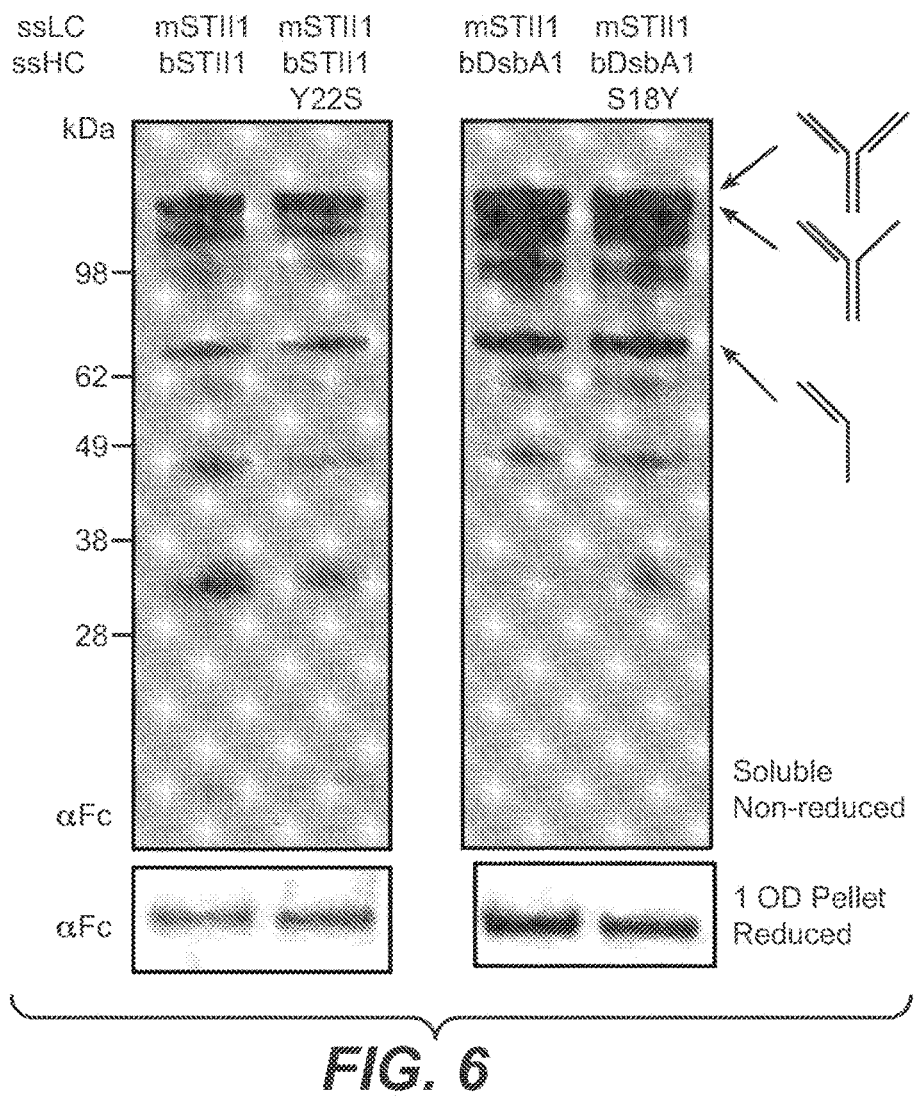

FIG. 6: depicts western blot analysis of Ser/Tyr mutations in the C-terminal region. Top panel: whole cell lysates from 64B4 cells harboring pBR-mSTII1-bSTII1-5D5 (mSTII1, bSTII1), pBR-mSTII1-bSTII1 Y22S-5D5 (mSTII1, bSTII1 Y22S), pBR-bDsbA1-5D5HC (bDsbA1), or pBR-bDsbA1 S18Y-5D5HC (bDsbA1 S18Y) were analyzed by non-reducing Western blot probing with αFc. Heavy chain-containing species including full-length 5D5, heavy-heavy-light, and heavy-light are indicated. Bottom panel: total proteins in the 1 $OD_{550}$ pellet were reduced by DTT and analyzed by Western blot. The reduced heavy chain migrated at ~49 kDa.

Figure 7B:
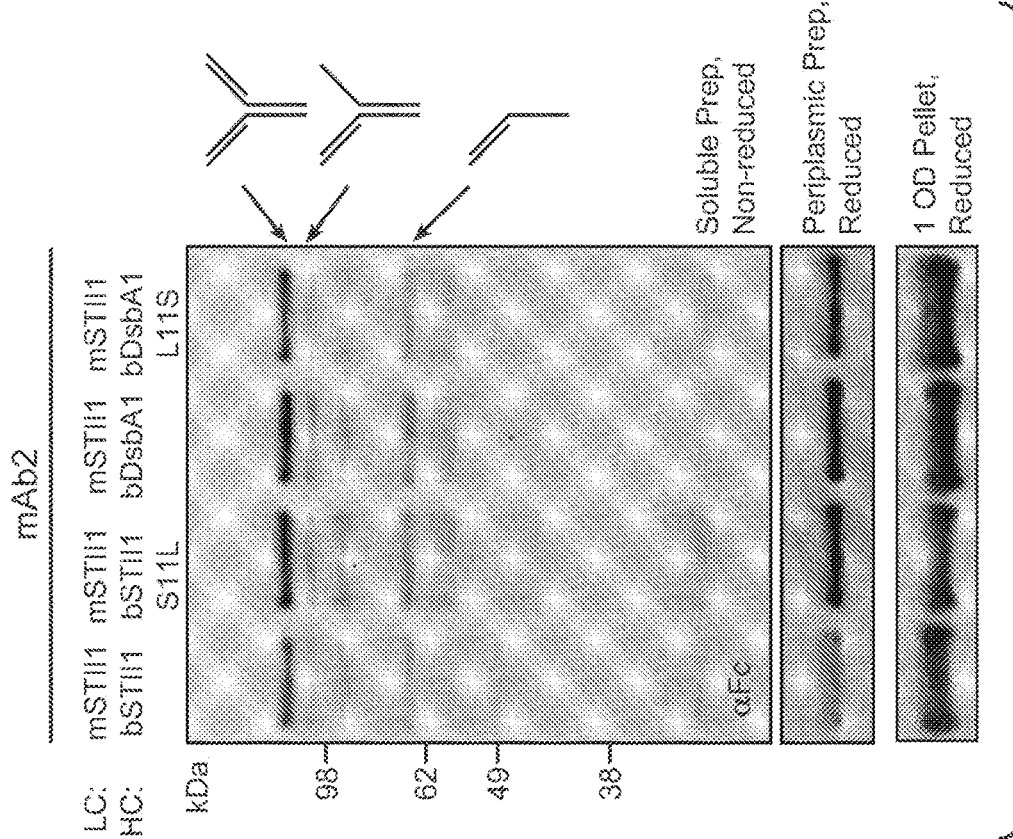
Figure 7A:
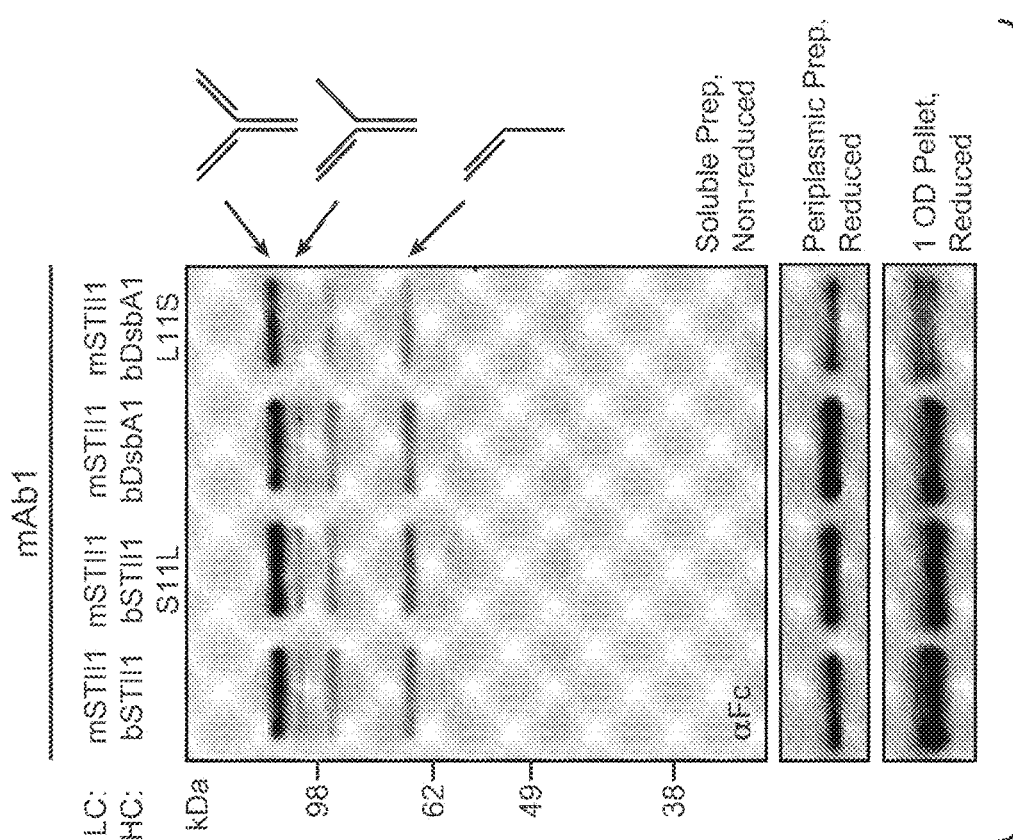

FIGS. 7A and 7B: depict the effects of signal peptide hydrophobicity on full-length antibody levels and periplasmic soluble heavy chain levels for mAb1 and mAb2. (7A) Top panel shows whole cell lysates from 64B4 harboring pBR-mSTII1-bSTII1-mAb1 (mSTII1, bSTII1), pBR-mSTII1-bSTII1 S11L-mAb1 (mSTII1, bSTII1 S11L), pBR-mSTII1-bDsbA1-mAb1 (mSTII1, bDsbA1), and pBR-mSTII1-bDsbA1 L11S-mAb1 (mSTII1, bDsbA1 L11S), which were analyzed by non-reducing SDS-PAGE gel followed by Western blot probing with αFc antibody. Heavy chain-containing species are indicated with arrows. Middle panel: shows periplasmic proteins from the same samples, which were extracted, reduced by DTT, and analyzed by SDS-PAGE gel followed by Western blot probing with αFc antibody. Bottom panel shows total heavy chain protein in the 1 $OD_{550}$ pellets of the same samples, which were reduced by DTT and analyzed by Western blot. (7B) Top panel shows whole cell lysates from 64B4 harboring pBR-mSTII1-bSTII1-mAb2 (mSTII1, bSTII1), pBR-mSTII1-bSTII1 S11L-mAb2 (mSTII1, bSTII1 S11L), pBR-mSTII1-bDsbA1-mAb2 (mSTII1, bDsbA1), and pBR-mSTII1-bDsbA1 L11S-mAb2 (mSTII1, bDsbA1 L11S), which were analyzed by non-reducing SDS-PAGE gel followed by Western blot probing with αFc antibody. Heavy chain-containing species are indicated with arrows. Middle panel shows periplasmic proteins from the same samples, which were extracted, reduced by DTT, and analyzed by SDS-PAGE gel followed by Western blot probing with αFc antibody. Bottom panel shows total heavy chain protein in the 1 $OD_{550}$ pellets of the same samples, which were reduced by DTT and analyzed by Western blot.

DETAILED DESCRIPTION OF THE INVENTION

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "cistron," as used herein, is intended to refer to a genetic element broadly equivalent to a translational unit comprising the nucleotide sequence coding for a polypeptide chain and adjacent control regions. "Adjacent control regions" include, for example, a translational initiation region (TIR; as defined herein below) and a termination region.

A "polycistronic" expression vector refers to a single vector that contains and expresses multiple cistrons under the regulatory control of one single promoter. A common example of polycistronic vector is a "dicistronic" vector that contains and expresses two different polypeptides under the control of one promoter. Upon expression of a dicistronic or polycistronic vector, multiple genes are first transcribed as a single transcriptional unit, and then translated separately.

A "separate cistron" expression vector according to the present invention refers to a single vector comprising at least two separate promoter-cistron pairs, wherein each cistron is under the control of its own promoter. Upon expression of a separate cistron expression vector, both transcription and translation processes of different genes are separate and independent.

The "translation initiation region" or TIR or translational initiation region or translational initiation sequence, as used herein refers to a nucleic acid region providing the efficiency of translational initiation of a gene of interest. In general, a TIR within a particular cistron encompasses the ribosome binding site (RBS) and sequences 5' and 3' to RBS. The RBS is defined to contain, minimally, the Shine-Dalgarno region and the start codon (AUG). Accordingly, a TIR also includes at least a portion of the nucleic acid sequence to be translated. Preferably, a TIR includes a secretion signal sequence encoding a signal peptide that precedes the sequence encoding for the light or heavy chain within a cistron. A TIR variant contains sequence variants (particularly substitutions) within the TIR region that alter the property of the TIR, such as its translational strength as defined herein below. Preferably, a TIR variant of the invention contains sequence substitutions within the first 2 to about 14, preferably about 4 to 12, more preferably about 6 codons of the secretion signal sequence that precedes the sequence encoding for the light or heavy chain within a cistron.

The term "translational strength" as used herein refers to a measurement of a secreted polypeptide in a control system wherein one or more variants of a TIR is used to direct secretion of a polypeptide and the results compared to the wild-type TIR or some other control under the same culture and assay conditions.

"Signal peptide" (also termed "signal sequence") refers to a short peptide that can be used to direct a newly synthesized protein of interest through a cellular membrane, usually the inner membrane or both inner and outer membranes of prokaryotes. The signal peptide encoded by the secretion signal sequence may be endogenous to the host cells, or they may be exogenous, including signal peptides native to the polypeptide to be expressed. The signal peptide is typically present at the amino terminus of a polypeptide to be expressed, and are typically removed enzymatically between biosynthesis and secretion of the polypeptide from the cytoplasm. Thus, the signal peptide is usually not present in a mature protein product. Signal peptides (e.g. prokaryotic, e.g., E. coli signal peptides) are commonly composed of three distinct regions: an N-terminal region which typically contains at least 1 or 2 positively charged amino acid residues, a hydrophobic core region termed the H-region (also termed H domain), and a C-terminal region recognized by the signal peptidase. One of skill in the art understands how to define the N-terminal region, H-region and C-terminal regions of a given signal peptide.

By "average hydrophobicity" of a peptide (or portion of a peptide) is meant the average hydrophobicity as calculated using the formula: average hydrophobicity of a peptide (or portion of a peptide)=total (sum) hydrophobicity of the peptide (or portion of a peptide)/number of amino acids in the peptide (or portion of a peptide). "Total" or "sum" hydrophobicity is calculated by (a) assigning each amino acid in the peptide (or portion of a peptide) a normalized consensus hydrophobicity value according to Eisenberg, D. et al, J Mol Biol (1984) 179:125-142. Table 1 (page 126), then adding up the normalized consensus hydrophobicity values for the amino acids in the peptide (or portion of the peptide). In some embodiments, the average hydrophobicity is calculated for the H-domain of the signal peptide.

"Operably linked" refers to a juxtaposition of two or more components, wherein the components so described are in a relationship permitting them to function in their intended manner. For example, a promoter is operably linked to a coding sequence if it acts in cis to control or modulate the transcription of the linked sequence. Generally, but not necessarily, the DNA sequences that are "operably linked" are contiguous and, where necessary to join two protein coding regions or in the case of a secretory leader, contiguous and in reading frame. However, although an operably linked promoter is generally located upstream of the coding sequence, it is not necessarily contiguous with it. Operably linked enhancers can be located upstream, within or downstream of coding sequences and at considerable distances front the promoter. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

"Regulatory elements" as used herein, refer to nucleotide sequences present in cis, necessary for transcription and translation of a polynucleotide encoding a heterologous polypeptide into polypeptides. The transcriptional regulatory elements normally comprise a promoter 5' of the gene sequence to be expressed, transcriptional initiation and termination sites, and polyadenylation signal sequence. The term "transcriptional initiation site" refers to the nucleic acid in the construct corresponding to the first nucleic acid incorporated into the primary transcript, i.e., the mRNA precursor; the transcriptional initiation site may overlap with the promoter sequences.

A "promoter" refers to a polynucleotide sequence that controls transcription of a gene or sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). With inducible promoters, the activity of the promoter increases or decreases in response to a signal.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated" polypeptide (e.g., an antibody) is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE (sodium dodecyl sulfate polyacrylamide gel electrophoresis) under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amities or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

As used herein, "polypeptide" refers generally to peptides and proteins from any cell source having more than about ten amino acids. "Heterologous" polypeptides are those polypeptides foreign to the host cell being utilized, such as a human protein produced by E. coli. While the heterologous polypeptide may be prokaryotic or eukaryotic, preferably it is eukaryotic, more preferably mammalian, and most preferably human. Preferably, it is a recombinantly produced, or recombinant polypeptide. "Heterologous" polypeptides are those polypeptides foreign to the host cell being utilized, such as a human protein produced by E. coli. While the heterologous polypeptide may be prokaryotic or eukaryotic, preferably it is eukaryotic, more preferably mammalian, and most preferably human. Preferably, it is a recombinantly produced, or recombinant polypeptide.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; 1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA) and variants thereof such as RETEVASE™ and TNKASE™; bombesin; thrombin; hemopoietic growth factor; tumor necrosis factor-alpha and -beta; antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), enkephalinase; a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin like growth factor-I and -II (IGF-I and IGF-II); des(I-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; Apo2 ligand; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

In some embodiments, polypeptides herein include human serum albumin (HSA), 2C4, tissue factor, anti-tissue factor, anti-CD20, anti-HER-2, heregulin, anti-IgE, anti-CD11a, anti-CD18, VEGF and receptors and antibodies thereto such as rhuFab V2 and AVASTIN™, growth hormone and its variants, such as hGH, growth hormone receptors, growth hormone releasing protein (GHRP), LIV-1 (EP 1,263,780), TRAIL, tumor necrosis factor (TNF) and antibodies thereto, TNF receptor and related antibodies, TNF-receptor-IgG, TNF receptor associated factors (TRAFs) and inhibitors thereof, Factor VIII, Factor VIII B domain, interferons such as interferon-gamma, transforming growth factors (IGFs) such as TGF-beta, anti-TGF such as anti-TGF-beta, activin, inhibin, anti-activin, anti-inhibin, tissue-plasminogen activators and their variants such as t-PA, RETEPLASE™, and TNKase, anti-Fas antibodies, Apo-2 ligand; Apo-2 ligand inhibitor; Apo-2 receptor, Apo-3, apoptotic factors, Ced-4, DcR3, death receptor and agonist antibodies (DR4, DR5), lymphotoxin (LT), prolactin, prolactin receptor, SOB proteins, WISP (wnt-induced secreted proteins), neurotoxin-3 (NT-3), nerve growth factor (NGF) and anti-NGF, DNase, hepatitis antigen, herpes simplex antigen, leptin, insulin-like growth factors (IGFs) such as IGF-1 and IGF-2 and their binding proteins and receptors such as IGFBP-1-IGFBP-6, insulin, fibroblast growth factors (TGFs) such as FGF-17, Toll protein, TIE ligands, CD40 and anti-CD40, immunoadhesins, subtilisin, hepatocyte growth factor (HGF), thrombopoietin (TPO), interleukins such as IL-2, IL-12, IL-17, IL-22, IL-8, IL-9, and antibodies thereto, and prostrate-specific cancer antigen (PSCA).

Particularly preferred polypeptides are recombinant polypeptides, in some embodiments, antibodies, which include monoclonal antibodies and humanized antibodies. Such antibodies may be full-length antibodies or antibody fragments. In some embodiments, these antibodies are human or humanized antibodies. In some embodiments, the antibody is an anti-c-met, anti-IgE, anti-CD18, anti-VEGF, anti-tissue factor, 2C4, anti-Her-2, anti-CD20, anti-CD40, or anti-CD11a antibody. Antibody fragments encompassed within the definition of polypeptide, in some embodiments, comprise a light chain, in some embodiments, a kappa light chain. Such exemplary fragments include, for example, a Fab, Fab', F(ab')$_2$, or F(ab')$_2$-leucine zipper (LZ) fusion, and a one-armed antibody.

Protein "expression" refers to conversion of the information encoded in a gene into messenger RNA (mRNA) and then to the protein.

An "immunoconjugate" (interchangeably referred to as "antibody-drug conjugate," or "ADC") means an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

A "blocking" antibody or an antibody "antagonist" is one which inhibits or reduces biological activity of the antigen it binds. In some embodiments, blocking antibodies or antagonist antibodies completely inhibit the biological activity of the antigen.

An "agonist antibody", as used herein, is an antibody which mimics at least one of the functional activities of a polypeptide of interest (e.g., HGF).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Desirably the Kd is $1\times10^{-7}$, $1\times10^{-8}$, $5\times10^{-8}$, $1\times10^{-9}$, $3\times10^{-9}$, $5\times10^{-9}$, or even $1\times10^{-10}$ or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following. In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol. 293:865-881). To establish conditions for the assay, microliter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 µl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^6$ $M^{-1}$ $S^{-1}$ by the surface plasmon. resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 uM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 µl/min. In some embodiments, the following modifications are used for the surface Plasmon resonance assay method: antibody is immobilized to CM5 biosensor chips to achieve approximately 400 RU, and for kinetic measurements, two-fold serial dilutions of target protein are injected in PBST buffer at 25° C. with a flow rate of about 30 ul/minute. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol. 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

A "naked antibody" is an antibody that is not conjugated to a heterologous molecule, such as a cytotoxic moiety or radiolabel.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (e.g., Ghetie et al., *Ann. Rev. Immunol.* 18:739-766 (2000), Table 1). Antibodies with substitutions in an Fc region thereof and increased serum half-lives are also described in WO00/42072, WO 02/060919; Shields et al., *J. Biol. Chem.* 276:6591-6604 (2001); Hinton, *J. Biol. Chem.* 279:6213-6216 (2004)). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one preferred embodiment, the serum albumin peptide to be attached comprises an amino acid sequence of DICLPRWGCLW (SEQ ID NO: 48). In another embodiment, the half-life of a Fab is increased by these methods. See also, Dennis et al. *J. Biol. Chem.* 277:35035-35043 (2002) for serum albumin binding peptide sequences.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, and $IgA_2$. The heavy chain constant domains that correspond to the different classes of immunoglobulins are called α, δ, ε, γ, and μ, respectively.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

The term "one-armed antibody" or "one-armed antibodies" refers to an antibody that comprises (1) a variable domain joined by a peptide bond to a polypeptide comprising a CH2 domain, a CH3 domain or a CH2-CH3 domain and (2) a second CH2, CH3 or CH2-CH3 domain, wherein a variable domain is not joined by a peptide bond to a polypeptide comprising the second CH2, CH3 or CH2-CH3 domain. In one embodiment, the one-armed antibody comprises 3 polypeptides (1) a first polypeptide comprising a variable domain (e.g., VH), CH1, CH2 and CH3, (2) a second polypeptide comprising a variable domain (e.g., VL) and a CL domain, and (3) a third polypeptide comprising a CH2 and CH3 domain. In an embodiment, the third polypeptide does not comprise a variable domain. In another embodiment, the one-armed antibody has a partial hinge region containing the two cysteine residues which form disulfide bonds linking the constant heavy chains. In one embodiment, the variable domains of the one armed antibody form an antigen binding region. In another embodiment, a variable domain of the one armed antibody is a single variable domain, wherein each single variable domain is an antigen binding region.

The term "knob-into-hole" or "KnH" technology as mentioned herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprises different target recognition sequences (e.g., including affibodies, peptibodies and other Fc fusions).

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H 1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., CH2 and/or CH3 sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG-1, IgG-2, IgG-3, or IgG4 subtypes, IgA (including IgA-1 and IgA-2), IgE, IgD, or IgM.

"Hinge region" in the context of an antibody or half-antibody is generally defined as stretching from Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. Prior to the present invention, FcgammaR binding was generally attributed to amino acid residues in the lower hinge region of an IgG Fc region.

The "CH2 domain" of a human IgG Fc region usually extends from about residues 231 to about 340 of the IgG. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22:161-206 (1985).

The "CH3 domain" comprises the stretch of residues C-terminal to a CH2 domain in an Fc region (i.e. from about amino acid residue 341 to about amino acid residue 447 of an IgG).

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc complex" as used herein refers to two CH2 domains of an Fc region interacting together and/or two CH3 domains of an Fc region interacting together, wherein the CH2 domains and/or the CH3 domains interact through bonds and/or forces (e.g., van der Waals, hydrophobic, hydrophilic forces) that are not peptide bonds.

"Fc component" as used herein refers to a hinge region, a CH2 domain or a CH3 domain of an Fc region.

"Fc CH component" or "FcCH" as used here in refers to a polypeptide comprising a CH2 domain, a CH3 domain, or CH2 and CH3 domains of an Fc region.

As used herein, "antibody mutant" or "antibody variant" refers to an amino acid sequence variant of an antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, see below) with the species-dependent antibody residues, after aligning the sequences and introducing gaps, if necessary, to achieve the maximum percent sequence identity. In some embodiments, none of N-terminal, C-terminal, or internal extensions, deletions, or insertions into the antibody sequence outside of the variable domain shall be construed as affecting sequence identity or similarity.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

"Treatment" refers to both therapeutic treatment and prophylactic or preventative measures. Those in need of treatment include those already having a benign, pre-cancerous, or non-metastatic tumor as well as those in which the occurrence or recurrence of cancer is to be prevented.

The term "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma including liposarcoma and synovial cell sarcoma neuroendocrine tumors (including carcinoid tumors, gastrinoma, and islet cell cancer), mesothelioma, schwannoma (including acoustic neuroma meningionia, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer) colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer and multiple myeloma.

The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation.

By "dysplasia" is meant any abnormal growth or development of tissue, organ, or cells. Preferably, the dysplasia is high grade or precancerous.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass.

Both stimulatory and inhibitory molecular pathways within the tumor cell regulate this behavior, and interactions between the tumor cell and host cells in the distant site are also significant.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

By "primary tumor" or "primary cancer" is meant the original cancer and not a metastatic lesion located in another tissue, organ, or location in the subject's body.

By "benign tumor" or "benign cancer" is meant a tumor that remains localized at the site of origin and does not have the capacity to infiltrate, invade, or metastasize to a distant site.

By "tumor burden" is meant the number of cancer cells, the size of a tumor, or the amount of cancer in the body. Tumor burden is also referred to as tumor load.

By "tumor number" is meant the number of tumors.

By "subject" is meant a mammal, including, but not limited to, a human or non-human mammal, such as a bovine, equine, canine, ovine, or feline. Preferably, the subject is a human.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly ctyptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma II and calicheamicin omegaI1 (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxonibicin and deoxydoxorubicin), epirubicin, esorubicin, idarubicin, marcellomycin, mitomycins such as mitomycin C, myeophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; rnitoxantrone; mopidamnol; nitraerine; pentostatin; phenamet; pirarubicin; losoxamrorte; podophyllinie acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Farmers, Schaumberg, Ill.), and TAXOTERE® doxetaxet (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide, mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-EU and leucovorin); topoisomerase inhibitor RFS 2000; difluorometlhylornithine (DMFO); retinoids such as retinoic acid; capecitabine; combretastatin; VELCADE bortezomib; REVLIMID lenalidomide; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

A "biologically active" or "functional" polypeptide (such as a heterologous polypeptide) is one capable of exerting one or more of its natural activities in structural, regulatory, biochemical or biophysical events.

A "biologically active" or "functional" antibody is one capable of exerting one or more of its natural activities in structural, regulatory, biochemical or biophysical events. For example, a biologically active antibody may have the ability to specifically bind an antigen and the binding may in turn elicit or alter a cellular or molecular event such as signaling transduction or enzymatic activity. A biologically active antibody may also block ligand activation of a receptor or act as an agonist antibody. The capability of an antibody to exert one or more of its natural activities depends on several factors, including proper folding and assembly of the polypeptide chains.

Compositions of the Invention and Methods Using Same

Provided herein are methods using signal peptides, and variant signal peptides, suitable, e.g., for methods of producing heterologous polypeptides (e.g., antibodies, e.g., full-length antibodies). Methods for characterizing signal peptides are known in the art. In one scheme, signal peptides are commonly composed of three distinct regions: an N-terminal region which contains 1 or 2 positively charged amino acid residues, a hydrophobic core region often referred as the H-region (also termed H domain), and a C-terminal region recognized by the signal peptidase. In some embodiments, the H-region is about 10-16 residues long. Hydrophobicity of the signal peptide may be calculated using the Eisenberg scale. See Eisenberg, D. et al, J Mol Biol (1984) 179:125-142. Briefly, each amino acid is assigned a normalized consensus hydrophobicity value (see Eisenberg, et al. supra at Table I (page 126). The sum hydrophobicity (also termed total hydrophobicity) is calculated by adding up the consensus hydrophobicity value for each amino acid of the signal peptide (or, e.g., to calculate the total hydrophobicity value for the H-region, the consensus hydrophobicity value for each amino acid in the H-region is added). Average hydrophobicity is calculated using the following formula: Average hydrophobicity=total (sum) hydrophobicity/number of amino acids. In some embodiments, the average hydrophobicity of the entire signal peptide is calculated. In some embodiments, average hydrophobicity of the H-region (also termed H-domain) is calculated.

Mutation of signal peptide sequence may be done using methods known in the art. Techniques for genetically modifying a DNA in this manner have been reviewed in *Mutagenesis: a Practical Approach,* M. J. McPherson, Ed., (IRL Press, Oxford, UK. (1991), and include site-directed mutagenesis, cassette mutagenesis and polymerase chain reaction (PCR) mutagenesis, for example. Other methods for mutagenesis include QuickChange site-directed mutagenesis and overlap extension PCR.

In another aspect, provided is use of signal peptide with greater average hydrophobicity (e.g., average hydrophobicity of the H region, or average hydrophobicity of the entire signal peptide) than DsbA signal peptide, e.g., for use in any of the methods of the invention, e.g., making a heterologous polypeptide (e.g., an antibody), secreting a heterologous polypeptide from a cell, making a soluble heterologous polypeptide, secreting to the periplasm a soluble heterologous polypeptide, making a mature heterologous polypeptide, secreting to the periplasm a mature heterologous polypeptide, translocating a heterologous polypeptide, optimizing secretion of a heterologous polypeptide. Exemplary signal peptides that have greater average hydrophobicity than DsbA include: FlgI, NikA, AsmA, TolB, YraI, FecB, CemH, TreA, FocC, TraU, SfmL, TorT, SfmC.

In some embodiments, the average hydrophobicity of the first signal peptide is greater than about 0.5. In some embodiments, the average hydrophobicity of the first signal peptide is greater than about 0.6. In some embodiments, the average hydrophobicity of the first signal peptide is greater than about 0.7. In some embodiments, the average hydrophobicity of the first signal peptide is greater than about 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7 or higher. In some embodiments, the average hydrophobicity of the second signal peptide is greater than about 0.6. In some embodiments, the average hydrophobicity of the second signal peptide is greater than about 0.7. In some embodiments, the average hydrophobicity of the second signal peptide is greater than about 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7 or higher. In some embodiments, the average hydrophobicity of the first and second signal peptides is similar (e.g., about equivalent). In some embodiments, the average hydrophobicity of the first and second signal peptides is different.

DsbA and STII signal peptides are well known in the art. The sequence of the DsbA and STII signal peptides is shown in Tables 7 and 8. The sequences of the DsbA and STII N-terminal region, H-region, and the C-terminal region are shown in Tables 7 and 8.

Methods for characterizing production and secretion of heterologous polypeptide are known in the art and some methods are described and exemplified herein. For example, a host strain harboring an expression vector(s) encoding variant signal peptides operably linked to a heterologous protein (e.g., antibody) are cultured, and polypeptide is extracted. Soluble fraction is separated by non-reducing SDS Page electrophoresis followed by Western blot analysis to determine level of full length heterologous protein that is produced. Presence of absence or level of mature verses precursor polypeptide may be determined, e.g., by Edman sequencing of protein isolated from bands on the western gel, and characterization of isolated polypeptide as possessing or lacking a signal peptide, as is well known in the art. Production of full antibody (or e.g., other heteromultimeric proteins) may be determined by running the western blot under denaturing conditions. Activity of heterologous polypeptide (e.g., antibody) may be determined using routine functional assays, as are well-known in the art. Function of the protein may be determined using a suitable functional assay. For example, binding activity may be tested using ELISA, Biacore and other methods well known in the art. Other functions may be tested using assays well-known in the art as appropriate tier the specific heterologous polypeptide.

The translational initiation region (TIR) is a major determinant of the overall translation level of a protein. The TIR includes the polynucleotide that encodes the signal sequence, and extends from immediately upstream of the Shine-Delgamo sequence to approximately twenty nucleotides downstream of the initiation codon. Modifications of this polynucleotide sequence (in some embodiments, modification within the first about 2 to about 14, about 4 to 12, about 6 codons of the sequence encoding the signal peptide) can alter the efficiency of translational initiation, thereby adjusting the level of translation of the downstream protein. TIRs have different translational strengths. In some embodiments, the first and second translational initiation regions (operably linked, e.g., to a first and second heterologous polypeptide) (and in some embodiment, the third translational initiation region, operably linked, e.g., to a third heterologous polypeptide) provide approximately equal translational strengths. In some embodiments, the relative translation strength is about one or two. In some embodiments the relative translation strength is about one. In some embodiments, the relative translation strength is about two. In some embodiments, the relative translation strength is one and/or two. In some embodiments, the relative translation strength is about three or about four. In some embodiments, the relative translation strength is selected from one or more of one, two, three, four, five, or more (such as six or seven or more). In some embodiments, the relative translation strength of the first and second TIR is about one. In some embodiments, the relative translation strength (also termed TIR strength) of the first and second TIR is about two. In some embodiments, the relative translation strength of the first, second and third TIR is about one. In some embodiments, the relative translation strength of the first, second and third TIR is about two. In some embodiments, the relative translation strength is about 2, about 3, approximately 4, about 5, about 6, about 7, or more, such as about 8, about 9, or more. In some embodiments, the relative translation strength is between 1 and 3, between 2 and 4, between 3 and 5, between 4 and 6, between 5 and 7, or between 6 and 8. In some embodiments, the relative translation strength is between 2 and 5, between 3 and 7, or between 4 and 8. In some embodiments, the relative translation strength of the first and/or second signal peptide is about 1, about 2, about 3, about 4, about 5, approximately 6, about 7, or about 8. In some embodiments, the relative translation strength of the first signal peptide is about 5 and the relative translation strength of the second signal sequence is about 8. In some embodiments, the relative translation strength of a first and second TIR is approximately equivalent. In some embodiments, the relative translation strength of a first and second TIR is different.

In some embodiments, a polynucleotide encoding a signal peptide (such as a variant signal peptide) will be provided in a vector with appropriate elements for expression of a gene of interest. In some embodiments, the vector comprises a promoter 5' to the signal sequence, a restriction enzyme recognition site 3' to the signal sequence for insertion of a gene of interest or a reporter gene, and a selectable marker, such as a drug resistance marker, for selection and/or maintenance of bacteria transformed with the resulting plasmids. Plasmid vectors are further discussed and exemplified herein. Promoters suitable for use with prokaryotic hosts are known in the art and some are exemplified and described herein.

Any reporter gene may be used which can be quantified in some manner. Thus, for example, alkaline phosphatase production can be quantitated as a measure of the secreted level of the phoA gene product. Other examples include, for example, the β-lactamase gene.

The secreted level of polypeptides can be determined, for example, by a functional assay for the polypeptide of interest, if available, radioimmunoassays (RIA), enzyme-linked immunoassays (ELISA), or by PAGE and visualization of the correct molecular weight of the polypeptide of interest. Methods for determining level of secreted polypeptide are well known in the art and some are exemplified herein.

Polypeptides

Exemplary heterologous polypeptides include a transmembrane molecule (e.g. receptor, such as a receptor tyrosine kinase) or a ligand such as a growth factor. Exemplary heterologous polypeptides include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-3; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Immunoadhesins are expressly contemplated as heterologous polypeptides according to the invention.

Antibodies

Exemplary targets for antibodies or heteromultimeric polypeptides or polypeptides or immunoadhesins include, but are not limited to, the following list: BMPI, BMP2, BMP3B (GDFIO), BMP4, BMP6, BMP8, CSFI (M-CSF), CSF2 (GM-CSF), CSF3 (G-CSF), EPO, FGFI (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21 FGF23, IGF1, IGF2, IFNAI, IFNA2, IFNA4, IFNA5, IFNA6, IFNA7, IFNBI, IFNG, IFNWI, FELI, FELI (EPSELON), FELI (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNT-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1 BB ligand), TNFS-FIO (TRAIL), INTSF11 (TRANCE), TNFSF12 (AP03L), TNFSF13 (April), TNFSF13B, TNFSF14 (HVEM-L), TNFSF15 (VEGI), TNFSF18, HGF (VEGFD), VEGF, VEGFB, VEGFC, ILIR1, IL1 R2, IL1 RL1, IL1 RL2, IL2RA, IL2RB, IL2RG, IL3RA, IL4R, IL5RA, IL6R, IL7R, IL8RA, IL8RB, IL9R, ILIORA, ILIORB, IL11RA, IL12RB1, IL12RB2, IL13RA1, IL13RA2, IL15RA, IL17R, IL18R1, IL20RA, IL21 R, IL22R, IL1 HY1, IL1 RAP, IL1 RAPL1, IL1 RAPL2, IL1 RN, IL6ST, IL18BP, IL18RAP, IL22RA2, AIF1, HGF, LEP (leptin), PTN, THPO, CCL1 (I-309), CCL2 (MCP-1/MCAF), CCL3 (MIP-1a), CCL4 (MIP-1b), CCL5 (RANTES), CCL7 (MCP-3), CCL8 (mcp-2), CCLH (eotaxin), CCL13 (MCP-4), CCL15 (MIP-1d), CCL16 (HCC-4), CCL17 (TARC), CCL18 (PARC), CCL19 (MDP-3b), CCL20 (MTP-3a), CCL21 (SLC/exodus-2), CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CXCLI (GROI), CXCL2 (GR02), CXCL3 (GR03), CXCL5 (ENA-78), CXCL6 (GCP-2), CXCL9 (MIG), CXCL10 (IP 10), CXCL11 (I-TAC), CXCL12 (SDFI), CXCL13, CXCL14, CXCL16, PF4 (CXCL4), PPBP (CXCL7), CX3CL1 (SCYDI), SCYEI, XCLI (Iymphotactin), XCL2 (SCM-1b), BLRI (MDR15), CCBP2 (D6/JAB61), CCR1 (CKRI/HM145), CCR2 (mcp-IRB/RA), CCR3 (CKR3/CMKBR3), CCR4, CCR5 (CMKBR5/ChemR13), CCR6 (CMKBR6/CKR-L3/STRL22DRY6), CCR7 (CKR7/EBII), CCR8 (CMKBR8/TERI/CKR-LI), CCR9 (GPR-9-6), CCRLI (VSHKI), CCRL2 (L-CCR), XCRI (GPR5/CCXCRI), CMKLRI, CMKORI (RDCI), CX3CR1 (V28), CXCR4, GPR2 (CCRIO), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCPIO, CKLFSF2, CKLFSF3, CKLFSF4, CKLFSF5, CKLFSF6, CKLFSF7, CKLFSF8, BDNF, C5R1, CSF3, GRCCIO (CIO), EPO, FY (DARC), GDF5, HDFIA, DL8, PRL, RGS3, RGS13, SDF2, SLIT2, TLR2, TLR4, TREMI, TREM2, VHL, ABCFI; ACVRI; ACVRIB; ACVR2; ACVR2B; ACVRLI; AD0RA2A; Aggrecan; AGR2; AICDA; AIFI; AIGI; AKAPI; AKAP2; AMH; AMHR2; ANGPTI; ANGPT2; ANGPTL3; ANGPTL4; ANPEP; APC; APOCI; AR; AZGPI (zinc-a-glycoprotein), B7.1; B7.2; BAD; BAFF (BLys); BAGI; BAH; BCL2; BCL6; BDNF; BLNK; BLRI (MDR15); BMPI; BMP2; BMP3B (GDFIO); BMP4; BMP6; BMP8; BMPRIA; BMPRIB; BMPR2; BPAGI (plectin); BRCAI; C19orfIO (IL27w); C3; C4A; C5; C5R1; CANTI; CASP1; CASP4; CAVI; CCBP2 (D6/JAB61); CCLI (1-309); CCLII (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MTP-2); SLC; exodus-2; CCL22 (MDC/STC-I); CCL23 (MPIF-1); CCL24 (MPIF-2/eotaxin-2); CCL25 (TECK); CCL26 (eotaxin-3); CCL27 (CTACK/ILC); CCL28; CCL3 (MTP-1a); CCL4 (MDP-1b); CCL5 (RANTES); CCL7 (MCP-3); CCL8 (mcp-2); CCNAI; CCNA2; CCNDI; CCNEI; CCNE2; CCRI (CKRI/HM145); CCR2 (mcp-IRB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBII); CCR8 (CMKBR8/TERI/CKR-LI); CCR9 (GPR-9-6); CCRLI (VSHKI); CCRL2 (L-CCR); CD164; CD19; CDIC; CD20; CD200; CD22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDHI (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wap1/Cip1); CDKNIB (p27Kip1); CDKNIC; CDKN2A (P16INK4a); CDKN2B; CDKN2C; CDKN3; CEBPB; CERI; CHGA; CHGB; Chitinase; CHST10; CKLFST2; CKLFSF3; CKLFS4; CKLFSF5; CKLFSF6; CKLFSF7; CKLFSF8; CLDN3; CLDN7 (claudin-7); CLN3; CLU (clusterin); CMKLRI; CMKORI (RDCI); CNRI; COL18A1 COLIAI; COL4A3; COL6A1; CR2; CRP; CSFI (M-CSF); CSF2 (GM-CSE); CSF3 (GCSF); CTLA4; CTNNBI (b-catenin); CTSB (cathepsin B); CX3CL1 (SCYDI); CX3CR1 (V28); CXCLI (GROI); CYCL10 (IP-10); CXCLII (1-TAC/IP-9); CXCL12 (SDFI); CXCL13; CXCL14; CXCL16; CXCL2, (GR02); CXCL3 (GR03); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYCI; CYSLTRI; DAB2IP; DES; DKFZp451 J01 18; DNCLI; DPP4; E2F1; ECGFI; EDGI; EFNAI; EFNA3; EFNB2; EGF; EGFR; ELAC2; ENG; EN01; EN02; EN03; EPHB4; EPO; ERBB2 (Her-2); EREG; ERK8; ESRI; ESR2; F3 (TF); FADD; FasL; FASN; FCERIA; FCER2; FCGR3A; FGF; FGFI (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FELI (EPSILON); FILI (ZETA); FLJ12584; FLJ25530; FLRTI (fibronectin); FLTI; FOS; FOSLI (FRA-I); FY (DARC); GABRP (GABAa); GAGEBI; GAGECI; GALNAC4S-6ST; GAT A3; GDF5; GFI1; GGT1; GM-CSF; GNASI; GNRHI; GPR2 (CCRIO); GPR31; GPR44; GPR81 (FKSG80); GRCCIO (CIO); GRP; GSN (Gelsolin); GSTPI; HAVCR2; HDAC4; HDAC5; HDAC7A; HDAC9; HGF; HIFIA; HDPI; histamine and histamine receptors; HLA-A; HLA-DRA; HM74; HMOXI; HUMCYT2A; ICEBERG; ICOSL; ID2; IFN-a; IFNAI; IFNA2; IFNA4; IFNA5; IFNA6; IFNA7; IFNB1; IFNgannna; DFNWI; IGBPI; IGFI; IGFIR; IGF2; IGFBP2; IGFBP3; IGFBP6; IL-1; IL10; MORA; IL10RB; IL11; IL1 1 RA; IL-12; IL12A; IL12B; IL12RB1;

IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; ILIF10; IL1 F5; IL1 F6; IL1 F7; IL1 F8; IL1 F9; IL1 HYI; IL1 R1; IL1 R2; IL1 RAP; IL1 RAPL1; IL1 RAPL2; IL1 RL1; IL1 RL2, ILIRN; IL2; IL20; IL20RA; IL21 R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAKI; ERAK2; ITGAI; ITGA2; ITGA3; ITGA6 (a6 integrin); ITGAV; ITGB3; ITGB4 (b 4 integrin); JAGI; JAKI; JAK3; JUN; K6HF; KAN; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIBI; midkine; MEF; MIP-2; MKI67; (Ki-67); MMP2; MMP9; MS4A1; MSMB; MT3 (metallothionectin-III); MTSSI; MUCI (mucin); MYC; MYD88; NCK2; neurocan; NFKBI; NFKB2; NGFB (NGF); NGFR; NgR-Lingo; NgR-Nogo66 (Nogo); NgR-p75; NgR-Troy; NMEI (NM23A); N0X5; NPPB; NROBI; NROB2; NRIDI; NR1 D2; NR1 H2; NR1 H3; NR1 H4; NR1 I2; NR1 I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRPI; NRP2; NT5E; NTN4; ODZI; OPRDI; P2RX7; PAP; PARTI; PATE; PAWR; PCA3; PCNA; PDGFA; PDGFB; PECAMI; PF4 (CXCL4); PGF; PGR; phosphacan; PIAS2; PIK3CG; PLAU (uPA); PLG; PLXDCI; PPBP (CXCL7); PPM; PRI; PRKCQ; PRKDI; PRL; PROC; PROK2; PSAP; PSCA; PTAFR; PTEN; PTGS2 (COX-2); PTN; RAC2 (p21 Rac2); RARB; RGSI; RGS13; RGS3; RNFIIO (ZNF144); ROB02; S100A2; SCGB1 D2 (lipophilin B); SCGB2A1 (mammaglobin2); SCGB2A2 (mammaglobin 1); SCYEI (endothelial Monocyte-activating cytokine); SDF2; SERPINAI; SERPINA3; SERP1 NB5 (maspin); SERPINE1 (PAI-I); SERPDMF1; SHBG; SLA2; SLC2A2; SLC33A1; SLC43A1; SLIT2; SPPI; SPRRIB (Sprl); ST6GAL1; STABI; STAT6; STEAP; STEAP2; TB4R2; TBX21; TCPIO; TDGFI; TEK; TGFA; TGFBI; TGFBIII; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor; TLRIO; TLR2; TLR3; TLR4; TLR5; TLR6; TLR7; TLR8; TLR9; TNF; TNF-a; TNFAEP2 (B94); TNFAIP3; TNFRSFIIA; TNFRSFIA; TNFRSFIB; TNFRSF21; TNFRSF5; TNFRSF6 (Fas); TNFRSF7; TNFRSF8; TNFRSF9; TNFSFIO (TRAIL); TNFSF11 (TRANCE); TNFSF12 (AP03L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1 BB ligand); TOLLIP; Toll-like receptors; TOP2A (topoisomerase Ea); TP53; TPMI; TPM2; TRADD; TRAFI; TRAF2; TRAF3; TRAF4; TRAF5; TRAF6; TREMI; TREM2; TRPC6; TSLP; TWEAK; VEGF; VEGFB; VEGFC; versican; VHL C5; VLA-4; XCLI (lymphotactin); XCL2 (SCM-1b); XCRI (GPR5/CCXCRI); YYI; and ZFPM2.

In some embodiments, targets include CD proteins such as CD3, CD4, CD8, CD16, CD19, CD20, CD34; CD64, CD200 members of the ErbB receptor family such as the EGF receptor, HER2, HER3 or HER4 receptor; cell adhesion molecules such as LFA-1, Mad, p150.95, VLA-4, ICAM-1, VCAM, alpha4/beta7 integrin, and alphav/beta3 integrin including either alpha or beta subunits thereof (e.g., anti-CD11a, anti-CD18 or anti-CD11b antibodies); growth factors such as VEGF-A, VEGF-C; tissue factor (TF); alpha interferon (alphaIFN); TNFalpha, an interleukin, such as IL-1 beta, IL-3, IL-4, IL-5, IL-8, IL-9, IL-13, IL17A/F, IL-18, IL-13Ralpha1, IL13Ralpha2, IL-4R, IL-5R, IL-9R, IgE; blood group antigens; flk2/flt3 receptor; obesity (OB) receptor; mpl receptor; CTLA-4; RANKL, RANK, RSV F protein, protein C etc., low-density lipoprotein receptor-related protein (LRP)-1 or LRP-8 or transferrin receptor, and at least one target selected from the group consisting of 1) beta-secretase (BACE1 or BACE2), 2) alpha-secretase, 3) gamma-secretase, 4) tau-secretase, 5) amyloid precursor protein (APP), 6) death receptor 6 (DR6), 7) amyloid beta peptide, 8) alpha-synuclein, 9) Parkin, 10) Huntingtin, 11) p75 NTR, and 12) caspase-6.

It is understood that the antibody (e.g., multispecific antibody, e.g., bispecific antibody) may bind at least two target molecules, for example, at least two target molecules selected from the group consisting of: IL-1 alpha and IL-1 beta, IL-12 and IL-18; IL-13 and IL-9; IL-13 and IL-4; IL-13 and IL-5; IL-5 and IL-4; IL-13 and IL-1 beta; IL-13 and IL-25; IL-13 and TARC; IL-13 and MDC; IL-13 and MEF; IL-13 and TGF-β; IL-13 and LHR agonist; IL-12 and TWEAK, IL-13 and CL25; IL-13 and SPRR2a; IL-13 and SPRR2b; IL-13 and ADAM8, IL-13 and PED2, IL17A and IL17F, CD3 and CD19, CD138 and CD20; CD138 and CD40, CD19 and CD20; CD20 and CD3; CD38 and CD138, CD38 and CD20; CD38 and CD40; CD40 and CD20; CD-8 and IL-6; CD20 and BR3, TNFalpha and TGF-beta, TNFalpha and IL-1 beta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-11, TNFalpha and IL-12, TNFalpha and IL-13, TNFalpha and IL-14, TNFalpha and IL-15, TNFalpha and IL-16, TNFalpha and IL-17, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFa and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET, VEGFR and MET receptor, VEGFR and EGFR, HER2 and CD64, HER2 and CD3, HER2 and CD16, HER2 and HER3; EGFR(HER1) and HER2, EGFR and HER3, EGFR and HER4, IL-13 and CD40L, IL4 and CD40L, TNFR1 and IL-1 R, TNFR1 and IL-6R and TNFR1 and IL-18R, EpCAM and CD3, MAPG and CD28, EGFR and CD64, CSPGs and RGM A; CTLA-4 and BTN02; IGF1 and IGF2; IGF1/2 and Erb2B; MAG and RGM A; NgR and RGM A; NogoA and RGM A; OMGp and RGM A; PDL-1 and CTLA-4; and RGM A and RGM B.

In some embodiments, the target is anti-VEGF, anti-c-met, anti-IgE, anti-CD11, anti-CD18, anti-CD40, anti-tissue factor (TF), anti-HER2, and anti-TrkC antibodies. Antibodies directed against non-polypeptide antigens (such as tumor-associated glycolipid antigens) are also contemplated. Additional exemplary targets for antibodies encompassed by the present invention include CD proteins such as CD3, CD4, CD8, CD19, CD20, CD34, and CD46; members of the ErbB receptor family such as the EGF receptor, HER2, HER3 or HER4 receptor; cell adhesion molecules such as LFA-1, Mac1, p150.95, VLA-4, ICAM-1, VCAM, α4/β7 integrin, and αv/β3 integrin including either α or β subunits thereof (e.g. anti-CD11a, anti-CD18 or anti-CD11b antibodies); growth factors such as VEGF; tissue factor (TF); TGF-β, alpha interferon (α-IFN); an interleukin, such as IL-8; IgE; blood group antigens Apo2, death receptor; flk2/flt3 receptor; obesity (OB) receptor; mpl receptor; CTLA-4; protein C etc. Bi-specific antibodies are expressly contemplated by the invention.

In one embodiment, the antibody(ies), e.g. the antibody (ies) used in the methods herein may incorporate any of the features, singly or in combination, as described in Sections 1-6 below:

1. Antibody Fragments

In certain embodiments, an antibody provided herein is an antibody fragment. Antibody fragments include, but are not limited to, Fab, Fab', Fab'-SH, F(ab')2, Fv, and scFv fragments, a one-armed antibody, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

One-armed antibodies (i.e., the heavy chain variable domain and the light chain variable domain form a single antigen binding arm) are disclosed in, for example, WO2005/063816; Martens et al, Clin Cancer Res (2006), 12: 6144. For treatment of pathological conditions requiring an antagonistic function, and where bivalency of an antibody results in an undesirable agonistic effect, the monovalent trait of a one-armed antibody (i.e., an antibody comprising a single antigen binding arm) results in and/or ensures an antagonistic function upon binding of the antibody to a target molecule. Furthermore, the one-armed antibody comprising a Fc region is characterized by superior pharmacokinetic attributes (such as an enhanced half life and/or reduced clearance rate in vivo) compared to Fab forms having similar/substantially identical antigen binding characteristics, thus overcoming a major drawback in the use of conventional monovalent Fab antibodies. Techniques for making one-armed antibodies include, but are not limited to, "knob-in-hole" engineering (see, e.g., U.S. Pat. No. 5,731,168). Onartuzumab is an example of a one-armed antibody.

Antibody fragments can be made by various techniques, including but not limited to proteolytic digestion of an intact antibody as well as production by recombinant host cells (e.g. *E. coli* or phage), as described herein.

2. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HSR residues are derived), e.g., to restore or improve antibody specificity or affinity.

Humanized antibodies and methods of making them are reviewed, e.g., in Almagro and Fransson, Front. Biosci. 13:161.9-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260(2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

3. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,871) describing K-M MOUSE® technology, and U.S. Patent Application Publication No. US 2007/0061900, describing Veloci-Mouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

4. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

5. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for c-met and the other is for any other antigen. In certain embodiments, bispecific antibodies may bind to two different epitopes of c-met. Bispecific antibodies may also be used to localize cytotoxic agents to cells which express c-met. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, Kostelny et al., J. Immunol., 148(5):1547-1553 (1992)); using "diabody" technology for making bispecific antibody fragments (see, e.g., Hollinger et al., Proc. Natl. Acad., Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to c-met as well as another, different antigen, such as EGFR (see, US 2008/0069820, for example).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low.

Similar procedures are disclosed in WO 93/08829 published May 13, 1993, and in Traunecker et al., *EMBO J.*, 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan) (knobs or protuberances). Compensatory "cavities" (holes) of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. Knobs and holes are further described herein.

6. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the HVRs and FRs. Amino acid substitutions may be introduced into an antibody of interest and the products screened for a desired activity, e.g., retained/improved antigen binding, decreased immunogenicity, or improved ADCC or CDC.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glyeostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Knobs in Holes

The use of knobs into holes as a method of producing multispecific antibodies and/or one-armed antibodies and/or immunoadhesins is well known in the art. See U.S. Pat. No. 5,731,168 granted 24 Mar. 1998 assigned to Genentech, PCT Pub. No. WO2009089004 published 16 Jul. 2009 and assigned to Amgen, and US Pat. Pub. No. 20090182127 published 16 Jul. 2009 and assigned to Novo Nordisk A/S. See also Marvin and Zhu, Acta Pharmacologica Sincia (2005) 26(6):649-658 and Kontermann (2005) Acta Pharacol. Sin., 26:1-9. A brief discussion is provided here.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide. The side chain volumes of the various amino residues are shown in the following table.

TABLE B

Properties of Amino Acid Residues

| Amino Acid | One-Letter Abbreviation | MASS[a] (daltons) | VOLUME[b] (Angstrom$^3$) | Accessible Surface Area[c] (Angstrom$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalinine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight amino acid minus that of water. Values from *Handbook of Chemistry and Physics*, 43rd ed. Cleveland, Chemical Rubber Publishing Co., 1961.
[b]Values from A. A. Zamyatnin, *Prog. Biophys. Mol. Biol.* 24: 107-123, 1972.
[c]Values from C. Chothia, *J. Mol. Biol.* 105: 1-14, 1975. The accessible surface area is defined in FIGS. 6-20 of this reference.

The preferred import residues for the formation of a protuberance are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the protuberance has a small side chain volume, such as alanine, asparagine, aspartic acid, glycine, serine, threonine or valine. Exemplary amino acid substitutions in the CH3 domain for forming the protuberance include without limitation the T366W substitution.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The side chain volumes of the various amino residues are shown in Table B above. The preferred import residues for the formation of a cavity are usually naturally occurring amino acid residues and are preferably selected from alanine (A), serine (S), threonine (T) and valine (V). Most preferred are serine, alanine or threonine. In one embodiment, the original residue for the formation of the cavity has a large side chain volume, such as tyrosine, arginine, phenylalanine or tryptophan. Exemplary amino acid substitutions in the CH3 domain for generating the cavity include without limitation the T366S, L368A and Y407A substitutions.

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table B above. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., *Meth. Enzymol.* 202:301-336 (1991), for example. To generate such non-naturally occurring amino acid residues, the procedures of Noren et al. *Science* 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. Typically, original residues for replacement are "buried". By "buried" is meant that the residue is essentially inaccessible to solvent. Generally, the import residue is not cysteine to prevent possible oxidation or mispairing of disulfide bonds.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

By "original or template nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in *Mutagenesis: a Practical Approach*. M. J. McPherson, Ed., (IRL Press, Oxford, UK. (1991), and include site-directed mutagenesis, cassette mutagenesis and polymerase chain reaction (PCR) mutagenesis, for example. By mutating an original/template nucleic acid, an original/template polypeptide encoded by the original/template nucleic acid is thus correspondingly altered.

The protuberance or cavity can be "introduced" into the interface of a first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. Accordingly, the protuberance or cavity which is "introduced" is "non-naturally occurring" or "non-native", which means that it does not exist in nature or in the original polypeptide (e.g. a humanized monoclonal antibody).

Generally, the import amino acid residue for forming the protuberance has a relatively small number of "rotamers" (e.g. about 3-6). A "rotamer" is an energetically favorable conformation of an amino acid side chain. The number of rotamers of the various amino acid residues are reviewed in Ponders and Richards, *J. Mol. Biol.* 193: 775-791 (1987).

In one embodiment, a first Fc polypeptide and a second Fc polypeptide meet/interact at an interface. In some embodiments wherein the first and second Fc polypeptides meet at an interface, the interface of the second Fc polypeptide (sequence) comprises a protuberance (also termed a "knob") which is positionable in a cavity (also termed a "hole") in the interface of the first Fc polypeptide (sequence). In one embodiment, the first Fc polypeptide has been altered from a template/original polypeptide to encode the cavity or the second Fc polypeptide has been altered from a template/original polypeptide to encode the protuberance, or both. In one embodiment, the first Fc polypeptide has been altered from a template/original polypeptide to encode the cavity and the second Fc polypeptide has been altered from a template/original polypeptide to encode the protuberance. In one embodiment, the interface of the second Fc polypeptide comprises a protuberance which is positionable in a cavity in the interface of the first Fc polypeptide, wherein the cavity or protuberance, or both, have been introduced into the interface of the first and second Fc polypeptides, respectively. In some embodiments wherein the first and second Fc polypeptides meet at an interface, the interface of the first Fc polypeptide (sequence) comprises a protuberance which is positionable in a cavity in the interface of the second Fc polypeptide (sequence). In one embodiment, the second Fc polypeptide has been altered from a template/original polypeptide to encode the cavity or the first Fc polypeptide has been altered from a template/original polypeptide to encode the protuberance, or both. In one embodiment, the second Fc polypeptide has been altered from a template/original polypeptide to encode the cavity and the first Fc polypeptide has been altered from a template/original polypeptide to encode the protuberance. In one embodiment, the interface of the first Fc polypeptide comprises a protuberance which is positionable in a cavity in the interface of the second Fc polypeptide, wherein the protuberance or cavity, or both, have been introduced into the interface of the first and second Fc polypeptides, respectively.

In one embodiment, the protuberance and cavity each comprise a naturally occurring amino acid residue. In one embodiment, the Fc polypeptide comprising the protuberance is generated by replacing an original residue from the interface of a template/original polypeptide with an import residue having a larger side chain volume than the original residue. In one embodiment, the Fc polypeptide comprising the protuberance is generated by a method comprising a step wherein polynucleotide encoding an original residue from the interface of said polypeptide is replaced with polynucleotide encoding an import residue having a larger side chain volume than the original. In one embodiment, the original residue is threonine. In one embodiment, the original residue is T366. In one embodiment, the import residue is arginine (R). In one embodiment, the import residue is phenylalanine (F). In one embodiment, the import residue is tyrosine (Y). In one embodiment, the import residue is tryptophan (W). In one embodiment, the import residue is R, F, Y or W. In one embodiment, a protuberance is generated by replacing two or more residues in a template/original polypeptide. In one embodiment, the Fc polypeptide comprising a protuberance comprises replacement of threonine at position 366 with tryptophan, amino acid numbering according to the EU numbering scheme of Kabat et al. (pp. 688-696 in Sequences of proteins of immunological interest, 5th ed., Vol. 1 (1991; NIH, Bethesda, Md.)).

In some embodiments, the Fc polypeptide comprising a cavity is generated by replacing an original residue in the interface of a template/original polypeptide with an import residue having a smaller side chain volume than the original residue. For example, the Fc polypeptide comprising the cavity may be generated by a method comprising a step wherein polynucleotide encoding an original residue from the interface of said polypeptide is replaced with polynucleotide encoding an import residue having a smaller side chain volume than the original. In one embodiment, the original residue is threonine. In one embodiment, the original residue is leucine. In one embodiment, the original residue is tyrosine. In one embodiment, the import residue is not cysteine (C). In one embodiment, the import residue is alanine (A). In one embodiment, the import residue is serine (S). In one embodiment, the import residue is threonine (T). In one embodiment, the import residue is valine (V). A cavity can be generated by replacing one or more original residues of a template/original polypeptide. For example, in one embodiment, the Fc polypeptide comprising a cavity comprises replacement of two or more original amino acids selected from the group consisting of threonine, leucine and tyrosine. In one embodiment, the Fc polypeptide comprising a cavity comprises two or more import residues selected from the group consisting of alanine, serine, threonine and valine. In some embodiments, the Fc polypeptide comprising a cavity comprises replacement of two or more original amino acids selected from the group consisting of threonine, leucine and tyrosine, and wherein said original amino acids are replaced with import residues selected from the group consisting of alanine, serine, threonine and valine. In some embodiments, an original amino acid that is replaced is T366, L368 and/or Y407. In one embodiment, the Fc polypeptide comprising a cavity comprises replacement of threonine at position 366 with serine, amino acid numbering according to the EU numbering scheme of Kabat et al. supra. In one embodiment, the Fc polypeptide comprising a cavity comprises replacement of leucine at position 368 with alanine, amino acid numbering according to the EU numbering scheme of Kabat et al. supra. In one embodiment, the Fc polypeptide comprising a cavity comprises replacement of tyrosine at position 407 with valine, amino acid numbering according to the EU numbering scheme of Kabat et al. supra. In one embodiment, the Fc polypeptide comprising a cavity comprises two or more amino acid replacements selected from the group consisting of T366S, L368A and Y407V, amino acid numbering according to the EU numbering scheme of Kabat et al. supra. In some embodiments of these antibody fragments, the Fc polypeptide comprising the protuberance comprises replacement of threonine at position 366 with tryptophan, amino acid numbering according to the EU numbering scheme of Kabat et al. supra.

In one embodiment, the antibody comprises Fc mutations constituting "knobs" and "holes" as described in WO2005/063816. For example, a hole mutation can be one or more of T366A, L368A and/or Y407V in an Fc polypeptide, and a knob mutation can be T366W.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In one embodiment, the medicament is an immunoconjugate comprising an antibody (such as a c-met antibody) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At211, I131, I125, Y90, Re186, Re188, Sm153, Bi212, P32, Pb212 and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediainine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Vectors, Host Cells, and Recombinant Methods

For recombinant production of a heterologous polypeptide (e.g, an antibody), the nucleic acid encoding it is isolated and inserted into a replicable vector for further cloning (amplification of the DNA) or for expression. DNA encoding the polypeptide (eg, antibody) is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
i. Vector Construction

Polynucleotide sequences encoding polypeptide components of the polypeptide (e.g., antibody) of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-lactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) Cell 20: 269) using linkers or adaptors to supply any required restriction sites.

The translational initiation region (TIR) is a major determinant of the overall translation level of a protein. The TIR includes the polynucleotide that encodes the signal sequence, and extends from immediately upstream of the Shine-Delgarno sequence to approximately twenty nucleotides downstream of the initiation codon. Generally, the vector will comprise a TIR, TIRs and variant TIRs are known in the art and methods for generating TIRs are known in the art A series of nucleic acid sequence variants can be created with a range of translational strengths, thereby providing a convenient means by which to adjust this factor for the optimal secretion of many different polypeptides. The use of a reporter gene fused to these variants, such as PhoA, provides a method to quantitate the relative translational strengths of different translation initiation regions. The variant or mutant TIRs can be provided in the background of a plasmid vector thereby providing a set of plasmids into which a gene of interest may be inserted and its expression measured, so as to establish an optimum range of translational strengths for maximal expression of mature polypeptide. Variant TIRs are disclosed in U.S. Pat. No. 8,241,901.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the signal polypeptides of the present invention. In addition, the vector may comprise a signal sequence selected from the group consisting of alkaline phosphatase, penicillinase, Lpp, or heat-stable enterotoxin II (STII) leaders, LamB, PhoE, PelB, OmpA, and MBP.

In one aspect, one or more polynucleotides (e.g., expression vectors) collectively encode an antibody. In one embodiment, a single polynucleotide encodes the light chain of the antibody and a separate polynucleotide encodes the heavy chain of the antibody. In one embodiment, a single polynucleotide encodes the light chain and heavy chain of the antibody. In some embodiments, one or more polynucleotides (e.g., expression vectors) collectively encode a one-aimed antibody. In one embodiment, a single polynucleotide encodes (a) the light and heavy chain of the one armed antibody, and (b) the Fc polypeptide. In one embodiment, a single polynucleotide encodes the light and heavy chain of the one armed antibody, and a separate, polynucleotide encodes the Fc polypeptide. In one embodiment, separate polynucleotides encode the light chain component of the one-armed antibody, the heavy chain component of the one-armed antibody and the Fc polypeptide, respectively. Production of a one-armed antibody is described in, for example, in WO2005063816.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635) and strains 63C1, 66F8 and 64B4. Other strains and derivatives thereof, such as *E. coli* 294 (ATCC 31,446), *E. coli* B, *E. coli* λ1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147) or media described in WO2002/061090. A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210. In some embodiments, DsbA and C are expressed (e.g., over-expressed) in the bacterial host cell. In some embodiments, DsbA, DsbC and FkpA are expressed (e.g., overexpressed) in the bacterial host cell.

To minimize proteolysis of expressed heterologous proteins (especially those that are proteolytically sensitive), certain host strains deficient for proteol enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some E. coli protease-deficient strains are available and described in, for example, Joly et al., (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins and/or FkpA are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from Staphylococcus aureas which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

The invention also provides immunoconjugates (interchangeably termed "antibody-drug conjugates" or "ADC"), comprising any of the antibodies described herein conjugated to, e.g., a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

Uses

A heterologous polypeptide may be used, for example, to purify, detect, and target a specific polypeptide it recognizes, including both in vitro and in vivo diagnostic and therapeutic methods.

In one aspect, an antibody of the invention can be used in immunoassays for qualitatively and quantitatively measuring specific antigens in biological samples. Conventional methods for detecting antigen-antibody binding includes, for example, an enzyme linked immunosorbent assay (ELISA), an radioimmunoassay (RIA) or tissue immunohistochemistry. Many methods may use a label bound to the antibody for detection purposes. The label used with the antibody is any detectable functionality that does not interfere with its binding to antibody. Numerous labels are known, including the radioisotopes $^{32}P$, $^{35}S$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, .beta.-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, lactoperoxidase, biotin/avidin, spin labels, bacteriophage labels, stable free radicals, imaging radionuclides (such as Technecium) and the like.

Conventional methods are available to bind these labels covalently to the heterologous polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al. Nature 144: 945 (1962); David et al. Biochemistry 13:1014-1021 (1974); Pain et al. J. Immunol. Methods 40:219-230 (1981); and Nygren Histochem. and Cytochem 30:407-412 (1982). Preferred labels herein are enzymes such as horseradish peroxidase and alkaline phosphatase. The conjugation of such label, including the enzymes, to the antibody polypeptide is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Such bonding methods are suitable for use with the heterologous polypeptides of this invention.

Alternative to labeling the heterologous polypeptide, antigen can be assayed in biological fluids by a competition immunoassay utilizing a competing antigen standard labeled with a detectable substance and an unlabeled heterologous polypeptide. In this assay, the biological sample, the labeled antigen standards and the heterologous polypeptide are combined and the amount of labeled antigen standard bound to the unlabeled heterologous polypeptide is determined. The amount of tested antigen in the biological sample is inversely proportional to the amount of labeled antigen standard bound to the heterologous polypeptide.

In one aspect, a heterologous polypeptide (such as an antibody) is particularly useful to detect and profile expressions of specific surface antigens in vitro or in vivo. As discussed before, generally, an aglycosylated antibody does not exert effector functions (i.e., ADCC or CDC activity). Therefore, when the antibody binds to the cell surface antigen, it will not initiate undesirable cytotoxic events. The surface antigen can be specific to a particular cell or tissue type, therefore serving as a marker of the cell or tissue type. Preferably, the surface antigen marker is differentially expressed at various differentiation stages of particular cell or tissue types. The antibody directed against such surface antigen can thus be used for the screening of cell or tissue populations expressing the marker. For example, the antibody can be used for the screening and isolation of stem cells such as embryonic stem cells, hematopoietic stem cells and mesenchymal stem cells. The antibody can also be used to detect tumor cells expressing tumor-associated surface antigens such c-met, HER2, HER3 or HER4 receptors.

An antibody or other heterologous polypeptide may be used as an affinity purification agent. In this process, the polypeptide is immobilized on a solid phase such a Sephadex resin or filter paper, using methods well known in the art. The immobilized polypeptide is contacted with a sample containing the antigen to be purified, and thereafter the support is washed with a suitable solvent that will remove substantially all the material in the sample except the antigen to be purified, which is bound to the immobilized polypeptide. Finally, the support is washed with another suitable solvent, such as glycine buffer, pH 5.0, that will release the antigen from the polypeptide.

In one aspect, the invention provides uses of a heterologous polypeptide generated using the methods of the invention, in the preparation of a medicament for the therapeutic and/or prophylactic treatment of a disease, such as a cancer, a tumor, a cell proliferative disorder, and/or an immune (such as autoimmune) disorder. The heterologous polypeptide can be of any form described herein, including antibody, antibody fragment, polypeptide (e.g., an oligopeptide), or combination thereof. In some embodiments, the antigen is a human protein molecule and the subject is a human subject.

The polypeptides can be used to diagnose, treat, inhibit or prevent diseases, disorders or conditions associated with abnormal expression and or activity of one or more antigen molecules, including but not limited to malignant and benign tumors; non-leukemias and lymphoid malignancies; neuronal, ghat, astrocytal, hypothalamic and other glandular, macrophagal, epithelial, stromal and blastocoelic disorders; and inflammatory, angiogenic and immunologic disorders.

In certain embodiments, a protein (e.g., an antibody) is administered to a subject. In certain embodiments, an immunoconjugate comprising the antibody is administered to a subject. Preferably, the immunoconjugate and/or antigen to which it is bound is/are internalized by the cell.

Heterologous polypeptides can be used either alone or in combination with other compositions in a therapy. For instance, the heterologous polypeptide may be co-administered with an antibody, chemotherapeutic agent(s) (including cocktails of chemotherapeutic agents), other cytotoxic agent(s), anti-angiogenic agent(s), cytokines, and/or growth inhibitory agent(s). Where the heterologous polypeptide inhibits tumor growth, it may be particularly desirable to combine the heterologous polypeptide with one or more other therapeutic agent(s) which also inhibits tumor growth. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody can occur prior to, and/or following, administration of the adjunct therapy or therapies.

The heterologous polypeptide (and optionally, an adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Preferably the dosing is given by injections, most preferably intravenous or subcutaneous injections, depending in part on whether the administration is brief or chronic.

The heterologous polypeptide will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of the antibody (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. The preferred dosage of the antibody will be in the range from about 0.05 mg/kg to about 10 mg/kg. An initial higher loading dose, followed by one or more lower doses may be administered. However, other dosage regimens may be useful. The progress of this therapy is easily monitored by conventional techniques and assays.

Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a antibody of the invention. The label or package insert indicates that the composition is used for treating the condition of choice, such as cancer. Moreover, the article of manufacture may comprise (a) a first container with a composition contained therein, wherein the composition comprises a antibody; and (b) a second container with a composition contained therein, wherein the composition comprises a further cytotoxic agent. The article of manufacture in this embodiment of the invention may further comprise a package insert indicating that the first and second antibody compositions can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are intended merely to illustrate the practice of the present invention and are not provided by way of limitation. The disclosures of all patent and scientific literatures cited herein are expressly incorporated in their entirety by reference.

EXAMPLES

Materials and Methods

Strains and Plasmids. Strains and plasmids used in this study are listed in Table 1. To construct heavy chain-only expression vectors, full-length antibody expression vectors were digested with SpeI and NsiI (New England Biolabs). The resulting fragment containing the signal peptide sequence and heavy chain sequence was cloned into SpeI and NsiI sites of a pBR322-derived cloning vector comprising a truncated light chain fragment (122-237), a phoA promoter fused to a heavy chain sequence, and a lamda $t_0$ transcriptional terminator. Western blot analysis probing with αkLc antibody confirmed that light chain was not expressed with the heavy chain-only vector. To construct PhoA reporter plasmids for translational strength measurement, the signal peptide variant of interest was fused to the phoA gene via regular PCR or splicing overlap extension (SOE) PCR. The resulting fragment was cloned into the SpeI and NotI (New England Biolabs) sites of pPhoA51 [1]. Site-specific mutations in signal peptide sequences were introduced by the QuickChange Site-Directed Mutagenesis Kit (Stratagene).

TABLE 1

Strains and plasmids used in this study

| Strains | Relevant genotypes | References |
|---|---|---|
| 27C7 | W3110 ΔfhuA (ΔtonA) phoAΔE15 Δ(argF-lac)169 ptr3 degP41 kanR ompTΔ(nmpc-fepE) | [1] |
| 64B4 | W3110 ΔfhuA ΔphoA ilvG + Δprc spr43H1 ΔdegP ΔmanA lacIq ΔompT | [2] |
| 5-alpha F'Iq | F' proA + B + lacIq Δ(lacZ)M15 zzf::Tn10 (TetR)/ fhuA2Δ(argF-lacZ)U169 phoA glnV44 Φ80Δ(lacZ)M15 gyrA96 recA1 relA1 endA1 thi-1 hsdR33 | New England Biolab |

| Plasmid | Relevant characteristics | References |
|---|---|---|
| pPhoA51 | E. coli XbaI-ssSTII TIR1 fused to Δ(1-22)PhoA. Cb$^r$ | [1] |
| pPhoA86 | E. coli XbaI-ssSTII TIR1 + fused to Δ(1-22)PhoA. Cb$^r$ | [1] |
| pPhoA41 | E. coli XbaI-ssSTII TIR3 fused to Δ(1-22)PhoA. Cb$^r$ | [1] |
| pBR322 | Cb$^r$, Tc$^r$ | Laboratory stock |
| pBR-bSTII1-PhoA | E. coli BssHII-ssSTII TIR1 fused to Δ(1-22)PhoA. Cb$^r$ | This study |
| pBR-mSTII1-PhoA | E. coli MluI-ssSTII TIR1 fused to Δ(1-22)PhoA. Cb$^r$ | This study |
| pBR-bDsbA1-PhoA | E. coli BssHII-ssDsbA TIR1 fused to Δ(1-22)PhoA. Cb$^r$ | This study |
| pBR-bMalE1-PhoA | E. coli BssHII-ssMalE TIR1 fused to Δ(1-22)PhoA. Cb$^r$ | This study |
| pBR-bPhoA1-PhoA | E. coli BssHII-ssPhoA TIR1 fused to Δ(1-22)PhoA. Cb$^r$ | This study |
| pBR-mMalE1-PhoA | E. coli MluI-ssMalE TIR1 fused to Δ(1-22)PhoA. Cb$^r$ | This study |
| pBR-mPhoA1-PhoA | E. coli MluI-ssPhoA TIR1 fused to Δ(1-22)PhoA. Cb$^r$ | This study |
| pBR-bDsbA1 L11I-PhoA | E. coli BssHII-ssDsbA L11I TIR1 fused to Δ(1-22)PhoA. Cb$^r$ | This study |
| pBR-bDsbA1 L11S-PhoA | E. coli BssHII-ssDsbA L11S TIR1 fused to Δ(1-22)PhoA. Cb$^r$ | This study |
| pBR-bDsbA1 L11A-PhoA | E. coli BssHII-ssDsbA L11A TIR1 fused to Δ(1-22)PhoA. Cb$^r$ | This study |
| pBR-bDsbA1 L11C-PhoA | E. coli BssHII-ssDsbA L11C TIR1 fused to Δ(1-22)PhoA. Cb$^r$ | This study |
| pBR-bDsbA1 L11Y-PhoA | E. coli BssHII-ssDsbA L11Y TIR1 fused to Δ(1-22)PhoA. Cb$^r$ | This study |
| pBR-bDsbA1 L11Q-PhoA | E. coli BssHII-ssDsbA L11Q TIR1 fused to Δ(1-22)PhoA. Cb$^r$ | This study |
| pBR-bDsbA1 L11G codon1-PhoA | E. coli BssHII-ssDsbA L11G codon1 TIR1 fused to Δ(1-22)PhoA. Cb$^r$ | This study |
| pBR-bDsbA1 L11G codon2-PhoA | E. coli BssHII-ssDsbA L11G codon2 TIR1 fused to Δ(1-22)PhoA. Cb$^r$ | This study |

TABLE 1-continued

Strains and plasmids used in this study

| | | |
|---|---|---|
| pBR-bDsbA1 S18Y-PhoA | E. coli BssHII-ssDsbA S18Y TIR1 fused to Δ(1-22)PhoA. Cb$^r$ | This study |
| pBR-bSTII1 S11L codon1-PhoA | E. coli BssHII-ssSTII S11L codon1 TIR1 fused to Δ(1-22)PhoA. Cb$^r$ | This study |
| pBR-bSTII1 S11L (CTC)-PhoA | E. coli BssHII-ssSTII S11L codon2 TIR1 fused to Δ(1-22)PhoA. Cb$^r$ | This study |
| pBR-bSTII1 S11I-PhoA | E. coli BssHII-ssSTII S11I TIR1 fused to Δ(1-22)PhoA. Cb$^r$ | This study |
| pBR-bSTII1 S11A-PhoA | E. coli BssHII-ssSTII S11A TIR1 fused to Δ(1-22)PhoA. Cb$^r$ | This study |
| pBR-bSTII1 S11C-PhoA | E. coli BssHII-ssSTII S11C TIR1 fused to Δ(1-22)PhoA. Cb$^r$ | This study |
| pBR-bSTII1 S11Y-PhoA | E. coli BssHII-ssSTII S11Y TIR1 fused to Δ(1-22)PhoA. Cb$^r$ | This study |
| pBR-bSTII1 S11Y-PhoA | E. coli BssHII-ssSTII S11Y TIR1 fused to Δ(1-22)PhoA. Cb$^r$ | This study |
| pBR-bSTII1 S11Q-PhoA | E. coli BssHII-ssSTII S11Q TIR1 fused to Δ(1-22)PhoA. Cb$^r$ | This study |
| pBR-bSTII1 S11G-PhoA | E. coli BssHII-ssSTII S11G TIR1 fused to Δ(1-22)PhoA. Cb$^r$ | This study |
| pBR-bSTII1 Y22S-PhoA | E. coli BssHII-ssSTII Y22S TIR1 fused to Δ(1-22)PhoA. Cb$^r$ | This study |
| pBR-mSTII1-bSTII1-5D5 | MluI-STII TIR1 fused to 5D5Lc, BssHII-STII TIR1 fused to 5D5Hc | [3] |
| pBR-mSTII1-bDsbA1-5D5 | MluI-STII TIR1 fused to 5D5Lc, BssHII-DsbA TIR1 fused to 5D5Hc | [3] |
| pBR-mSTII1-bMalE1-5D5 | MluI-STII TIR1 fused to 5D5Lc, BssHII-MalE TIR1 fused to 5D5Hc | [3] |
| pBR-mSTII1-bPhoA1-5D5 | MluI-STII TIR1 fused to 5D5Lc, BssHII-PhoA TIR1 fused to 5D5Hc | [3] |
| pBR-mSTII1-mPhoA1-5D5 | MluI-STII TIR1 fused to 5D5Lc, MluI-PhoA TIR1 fused to 5D5Hc | This study |
| pBR-mSTII1-mMalE1-5D5 | MluI-STII TIR1 fused to 5D5Lc, MluI-MalE TIR1 fused to 5D5Hc | This study |
| pBR-mSTII1-bDsbA1 L11I-5D5 | MluI-STII TIR1 fused to 5D5Lc, BssHII-DsbA L11I TIR1 fused to 5D5Hc | This study |
| pBR-mSTII1-bDsbA1 L11S-5D5 | MluI-STII TIR1 fused to 5D5Lc, BssHII-DsbA L11S TIR1 fused to 5D5Hc | This study |
| pBR-mSTII1-bDsA1 S18Y-5D5 | MluI-STII TIR1 fused to 5D5Lc, BssHII-STII S18Y TIR1 fused to 5D5Hc | This study |
| pBR-mSTII1-bSTII1 S11L codon1-5D5 | MluI-STII TIR1 fused to 5D5Lc, BssHII-STII S11L codon1 TIR1 fused to 5D5Hc | This study |
| pBR-mSTII1-bSTII1 S11L codon2-5D5 | MluI-STII TIR1 fused to 5D5Lc, BssHII-STII S11L codon2 TIR1 fused to 5D5Hc | This study |
| pBR-mSTII1-bSTII1 S11I-5D5 | MluI-STII TIR1 fused to 5D5Lc, BssHII-STII S11I TIR1 fused to 5D5Hc | This study |
| pBR-mSTII1-bSTII1 Y22S-5D5 | MluI-STII TIR1 fused to 5D5Lc, BssHII-STII Y22S TIR1 fused to 5D5Hc | This study |
| pBR-xSTII1 + -xSTII1 + -5D5 | XbaI-STII TIR1 + fused to 5D5Lc, XbaI STII TIR1 + fused to 5D5Hc | This study |
| pBR-xSTII1 + -bDsbA1-5D5 | XbaI-STII TIR1 + fused to 5D5Lc, BssHII-DsbA TIR1 fused to 5D5Hc | This study |
| pBR-xSTII1-5D5HC | XbaI-STII TIR1 fused to 5D5Hc | This study |
| pBR-xSTII1 + -5D5HC | XbaI-STII TIR1 + fused to 5D5Hc | This study |
| pBR-bSTII1-5D5HC | BssHII-STII TIR1 fused to 5D5Hc | This study |
| pBR-bDsbA1-5D5HC | BssHII-DsbA TIR1 fused to 5D5Hc | This study |
| pBR-bMalE1-5D5HC | BssHII-MalE TIR1 fused to 5D5Hc | This study |
| pBR-bPhoA1-5D5HC | BssHII-PhoA TIR1 fused to 5D5Hc | This study |
| pBR-mMalE1-5D5HC | MluI-MalE TIR1 fused to 5D5Hc | This study |
| pBR-mPhoA1-5D5HC | MluI-PhoA TIR1 fused to 5D5Hc | This study |
| pBR-bSTII1 S11L codon1-5D5HC | BssHII-STII S11L codon1 TIR1 fused to 5D5Hc | This study |
| pBR-bSTII1 S11L codon2-5D5HC | BssHII-STII S11L codon2 TIR1 fused to 5D5Hc | This study |
| pBR-bSTII1 S11I-5D5HC | BssHII-STII S11I TIR1 fused to 5D5Hc | This study |
| pBR-bSTII1 S11A-5D5HC | BssHII-STII S11A TIR1 fused to 5D5Hc | This study |
| pBR-bSTII1 S11C-5D5HC | BssHII-STII S11C TIR1 fused to 5D5Hc | This study |
| pBR-bSTII1 S11Y codon1-5D5HC | BssHII-STII S11Y codon1 TIR1 fused to 5D5Hc | This study |
| pBR-bSTII1 S11Y codon2-5D5HC | BssHII-STII S11Y codon2 TIR1 fused to 5D5Hc | This study |
| pBR-bSTII1 S11Q-5D5HC | BssHII-STII S11Q TIR1 fused to 5D5Hc | This study |
| pBR-bSTII1 S11G-5D5HC | BssHII-STII S11G TIR1 fused to 5D5Hc | This study |

TABLE 1-continued

Strains and plasmids used in this study

| | | |
|---|---|---|
| pBR-bSTII1 Y22S-5D5HC | BssHII-STII Y22S TIR1 fused to 5D5Hc | This study |
| pBR-bDsbA1 L11I-5D5HC | BssHII-DsbA L11I TIR1 fused, to 5D5Hc | This study |
| pBR-bDsbA1 L11S-5D5HC | BssHII-DsbA L11IS TIR1 fused to 5D5Hc | This study |
| pBR-bDsbA1 L11A-5D5HC | BssHII-DsbA L11A TIR1 fused to 5D5Hc | This study |
| pBR-bDsbA1 L11C-5D5HC | BssHII-DsbA L11C TIR1 fused to 5D5Hc | This study |
| pBR-bDsbA1 L11Y-5D5HC | BssHII-DsbA L11Y TIR1 fused to 5D5Hc | This study |
| pBR-bDsbA1 L11Q-5D5HC | BssHII-DsbA L11Q TIR1 fused to 5D5Hc | This study |
| pBR-bDsbA1 L11G codon1-5D5HC | BssHII-DsbA L11G TIR1 codon1 fused to 5D5Hc | This study |
| pBR-bDsbA1 L11G codon2-5D5HC | BssHII-DsbA L11G codon2 TIR1 fused to 5D5Hc | This study |
| pBR-bDsbA1 S18Y-5D5HC | BssHII-DsbA S18Y TIR1 fused to 5D5Hc | This study |
| pBR-bSTII1 LLL-1-5D5HC | BssHII-STII A10L/S11L/M12L TIR1 fused to 5D5Hc | This study |
| pBR-bSTII1 LLL-2-5D5HC | BssHII-STII A6L/A10L/S11L codon1 TIR1 fused to 5D5IIc | This study |
| pBR-bSTII1 LLL-3-5D5HC | BssHII-STII A6L/A10L/S11L codon2 TIR1 fused to 5D5Hc | This study |
| pBR-xSfmC1-5D5HC | XbaI-SfmC TIR1 fused to 5D5Hc | This study |
| pBR-xSfmC2-5D5HC | XbaI-SfmC TIR2 fused to 5D5Hc | This study |
| pBR-mSTII1-bSTII1-mAb1 | MluI-STII TIR1 fused to mAb1 Lc, BssHII-STII TIR1 fused to mAb1 Hc | This study |
| pBR-mSTII1-bDsbA1-mAb1 | MluI-STII TIR1 fused to mAb1 Lc, BssHII-DsbA TIR1 fused to mAb1 Hc | This study |
| pBR-mSTII1-bSTII1 S11L-mAb1 | MluI-STII TIR1 fused to mAb1 Lc, BssHII-STII S11 codon2 TIR1 fused to mAb1 Hc | This study |
| pBR-mSTII1-bDsbA1 L11S-mAb1 | MluI-STII TIR1 fused to mAb1 Lc, BssHII-DsbA L11S TIR1 fused to mAb1 Hc | This study |
| pBR-mSTII1-bDsbA1 L11I-mAb1 | MluI-STII TIR1 fused to mAb1 Lc, BssHII-DsbA L11I TIR1 fused, to mAb1 Hc | This study |
| pBR-mSTII1-bSTII1-mAb2 | MluI-STII TIR1 fused to mAb2 Lc, BssHII-STII TIR1 fused to mAb2 Hc | This study |
| pBR-mSTII1-bDsbA1-mAb2 | MluI-STII TIR1 fused to mAb2 Lc, BssHII-DsbA TIR1 fused to mAb2 Hc | This study |
| pBR-mSTII1-bSTII1 S11L-mAb2 | MluI-STII TIR1 fused to mAb2 Lc, BssHII-STII S11L codon2 TIR1 fused to mAb2 Hc | This study |
| pBR-mSTII1-bDsbA1 L11S-mAb2 | MluI-STII TIR1 fused to mAb2 Lc, BssHII-DsbA L11S TIR1 fused to mAb2 Hc | This study |

Bacterial Growth. Bacteria were gown in Lauria-Bertani (LB) or complete C.R.A.P. media (Simmons et al., Journal of immunological methods, 2002) in baffled shake flasks at 37° C. or at 30° C. as indicated. Antibiotics were added at the following concentrations: carbenicillin 50 µg/ml, tetracycline 20 µg/ml. To induce protein expression, the host strain 64B4 harboring the full-length antibody expression vector or the heavy chain-only expression vector was inoculated in 5 mL of LB supplemented with 20 µL/mL tetracycline and 5 mM sodium phosphate, pH 7 and incubated with shaking at 30° C. overnight. 0.5 mL of the overnight culture was inoculated into 25 mL of complete C.R.A.P. phosphate-limiting media [2] and bacteria were grown at 30° C. with shaking for 24 hr. Optical density of the end point culture was measured at 550 nm. Bacterial samples were collected for Western blot analysis or N-terminal sequencing analysis.

Translational Strength Measurement. The translational strengths of the signal peptide variants were determined by the alkaline phosphatase assay adapted from previously publication [1, 3]. Strain 27C7 harboring the PhoA reporter vector was inoculated in 5 mL of selective LB and grown at 30° C. with shaking overnight. The overnight culture was diluted by 100 fold into 5 mL of selective LB and incubated at 30° C. with shaking for another 4 hours. Bacteria were normalized to 1 OD at wavelength 600 nm and pelleted down. The pellets were immediately suspended in 1 mL strict AP media (Simmons et al., Nature Biotechnology, 1996) and stored overnight at −20° C. The next day, bacteria were thawed and incubated with 20 µL of toluene with shaking at 37° C. for at least 1 hour. 40 µL of each sample was then added into 1 mL of 1 M Tris-HCL, pH 8 containing 1 mM-Nitrophenyl phosphate disodium salt hexahydrate (PNPP, Sigma-Aldrich) and incubated at room temperature for 1 hour. 100 µL of 1 M sodium phosphate, pH 6.5 was then added to stop the reaction. 200 µL of each sample was immediately transferred into wells of a 96 well plate and $OD_{410}$ was measured by a plate reader (Molecular Technologies). Relative translational strengths were calculated by subtracting $A_{410}$ of 27C7/pBR322 (the empty vector) from $A_{410}$ of each sample and then dividing the number by $A_{410}$ of 27C7/pPhoA86. The relative TIR strength of pPhoA86 was defined as 1.

Antibody extraction and Western Blotting analysis. End point samples from shake flask cultures were collected. To measure total heavy chain level, bacteria were normalized toll OD at 550 nm and were harvested by centrifugation at 16,000×g and 4° C. for 3 min. Pellets were resuspended in 200 µL tricine buffer with 0.2 M dithiothreitol (DTT, Sigma) and heated at 95° C. for 5 min to disrupt the disulfide bonds and denature proteins.

To extract soluble proteins from bacteria, whole cell broth was diluted into chilled lysis buffer (10 mM Tris, pH 6.8, 5 mM EDTA, 0.2 mg/mL Lysozyme, and 5 mM iodoacetic acid) to a final $OD_{550}$ of 3 and incubated on ice for 10 min. Samples were then sonicated by 10×1 sec-pulses twice and centrifuged for 15 min at 16,000×g and 4° C. Supernatant was carefully collected. 100 µL of supernatant was mixed with 100 µL of tricine buffer or tricine buffer and boiled at 95° C. for 5 min.

Periplasmic proteins were extracted as described [4, 5]. Briefly, 10 $OD_{550}$ of cells were harvested by centrifugation at 3,000×g and 4° C. for 20 min. Pellets were resuspended gently in 1 mL of cold TBS buffer (200 mM Tris, pH8.0, 0.5 mM sucrose, 1 mM EDTA) with 1 tablet of protease inhibitor cocktail (Roche). Samples were incubated on ice for 30 min and centrifuged at 16,000×g and 4° C. for 30 min. Supernatant was carefully collected. 100 µL of supernatant was mixed with 100 µL of tricine buffer with 0.2 M DTT and heated at 95° C. for 5 min.

Protein samples in tricine buffer with or without DTT were loaded onto 10% Bis-Tris SDS-PAGE gels (Life Technologies) and separated by electrophoresis. To ensure that equal amounts of total protein was loaded, gels with 1 OD lysates were stained with Coomassie blue. Proteins in non-stained gels were transferred to cellulose membranes (Biorad) by iBlot semi-dry transfer (Life Technologies) or by wet transfer (Biorad) with CAPS buffer (10 mM N-cyclohexyl-3-aminopropanesulfonic acid, 3% methanol, pH 11). Heavy chain-containing species were probed with goat anti-human Fc secondary antibody, HRP conjugated (Pierce). Light chain-containing species were probed with goat-anti-human kLc antibody, HRP conjugated (Bethyl Laboratories). Target proteins on immunoblots were detected by enhanced chemiluminescent (GE Healthcare). Edman sequencing of the N-terminus of heavy chain. End point samples from shake flask cultures were normalized to 1 $OD_{550}$ and harvested by centrifugation at 16,000×g for 3 min. Pellets were resuspended in 200 µL of tricine buffer with 0.2 M DTT and heated at 95° C. for 5 min. Proteins were separated by electrophoresis on 8% or 10% Bis-Tris SDS-PAGE gels (Life Technologies). 1 $OD_{550}$ or 4 $OD_{550}$ of cell lysate from 64B4 harboring an empty pBR322 vector was also loaded as a control. After electrophoresis, proteins were transferred to PVDF membranes by wet transfer (Biorad) in CAPS buffer. The heavy chain band at ~49 kDa on the membrane was cut out and analyzed by Edman sequencing using the Applied Biosystems Procise Sequencer Model 494HT. The ratio of mature heavy chain to precursor was estimated based on peak intensity. For semi-quantification, picomole values of each amino acid were calculated by the sequence analysis program SEQX against the uncorrected phenylthiohydantion amino acid standards (Henzel et al., Journal of Chromatography, 1987). An average of 10 cycles was used to produce the repetitive yield plot to calculate the linear regression and the initial yields of major and minor sequences were defined as the y-intercepts of the plotted lines. The heavy chain processing efficiency was calculated as the percentage of secreted heavy chain (initial yield of mature heavy chain/(initial yield of precursor+initial yield of mature heavy chain)).

Transmission electron microscopy (TEM). End point samples from shake flask cultures were first fixed in modified Karnovsky's fixative (2% paraformaldehyde and 2.5% glutaraldehyde in 0.1M sodium cacodylate buffer, ph7.2) and then post-fixed in 1% aqueous osmium tetroxide (EM Sciences, Hatfield, Pa.) for 1 h followed by overnight incubation in 0.5% Uranyl acetate at 40 C. The samples were then dehydrated through a series of ethanol concentrations (50%, 70%, 90%, 100%), followed by propylene oxide (each step was 15 min) and embedded in Eponate 12 (Ted Pella, Redding, Calif.). Ultrathin sections (80 nm) were cut with an Ultracut microtome (Leica), stained with 0.2% lead citrate and examined in a JEOL JEM-1400 transmission electron microscope (TEM) at 120 kV. Digital images were captured with a GATAN Ultrascan 1000 CCD camera.

Immunogold electron microscopy (immunoEM). In immunogold EM experiments, samples were prepared for cryosectioning. For cryosectioning, the cells were fixed in 4% paraformaldehyde with 0.1% glutaraldehyde in phosphate buffer (0.1 M; pH 7.2), washed several times in PBS, embedded in 12% gelatin and infiltrated in 2.3 M sucrose overnight at 4° C. Samples were then mounted on pins for cryo-ultramicrotomy frozen in cryosectioning chamber (supplied with liquid nitrogen). Ultrathin cryosections (100 nm) were prepared with a diamond knife (Diatome) at −80° C. using an ultramicrotome (Ultracut; Leica) equipped with a cryosectioning chamber. Thawed cryosections were transferred to Formvar- and carbon-coated EM grids (Nickel) with a drop of 2.3 M sucrose and were immunolabeled (see below) and counterstained for EM with 0.5% uranylacetate in 2% methylcellulose for 1 min at RT. For immunogold labeling: The thawed cryosections on grids were blocked in blocking agent (Aurion Inc) for 30 min and incubated with an HRP-conjugated goat anti-human Fc antibody (Pierce) for 45 min at room temperature, followed by incubation with goat anti-HRP gold-conjugated antibody (Jackson ImmunoReseareh) for 30 min. Sections were then counterstained as described above. Immunogold-labeled sections were visualized and examined in a JEOL JEM-1400 transmission electron microscope (TEM) at 120 kV. Digital images were captured with a GATAN Ultrascan 1000 CCD camera.

Results and Discussion

Production of antibodies (e.g. full-length antibodies) in *E. coli* can be achieved by secreting antibody heavy and light chain from the cytoplasm to the periplasm [2]. The secretion is mediated by an *E. coli* signal peptide, which is fused to the N-terminus of the heavy chain and light chain. The oxidizing environment and enzymes in the periplasm facilitate the assembly of the heavy chain and light chain into an antibody. The use of periplasmic secretion as a means for high-level production of heterologous proteins (e.g., antibodies) can be limited by several frequently encountered problems. First, secretion efficiency of the protein of interest (e.g., antibody) may be low. Second, the precursor in many cases is incompletely processed to mature protein. Third, over-expressed heterologous proteins often fold improperly, aggregate into insoluble inclusion bodies, or are proteolyzed by *E. coli* proteases. Fourth, antibodies are complicated multimeric proteins made from two different polypeptides, the heavy (HC) and light chains (LC), which must be exported into the periplasm, folded properly and form the appropriate disulfide bonds. The complexity of this protein folding plus secretion adds to the challenges of antibody manufacturing in *E. coli*.

While TIR optimization has been shown to be useful for generating more efficient protein secretion, other approaches not been shown to routinely improve the secretion of heterologous proteins in *E. coli*. For example, optimization of a signal protein was shown to decrease secretion of recombinant cyclodextrin glucanotransferase (CGTase) into the periplasmic space. Jonet et al J Mol Microbiol Biotechnol (2012); 22:48-58.

Two aspects of the signal peptide affect protein accumulation in the periplasm: the translational strength and the translocation efficiency. The translational initiation region (TIR) is a major determinant of the overall translation level of a protein. The TIR includes the polynucleotide that encodes the signal sequence, and extends from immediately upstream of the Shine-Delgarno sequence to approximately twenty nucleotides downstream of the initiation codon. Modifications of this polynucleotide sequence can alter the efficiency of translational initiation, thereby adjusting the level of translation of the downstream protein. Prior studies examining the effects of mutating signal peptide sequence generally did not control for potential impact on TIR strength due to changes in nucleic acid sequence; however, in our previous study, the use of different signal peptides to drive full antibody production was examined while controlling for TIR strength. At a relative TIR strength of about 1, fusion of the DsbA signal peptide to the heavy chain generally resulted in higher level of full-length antibody production than fusion of the signal peptides of STII, MalE, or PhoA (light chain signal peptide was STII in each study) (FIG. 1A). In the present study, we hypothesized that the DsbA signal peptide is more hydrophobic than the other signal peptides that were tested, and we demonstrated that the hydrophobicity of the signal peptide is important for heavy chain translocation to the periplasm and full-length antibody production.

Signal peptides affected periplasinic accumulation and processing of antibody heavy chain. We examined the effect of signal peptide variants on heavy chain accumulation in the periplasm. In all variants, the relative TIR strength was ~1 so as to control for possible effects of signal peptide hydrophobicity change on transcriptional strength. Prior studies generally have not controlled for the translational strength of modified signal peptides. If not carefully controlled as in the present study, modulation in signal peptide hydrophobicity could possibly change the translational strength of the TIR (e.g., via changes in TIR polynucleotide sequence). Changes in the translational strength of the TIR might affect secretion efficiency and protein production levels.

The N-terminus of antibody 5D5 heavy chain was fused to STII signal peptide (bSTII1), DsbA signal peptide (bDsbA1), MalE signal peptide (bMalE1), or PhoA signal peptide (bPhoA1), each with a similar translational level (Table 3). In each case, antibody 5D5 light chain was fused to the same STII signal peptide (mSTII1). The expression of both heavy chain and light chain was induced upon phosphate limitation in shake flask cultures. Periplasmic protein extracts were isolated by osmotic shock and centrifugation. Western blot analysis of the supernatant showed that use of DsbA signal peptide resulted in significantly higher levels of soluble periplasmic heavy chain than did use of the STII, MalE, or PhoA signal peptides (FIG. 1B). Because the TIR strengths of bMalE1 and bPhoA1 are higher than those of bSTII1 and bDsbA1, to exclude the possibility that higher TIR may cause inefficient secretion, we engineered two additional signal peptides, mMalE1 and mPhoA1, with TIR strengths slightly lower than those of bSTII1 and bDsbA1 (Table 3). Both mMalE1 and mPhoA1 fused to heavy chain resulted in significantly lower fall-length 5D5 and soluble periplasmic heavy chain than bDsbA1 (FIG. 1C).

To determine the effect of signal peptides on heavy chain secretion from the cytoplasm to the periplasm, we monitored the presence of mature heavy chain and precursor heavy chain. The un-secreted periplasmic protein in the cytoplasm or in the inner membrane will maintain the signal peptide sequence. During the translocation to the periplasm, the signal peptide is cleaved by the peptidase [6, 7]. Thus the mature protein that is released to the periplasm will not contain the signal peptide. The difference in molecular weight between the precursor and mature heavy chain is only 1-2 kDa, which is difficult to resolve on SDS-PAGE. Accordingly, N-terminal protein sequencing was performed to distinguish between the precursor and the mature heavy chain. Reduced heavy chain from the whole cell samples migrated as a single band on SDS-PAGE. The proteins in the SDS-PAGE are transferred to a PVDF membrane. The heavy chain bands from the PVDF membrane were cut and subjected to Edman sequencing. When heavy chain was fused to the STII, MalE, or PhoA signal peptide, sequences matching both the precursor or mature heavy chain were detected (Table 4), suggesting some heavy chain was retained in the cytoplasm or in the inner membrane. When heavy chain was fused to DsbA signal peptide, the sequence matching the precursor was very minor or non-detectable. We estimated the ratio of mature to precursor heavy chain using the peak intensity and semi-quantified the percentage of secreted heavy chain using the initial yields. Both methods showed that when fused to DsbA signal peptide, the majority of sequenced peptide corresponded to the mature heavy chain (Table 4), suggesting heavy chain was efficiently secreted to the periplasmic space (Table 4). Therefore, DsbA signal peptide mediated more efficient processing of heavy chain (from heavy chain precursor to mature heavy chain) than did the STII, MalE, or PhoA signal peptide.

We also performed immunogold electron microscopy (immunoEM) to directly visualize the cellular localization of heavy chain when it was fused to different signal peptides. Bacteria collected from shake flask cultures were subjected to cryosectioning, probed with αFc-HRP antibody followed by αHRP-18 nm gold particle secondary antibody, and analyzed under transmission electron microscope (TEM). For bacteria expressing STII-light chain and STII-heavy chain, very few immunogold signals were found in the periplasm. The majority of the gold labeling was observed on the cytoplasmic side, indicating heavy chain was predominantly trapped in the cytoplasm (FIG. 2A). In contrast, for bacteria expressing STII-light chain and DsbA-heavy chain, gold labeling was predominantly detected on the periplasmic side (FIG. 2B). Taken together, these results demonstrate that at similar translational level, use of the DsbA signal peptide resulted in more efficient heavy chain translocation and more heavy chain accumulation in the periplasm than did use of the other three signal peptides.

The hydrophobicity of the signal peptide was important for antibody heavy chain secretion to and accumulation in the periplasm. To explore the mechanism of why DsbA signal peptide was more effective in heavy chain secretion, we compared the amino acid sequences of DsbA signal peptide to STII, MalE, and PhoA signal peptides. Despite the diversity in primary sequences, signal peptides are commonly composed of three distinct regions: an N-terminal region which contains 1 or 2 positively charged amino acid residues, a hydrophobic core region often referred as the H-region, and a C-terminal region recognized by the signal peptidase [8]. Both the H-region and the full-length sequence of the DsbA signal peptide are more hydrophobic than those of the STII, MalE, and PhoA signal peptides (Table 2). We asked if the hydrophobicity of the signal peptide played an important role in antibody heavy chain translocation to the periplasm.

The hydrophobicity of DsbA and STII signal peptides was modulated by site-directed mutagenesis. Substituting Leucine11 (L11) to Serine (S) in DsbA signal peptide reduced the overall and average hydrophobicity of DsbA signal peptide (Table 7 and Table 2). The Leucine11 to Isoleucine (I) mutation in the DsbA signal peptide was generated as a control. In the STII signal peptide sequence, Serine11 was mutated to Leucine or Isoleucine to increase the hydrophobicity (Table 7 and Table 2). The mutated signal peptides were each fused to a mature PhoA protein for TIR strength measurements. The hydrophobicity signal peptide variants with similar TIR strengths to STII signal peptide TIR1 or DsbA signal peptide TIR1 (Table 3) were fused to the antibody 5D5 heavy chain. To exclude possible effects due to the light chain potentially interacting with the heavy chain and/or competing for the same secretion machinery, we designed plasmids that express only heavy chain but not light chain.

The effect of signal peptide hydrophobicity variants on heavy chain accumulation in the periplasm was monitored by Western blot analysis of the periplasm extracts (FIG. 3B). In the absence of light chain expression, use of the DsbA signal peptide resulted in more soluble heavy chain in the periplasm than did use of the STII signal peptide. Decreasing the hydrophobicity of the DsbA signal peptide by the L11S mutation strongly decreased the periplasmic level of soluble heavy chain, while the use of the DsbA signal peptide L11I control did not show much change in heavy chain level (FIG. 3A). On the other hand, increasing the hydrophobicity of the STII signal peptide increased the level of soluble heavy chain in the periplasm (FIG. 3A).

To further confirm the effect of signal peptide hydrophobicity on 5D5 heavy chain secretion, we created additional signal peptide variants (Table 2; Table 8) with a range of different hydrophobicity and fused them to 5D5 heavy chain. In STII signal sequence, Serine 11 was mutated to Alanine (A) which increases the overall and average hydrophobicity, Tyrosine (Y) which only slightly increases the hydrophobicity, or to Glutamine (Q) which decreases the hydrophobicity of STII. We also created a highly hydrophobic STII signal peptide variant by making the triple mutation of Ala6 (A6) to leucine, Alanine 10 (A10) to leucine, and Serine 11 (S11) to leucine (STII A6L, A10L, S11L). In DsbA sequence, Leucine 11 was mutated to Alanine (A) or Glutamine (Q) to decrease the overall and average hydrophobicity. All of the signal peptide variants had similar TIR strengths to STII signal peptide TIR1 or DsbA signal peptide TIR1 (Table 3).

The secretion efficiency of 5D5 heavy chain to the periplasm in the absence of light chain was determined by N-terminal sequencing as described above (Table 5). Use of the DsbA signal peptide resulted in the majority of heavy chain being mature heavy chain and a very minor presence of precursor heavy chain, indicating that secretion of 5D5 heavy chain mediated by DsbA signal peptide is efficient. Similar result was observed for the control, the DsbA L11I variant. Decreasing the hydrophobicity of DsbA signal peptide by L11A, L11S, or L11Q decreased the secretion efficiency as more precursor than mature 5D5 heavy chain was detected. On the other hand, neither STII nor STII S11Q mediated efficient secretion of 5D5 heavy chain using non-quantitative Edman sequencing, while STII S11L improved the secretion. Semi-quantitative Edman sequencing showed that STII and STII S11Y mediated inefficient secretion of 5D5 heavy chain; however, STII S11Q mutation increased the percentage of secreted 5D5 heavy chain. Increasing the STII signal peptide hydrophobicity by an S11A or an S11L mutation increased the secretion efficiency. Moreover, the S11L single residue mutation was sufficient for efficient 5D5 heavy chain secretion, as a highly hydrophobic STII signal peptide signal variant with similar translational strength (STII A6L, A10L, S11L) did not further increase secretion efficiency. Taken together, modulating signal peptide hydrophobicity while controlling the TIR strength greatly affected the secretion efficiency of 5D5 heavy chain to the periplasm.

Similar results were observed when light chain was co-expressed with heavy chain. When antibody 5D5 light chain was fused to a STII signal peptide (mSTII1), the use of the DsbA L11S signal peptide resulted in significantly less aqueous-soluble heavy chain in the periplasm than the use of the DsbA or DsbA L11I signal peptides. Similarly, use of the STII S11L or STII S11I signal peptide mediated more soluble heavy chain accumulation in the periplasm than did the STII signal peptide (FIG. 3B). Collectively, modulation of the signal peptide hydrophobicity significantly altered 5D5 heavy chain accumulation in the periplasm. Increasing the hydrophobicity by a single amino acid change significantly improved the periplasmic level of soluble heavy chain, while decreasing the hydrophobicity had the opposite effect.

We further analyzed the effects of signal peptide hydrophobicity on heavy chain processing by N-terminal sequencing (Table 4). In each case, 5D5 light chain was fused to STII signal peptide (mSTII1). Major mature heavy chain signal and very minor precursor signal were detected by N-terminal sequencing when heavy chain was fused to DsbA and DsbA L11I signal peptides. Using an estimation based on peak intensity, the ratio of mature heavy chain to precursor heavy chain for the construct using DsbA signal peptide was more than 10:1. The L11S mutation in the DsbA signal peptide decreased the mature/precursor ratio to 1:3 as more precursor than mature heavy chain signal was detected. The STII signal peptide gave less mature heavy chain signal than precursor signal, with a mature/precursor ratio of 1:3. Improving STII signal peptide hydrophobicity by an S11L or an S11I mutation resulted in more mature heavy chain than the precursor heavy chain (3:1 and 4:1). Semi-quantification using initial yields from Edman sequencing confirmed the effects of signal peptide hydrophobicity on the secretion of 5D5 heavy chain. Use of DsbA signal peptide resulted in 86% secreted heavy chain; the L11S mutation decreased the percentage of secreted heavy chain to 39%. STII mediated 39% secreted heavy chain; S11L and S11I mutation increased heavy chain secretion to more than 60%. Together, the hydrophobicity of the signal peptide was important for antibody heavy chain processing and secretion to the periplasm.

The effects of signal peptide hydrophobicity on 5D5 secretion was also supported by the study of a highly hydrophobic signal peptide from SfmC. SfmC is a predicted pilin protein localized in the periplasm. The secretion of SfmC is dependent on the signal recognition particle (SRP) in the co-translational secretion pathway (Huber et al., J Bacteriol. 2005. 2983-2991; Zhou at al., 2014. PLOS One). The signal peptide of SfmC is more hydrophobic than the signal peptides of either DsbA or STII (Table 3). We generated TIR1 and TIR2 variants of the SfmC signal peptide and fused them each to 5D5 heavy chain. Both variants mediated very efficient secretion of 5D5 heavy chain (100% secreted heavy chain).

The effects of signal peptide hydrophobicity on full-length antibody levels. We next analyzed the effect of signal peptide hydrophobicity on full-length antibody production. Lysates from the host cells expressing 5D5 heavy chain and light chain were collected and levels of fully assembled antibody 5D5 were analyzed by non-reducing SDS-PAGE electrophoresis followed by Western blot. In each case, 5D5 light chain was fused to STII signal peptide (using the mSTII1 nucleic acid sequence). DsbA L11S signal peptide fused to heavy chain resulted in a significant decrease of full-length 5D5 level compared to use of DsbA or DsbA L11I signal peptides fused to the heavy chain (FIG. 4A). On the other hand, both S11L and L11I mutations in the STII signal peptide increased the full-length 5D5 antibody level compared to use of the STII signal peptide (FIG. 4B). Therefore, increasing the hydrophobicity of signal peptide promoted the production of full-length 5D5 antibody.

We wanted to know whether the effect of signal peptide hydrophobicity applies to the secretion of other antibody heavy chains. For this purpose, we fused STII, STII S11L, DsbA, or DsbA L11S TIR1 signal peptides to the heavy chain of mAb1 or mAb2 and measured the secretion efficiency of heavy chain in the absence of light chain using Edman sequencing (Table 6). For both antibody heavy chains, DsbA mediated more secreted heavy chain than STII. Decreasing the hydrophobicity of DsbA by L11S mutation decreased the percentage of secreted heavy chain, and increasing the hydrophobicity of STII by S11L mutation showed the opposite effect.

We further tested the effect of signal peptide hydrophobicity on full-length antibody production of two other monoclonal antibodies, mab 1 and mab 2 (FIG. 7). Mab 1 and mab 2 are each full-length IgG1 antibodies. In both cases, the light chain was fused to mSTII1, and the heavy chain was fused to STII, DsbA, STII S11L, or DsbA L11S with similar TIR strengths. Full-length antibody levels, periplasmic soluble heavy chain levels, and total heavy chain levels were determined as described previously. For mAb1, STII or DsbA signal peptides fused to heavy chain resulted in similar levels of full-length antibody and periplasmic soluble heavy chain; however, use of the DsbA L11S signal peptide variant with decreased hydrophobicity significantly decreased levels of full-length mAb1 and periplasmic soluble heavy chain, suggesting signal peptide hydrophobicity is still an important factor for mAb1 production and secretion into the periplasm. For mAb2, use of STII signal peptide resulted in less full-length antibody and less periplasmic soluble heavy chain than did use of DsbA signal peptide. Increasing STII signal peptide hydrophobicity by S11L mutation caused an increase of full-length mAb2 as well as periplasmic soluble heavy chain accumulation, while decreasing the hydrophobicity of DsbA signal peptide by L11S mutation had the opposite effect. Therefore, signal peptide hydrophobicity is important for mAb2 production and secretion into the E. coli periplasm.

Modulation of the signal peptide hydrophobicity changed cellular localization of inclusion bodies. Overexpressed recombinant proteins in E. coli are often contained in large insoluble aggregates known as inclusion bodies in the cytoplasm or in the periplasm. Formation of inclusion bodies containing proteins of interest is often associated with low levels of soluble target proteins. Moreover, inclusion body formation in the cytoplasm indicates inefficient protein secretion to the periplasm. Using transmission electron microscopy (TEM), we observed inclusion bodies prominently in the cytoplasm of host cells expressing light chain fused to mSTII1 and heavy chain fused to the STII, MalE, or PhoA signal peptide (FIG. 5), suggesting inefficient protein secretion in these cells. In contrast, for host cells expressing STII-LC and DsbA-HC, inclusion bodies were less commonly observed and were mostly localized in the periplasm (FIG. 5), indicating efficient protein secretion. Interestingly, use of STII S11L signal peptide (with increased hydrophobicity) showed a phenotype similar to that of the DsbA signal peptide: inclusion bodies were mostly localized on the periplasmic side (FIG. 5). Use of the DsbA L11S signal peptide (with reduced hydrophobicity) resulted in inclusion bodies observed predominantly in the cytoplasm (FIG. 5). In sum, modulation of signal peptide hydrophobicity altered the cellular localization of inclusion bodies.

Mutations in the C-terminal domain of the signal peptide did not alter full-length antibody production. The C-terminal region of the signal peptide is critical for the cleavage of signal peptide by peptidase. Prior studies indicate that this region typically prefers amino acid residues with small side-chain at −1 and −3 position in the cleavage site [6]. Both STII and DsbA signal peptides have the small residue (Ala) at the −1 and −3 position (FIG. 3A). However, at the −2 position in DsbA sequence there is a small residue Ser, whereas at the same position in STII sequence there is a bulky residue (Tyr (Y)). FIG. 6 shows that alterations in the side chain size in the −2 amino acid position in the cleavage site does not affect antibody 5D5 production. The Tyr22 to Ser mutation in the STII signal peptide did not change the 5D5 level. Similarly, the Ser18 to Tyr mutation in the DsbA signal peptide had no effect on 5D5 level. Therefore, the side-chain bulkiness in the −2 amino acid position does not affect 5D5 levels in the periplasm.

TABLE 2

Amino acid sequences of signal peptide variants

| Parent gene | Clone number | Amino acid sequence | SEQ ID NO: | Sum hydro | Ave hydro | Sum hydro (H) | Ave hydro (H) |
| --- | --- | --- | --- | --- | --- | --- | --- |
| STII | bSTII1 | MKKNIAFLLASM FVFSIATNAYA | 1 | 9.20 | 0.40 | 10.27 | 0.73 |
| STII | mSTII1 | MKKNIAFLLASM FVFSIATNAYA | 2 | 9.20 | 0.40 | 10.27 | 0.73 |
| DsbA | vDsbA1 | MKKIWLALAGLV LAFSASA | 3 | 9.56 | 0.50 | 9.23 | 0.92 |
| PhoA | bPhoA1 | MKQSTIALALLPL LFTPVTKA | 4 | 7.51 | 0.36 | 9.00 | 0.75 |

TABLE 2-continued

Amino acid sequences of signal peptide variants

| Parent gene | Clone number | Amino acid sequence | SEQ ID NO: | Sum hydro | Ave hydro | Sum hydro (H) | Ave hydro (H) |
|---|---|---|---|---|---|---|---|
| PhoA | mPhoA1 | MKQSTIALALLPL LFTPVTKA | 5 | 7.51 | 0.36 | 9.00 | 0.75 |
| MalE | bMalE1 | MKIKTGARILALS ALTTMMFSASAL A | 6 | 8.09 | 0.31 | 6.54 | 0.41 |
| MalE | bMalE1 | MKIKTGARILALS ALTTMMFSASAL A | 7 | 8.09 | 0.31 | 6.54 | 0.41 |
| STII | bSTII1 S11L | MKKNIAFLLALM FVFSIATNAYA | 8 | 10.44 | 0.45 | 11.51 | 0.82 |
| STII | bSTII1 S11L codon1 | MKKNIAFLLALM FVFSIATNAYA | 9 | 10.44 | 0.45 | 11.51 | 0.82 |
| STII | bSTII1 S11L codon2 | MKKNIAFLLALM FVFSIATNAYA | 10 | 10.44 | 0.45 | 11.51 | 0.85 |
| STII | bSTII1 S11I | MKKNIAFLLAIMF VFSIATNAYA | 11 | 10.76 | 0.47 | 11.83 | 0.85 |
| STII | bSTII1 Y22S | MKKNIAFLLASM FVFSIATNASA | 12 | 8.76 | 0.38 | — | — |
| DsbA | bDsbA1 L11I | MKKIWLALAGIV LAFSASA | 13 | 9.88 | 0.52 | 9.55 | 0.96 |
| DsbA | bDsbA1 L11S | MKKIWLALAGSV LAFSASA | 14 | 8.32 | 0.44 | 7.99 | 0.80 |
| DsbA | bDsbA1 S18Y | MKKIWLALAGLV LAFSAYA | 15 | 10.00 | 0.53 | — | — |
| STII | bSTII1 S11A | MKKNIAFLLAAM FVFSIATNAYA | 31 | 10.00 | 0.43 | 11.07 | 0.79 |
| STII | bSTII1 S11Q | MKKNIAFLLAQM FVFSIATNAYA | 32 | 8.53 | 0.37 | 9.60 | 0.69 |
| STII | bSTII1 A6L A10L S11L | MKKNILFLLLLMF VFSIATNAYA | 33 | 11.32 | 0.49 | 13.01 | 0.87 |
| DsbA | bDsbA L11A | MKKIWLALAGAV LAFSASA | 34 | 9.12 | 0.48 | 8.79 | 0.88 |
| DsbA | bDsbA L11Q | MKKIWLALAGQV LAFSASA | 35 | 7.65 | 0.40 | 7.32 | 0.73 |
| STII | bSTII1 L11Y | MKKNIAFLLAYM FVFSIATNAYA | 41 | 9.64 | 0.42 | 10.71 | 0.77 |
| SfmC | xSfmC1 | MMTKIKLLMLIIF YLIISASAHA | 42 | 12.56 | 0.55 | 1.85 | 1.08 |
| SfmC | xSfmC2 | MMTKIKLLMLIIF YLIISASAHA | 43 | 12.56 | 0.55 | 1.85 | 1.08 |

Underline = mutations in amino acid sequences?
Sum hydrophobicity (sum hydro) is calculated based on the normalized consensus scale developed by Eisenberg et al [20].?
Ave hydro = sum hydrophobicity of the signal sequence divided by the number of amino acid residues?
Sum hydro (H) = sum hydrophobicity of the H-region?
Ave hydro (H) = average hydrophobicity of the H-region?

TABLE 3

DNA sequences of signal peptide variants and relative TIR strengths

| Parent gene | Clone number | Relative TIR strengths | SEQ ID NO: | DNA sequences |
|---|---|---|---|---|
| STII | bSTII1 | 0.65 ± 0.11 | 16 | GCGCGCATTATGAAGAAAAACATCGCTTT<br>TCTTCTTGCATCTATGTTCGTTTTTTCTATT<br>GCTACAAACGCTTACGCT |
| STII | mSTII1 | 0.31 ± 0.03 | 17 | ACGCGTATTATGAAGAAAAACATCGCTTT<br>TCTTCTTGCATCTATGTTCGTTTTTTCTATT<br>GCTACAAACGCTTAC |
| DsbA | bDsbA1 | 0.85 ± 0.12 | 18 | GCGCGCATTATGAAAAAAATTTGGCTCGC<br>CCTGGCTGGTTTAGTTTTAGCGTTTAGCGC<br>ATCGGCG |
| PhoA | bPhoA1 | 1.63 ± 0.07 | 19 | GCGCGCATTATGAAACAATCCACGATTGC<br>CCTGGCACTGTTACCGTTACTGTTTACCCC<br>TGTGACAAAAGCC |
| PhoA | mPhoA1 | 0.67 ± 0.04 | 20 | ACGCGTATTATGAAACAGTCTACTATCGC<br>TCTGGCACTCTTACCGTTACTGTTTACCCCT<br>GTGACAAAAGCC |
| MalE | bMalE1 | 1.80 ± 0.12 | 21 | GCGCGCATTATGAAAATTAAGACTGGAGC<br>ACGCATCCTCGCATTATCCGCATTAACGAC<br>GATGATGTTTTCCGCCTCGGCTCTCGCC |
| MalE | mMalE1 | 0.44 ± 0.06 | 22 | ACGCGTATTATGAAGATCAAGACAGGCGC<br>GCGCATCCTCGCATTATCCGCATTAACGAC<br>GATGATGTTTTCCGCCTCGGCTCTCGCC |
| STII | bSTII1 S11L | 0.29 ± 0.02 | 23 | GCGCGCATTATGAAGAAAAACATCGCTTT<br>TCTTCTTGCAT<u>TAA</u>TGTTCGTTTTTTCTATT<br>GCTACAAACGCTTACGCT |
| STII | bSTII1 codon 1 | 0.77 ± 0.03 | 24 | GCGCGCATTATGAAGAAAAACATCGCTTT<br>TCTTCTTGCA<u>TTG</u>ATGTTCGTTTTTTCTATT<br>GCTACAAACGCTTACGCT |
| STII | bSTII1 codon 2 | 0.78 ± 0.04 | 25 | GCGCGCATTATGAAGAAAAACATCGCTTT<br>TCTTCTTGCA<u>CTC</u>ATGTTCGTTTTTTCTATT<br>GCTACAAACGCTTACGCT |
| STII | bSTII1 S11I | 0.78 ± 0.06 | 26 | GCGCGCATTATGAAGAAAAACATCGCTTT<br>TCTTCTTGCA<u>ATT</u>ATGTTCGTTTTTTCTATT<br>GCTACAAACGCTTACGCT |
| STII | bSTII1 Y22S | 0.82 ± 0.04 | 27 | GCGCGCATTATGAAGAAAAACATCGCTTT<br>TCTTCTTGCATCTATGTTCGTTTTTTCTATT<br>GCTACAAACGCTT<u>TC</u>GCT |
| DsbA | bDsbA1 L11I | 0.79 ± 0.06 | 28 | GCGCGCATTATGAAAAAAATTTGGCTCGC<br>CCTGGCTGGT<u>ATT</u>GTTTTAGCGTTTAGCGC<br>ATCGGCG |
| DsbA | bDsbA1 L11S | 0.99 ± 0.05 | 29 | GCGCGCATTATGAAAAAAATTTGGCTCGC<br>CCTGGCTGGT<u>TCT</u>GTTTTAGCGTTTAGCGC<br>ATCGGCG |
| DsbA | bDsbA1 S18Y | 0.86 ± 0.05 | 30 | GCGCGCATTATGAAAAAAATTTGGCTCGC<br>CCTGGCTGGTTTAGTTTTAGCGTTTAGCGC<br>A<u>TAC</u>GCG |
| STII | bSTII1 S11A | 0.48 ± 0.08 | 31 | GCGCGCATTATGAAGAAAAACATCGCTTT<br>TCTTCTTGCA<u>GC</u>AATGTTCGTTTTTTCTATT<br>GCTACAAACGCTTACGCT |
| STII | bSTII1 S11Q | 0.55 ± 0.05 | 32 | GCGCGCATTATGAAGAAAAACATCGCTTT<br>TCTTCTTGCA<u>CAA</u>ATGTTCGTTTTTTCTATT<br>GCTACAAACGCTTACGCT |
| STII | bSTII1 A6L A10L S11L | 0.83 ± 0.04 | 33 | GCGCGCATTATGAAGAAAAACATC<u>CT</u>CTT<br>TCTTCTT<u>CTACTA</u>ATGTTCGTTTTTTCTATT<br>GCTACAAACGCTTACGCT |

TABLE 3-continued

DNA sequences of signal peptide variants and relative TIR strengths

| Parent gene | Clone number | Relative TIR strengths | SEQ ID NO: | DNA sequences |
|---|---|---|---|---|
| DsbA | bDsbA1 L11A | 1.25 ± 0.06 | 34 | GCGCGCATTATGAAAAAAATTTGGCTCGC CCTGGCTGGTGCTGTTTTAGCGTTTAGCGC ATCGGCG |
| DsbA | bDsbA1 L11Q | 0.94 ± 0.05 | 35 | GCGCGCATTATGAAAAAAATTTGGCTCGC CCTGGCTGGTCAGGTTTTAGCGTTTAGCGC ATCGGCG |
| STII | BsTII1 S11Y | 0.61 ± 0.06 | 36 | GCGCGCATTATGAAGAAAAACATCGCTTT TCTTCTTGCATACATGTTCGTTTTTTCTATT GCTACAAACGCTTACGCT |
| SfmC | xSfmC1 | 1.22 ± 0.08 | 37 | TCTAGAATTATGATGACTAAAATCAAGCT TCTAATGCTCATTATATTTTATTTAATCATT TCGGCCAGCGCCCATGCT |
| SfmC | xSfmC1 | 2.22 ± 0.16 | 38 | TCTAGAATTATGATGACGAAAATCAAGCT ACTGATGCTCATTATATTTTATTTAATCATT TCGGCCAGCGCCCATGCT |

Bold = BssHII, MluI or XbaI restriction site
Underline = mutations made to change the amino acid sequences

TABLE 4

Secretion of 5D5 heavy chain with co-expression of 5D5 light chain

| Signal peptide for heavy chain | Mature HC | Precursor HC | Estimated mature/ precursor ratio* | Secreted HC % ** |
|---|---|---|---|---|
| bSTII1 | Minor | Major | 1:3 | 45 |
| bDsbA1 | Major | Minor or not detected | >10:1 | 86 |
| bMalE1 | Detected | Detected | N/D | N/D |
| mMalE1 | Minor | Major | N/D | 35 |
| bPhoA1 | Minor | Major | N/D | ND |
| mPhoA1 | Minor | Major | N/D | 6 |
| bDsbA1 L11I | Major | Not detected | N/D | 81 |
| bDsbA1 L11S | Minor | Major | 1:3 | 39 |
| bSTII1 S11L | Major | Minor | 3:1 | N/D |
| bSTII1 S11L codon2 | Major | Minor | N/D | 67 |
| bSTII1 S11I | Major | Minor | 4:1 | 66 |

*Estimated mature/precursor ratio is based on a rough estimation of peak intensity.
** The secreted HC % is determined by the semi-quantification of the initial yields of mature heavy chains and the precursors, as described in the Materials and Methods section.

TABLE 5

Secretion of 5D5 heavy chain in the absence of 5D5 light chain

| Signal peptide for heavy chain | Mature HC | Precursor HC | Secreted HC %* |
|---|---|---|---|
| bSTII1 | Detected | Detected | 34 |
| bDsbA1 | Major | Minor or not detected | 84 |
| bMalE1 | Minor | Major | 12 |
| mMalE1 | Minor | Major | 11 |
| mPhoA1 | Minor | Major | 4 |
| bSTII1 S11Q | Detected | Detected | 68 |
| bSTII1 S11A | Major | Minor | 66 |
| bSTII1 S11Y | Minor | Major | 22 |
| bSTII1 S11L | Detected | Very minor or not detected | 70 |
| bSTII1 A6L A10L S11L | Major | Very minor | 65 |
| bDsbA1 L11I | Major | Minor | 82 |
| bDsbA1 L11A | Minor | Major | 60 |
| bDsbA1 L11S | Minor | Major | 38 |
| bDsbA1 L11Q | Minor | Major | 20 |
| xSfmC1 | Detected | Extremely low coverage | 100 |
| xSfmC2 | Detected | Extremely low coverage | 100 |

*The secreted HC % is determined by the semi-quantification of the initial yields of mature heavy chains and the precursors, as described in the Materials and Methods section.

TABLE 6

Secretion of mAb1 heavy chain and mAb2 heavy chain in the absence of light chain.

| Signal peptide for heavy chain | Cargo heavy chain | Secreted HC %* |
|---|---|---|
| bSTII1 | mAb1 HC | 35 |
| bSTII1 S11L codon2 | mAb1 HC | 78 |
| bDsbA1 | mAb1 HC | 86 |
| bDsbA1 L11S | mAb1 HC | 12 |
| bSTII1 | mAb2 HC | 17 |
| bSTII1 S11L codon2 | mAb2 HC | 77 |
| bDsbA1 | mAb2 HC | 89 |
| bDsbA1 L11S | mAb2 HC | 71 |

*The secreted HC % is determined by the semi-quantification of the initial yields of mature heavy chains and the precursors, as described in the Materials and Methods section.

TABLE 7

Amino acid sequences of DsbA signal sequence, sill signal sequence, and variant signal sequences with altered hydrophobicity. The N-terminal region is marked in bold, the H-region is italicized, and the C-terminal region is in regular font. Mutated residues are underlined.

| Signal peptide | Amino acid sequence | SEQ ID NO: |
|---|---|---|
| DsbA | MKK_IWLALAGLVL_AFSASA | 47 |
| DsbA L11I | MKK_IWLALAGIVL_AFSASA | 49 |
| DsbA L11S | MKK_IWLALAGSVL_AFSASA | 50 |
| STII | MKK_NIAFLLASMFVFSI_ATNAYA | 51 |
| STII S11L | MKK_NIAFLLALMFVFSI_ATNAYA | 52 |
| STII S11I | MKK_NIAFLLAIMFVFSI_ATNAYA | 53 |

TABLE 8

Amino acid sequence of DsbA signal sequence; STII signal sequence, variant signal sequences with altered hydrophobicity, and the SfmC signal sequence. The N-terminal region is marked in bold, the H-region is italicized, and the C-terminal region is in regular font. Mutated residues are underlined.

| Signal peptide | Amino acid sequence | SEQ ID NO: |
|---|---|---|
| DsbA | MKK_IWLALAGLVL_AFSASA | 54 |
| DsbA L11A | MKK_IWLALAGAVL_AFSASA | 55 |
| Dsba L11Q | MKK_IWLALAGQVL_AFSASA | 56 |
| STII | MKK_NIAFLLASMFVFSI_ATNAYA | 57 |
| STII S11A | MKK_NIAFLLAAMFVFSI_ATNAYA | 58 |
| STII S11Q | MKK_NIAFLLAQMFVFSI_ATNAYA | 59 |
| STII S11Y | MKK_NIAFLLAYMFVFSI_ATNAYA | 60 |
| STII A6L, A10L, S11L | MKK_NILFLLLLMFVFSI_ATNAYA | 61 |
| SfmC | MMTKIK_LLMLIIFYLII_SASAHA | 62 |

PARTIAL REFERENCE LIST

1. Simmons, L. C. and D. G. Yansura, Nat Biotechnol, 1996. 14(5): p. 629-34.
2. Simmons, L. C., et al., J Immunol Methods, 2002. 263(1-2): p. 133-47.
3. U.S. Pat. No. 8,361,744
4. Quan, S., et al., Methods Mol 2013. 966: p. 359-66.
5. Oliver, D. B. and J. Beckwith, Cell, 1982. 30(1): p. 311-9.
6. Auclair, S. M., M. K. Bhanu, and D. A. Kendall, Protein Sci, 2012. 21(1): p. 13-25.
7. Josefsson, L. G. and L. L. Randall, Cell, 1981. 25(1): p. 151-7.
8. Izard J W, K. D., Mol Microbiol, 1994. 13(5): p. 765-73.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of increasing secretion of a biologically active antibody comprising an antibody heavy chain and an antibody light chain from an *E. coli* host cell, comprising culturing an *E. coli* host cell comprising a polynucleotide encoding the antibody, wherein the polynucleotide comprising
   (1) a first polynucleotide encoding a first signal peptide operably linked to a polynucleotide encoding the antibody heavy chain, and
   (2) a second polynucleotide encoding a second signal peptide operably linked to a polynucleotide encoding the antibody light chain;
   wherein (a) the first signal peptide comprises the sequence of SEQ ID NO:13, 14, 15, 34, or 35, and/or (b) the second signal peptide comprises the sequence of SEQ ID NO:13, 14, 15, 34, or 35;
   whereby upon expression of the antibody heavy chain and antibody light chain in the host cell, the antibody heavy and antibody light chains are folded and assembled to form the biologically active antibody.

2. The method of claim 1, wherein the relative translation initiation region (TIR) strength of the first and/or second signal peptide to a wild type signal peptide is about 1, about 2, about 3, about 4, about 5, about 6, about 7, or about 8.

3. The method of claim 2, wherein the relative TIR strength of the first signal peptide to a wild type signal peptide is about 5 and the relative TIR strength of the second signal sequence to a wild type signal peptide is about 8.

4. The method of claim 1, wherein the polynucleotide encoding the antibody in the host cell further comprises (i) a first promoter, wherein the first promoter is operably linked to the polynucleotide encoding the heavy chain and (ii) a second promoter, wherein the second promoter is operably linked to the polynucleotide encoding the light chain.

5. The method of claim 4, wherein the first and second promoters are prokaryotic promoter independently selected from the group consisting of phoA, tac, lpp, lac-lpp, lac, ara, and T7 promoter.

6. The method of claim 4, wherein the polynucleotide encoding the antibody in the host cell further comprises (iii) a third promoter, wherein the third promoter is operably linked to a polynucleotide encoding an Fc polypeptide.

7. The method of claim 1, wherein the *E. coli* host cell is of a strain deficient in endogenous protease activities.

8. The method of claim 7, wherein the genotype of the *E. coli* lacks degP and prc genes and harbors a mutant spr gene.

9. The method of claim 1, wherein the host cell further comprises a polynucleotide encoding at least one prokaryotic polypeptide selected from the group consisting of DsbA, DsbC, DsbG and FkpA.

10. The method of claim 9, wherein the polynucleotide encoding at least one prokaryotic polypeptide encodes both DsbA and DsbC.

11. The method of claim 1, wherein the method further comprises recovering the antibody from the host cell culture.

12. The method of claim 11, wherein the antibody is recovered from the host cell culture medium.

13. The method of claim 11, wherein the method further comprises combining the recovered antibody with a pharmaceutically acceptable carrier, excipient, or carrier to prepare a pharmaceutical formulation comprising the antibody.

14. The method of claim 1, wherein the antibody is a monoclonal antibody.

15. The method of claim 14, wherein the antibody is a chimeric antibody, an affinity matured antibody, a bispecific antibody, humanized antibody, or a human antibody.

16. The method of claim 14, wherein the antibody is a bispecific antibody.

\* \* \* \* \*

SEQUENCE LISTING

```
<160> NUMBER OF SEQ ID NOS: 62

<210> SEQ ID NO 1
<211> LENGTH: 23
<212> TYPE: PRT
<213> ORGANISM: Artificial Sequence
<220> FEATURE:
<223> OTHER INFORMATION: Synthetic Construct

<400> SEQUENCE: 1

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic Construct
```

```
<400> SEQUENCE: 2

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 3
<211> LENGTH: 19
<212> TYPE: PRT
<213> ORGANISM: Artificial Sequence
<220> FEATURE:
<223> OTHER INFORMATION: Synthetic Construct

<400> SEQUENCE: 3

Met Lys Lys Ile Trp Leu Ala Leu Ala Gly Leu Val Leu Ala Phe Ser
1               5                   10                  15

Ala Ser Ala

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct

<400> SEQUENCE: 4

Met Lys Gln Ser Thr Ile Ala Leu Ala Leu Leu Pro Leu Leu Phe Thr
1               5                   10                  15

Pro Val Thr Lys Ala
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic Construct

<400> SEQUENCE: 5

Met Lys Gln Ser Thr Ile Ala Leu Ala Leu Leu Pro Leu Leu Phe Thr
1               5                   10                  15

Pro Val Thr Lys Ala
            20

<210> SEQ ID NO 6
<211> LENGTH: 26
<212> TYPE: PRT
<213> ORGANISM: Artificial Sequence
<220> FEATURE:
<223> OTHER INFORMATION: Synthetic Construct

<400> SEQUENCE: 6

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic Construct
```

```
<400> SEQUENCE: 7

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 8
<211> LENGTH: 23
<212> TYPE: PRT
<213> ORGANISM: Artificial Sequence
<220> FEATURE:
<223> OTHER INFORMATION: Synthetic Construct

<400> SEQUENCE: 8

Met Lys Lys Asn Ile Ala Phe Leu Leu Ala Leu Met Phe Val Phe Ser
1               5                   10                  15

Ile Ala Thr Asn Ala Tyr Ala
            20

<210> SEQ ID NO 9
<211> LENGTH: 23
<212> TYPE: PRT
<213> ORGANISM: Artificial Sequence
<220> FEATURE:
<223> OTHER INFORMATION: Synthetic Construct

<400> SEQUENCE: 9

Met Lys Lys Asn Ile Ala Phe Leu Leu Ala Leu Met Phe Val Phe Ser
1               5                   10                  15

Ile Ala Thr Asn Ala Tyr Ala
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct

<400> SEQUENCE: 10

Met Lys Lys Asn Ile Ala Phe Leu Leu Ala Leu Met Phe Val Phe Ser
1               5                   10                  15

Ile Ala Thr Asn Ala Tyr Ala
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

<400> SEQUENCE: 11

Met Lys Lys Asn Ile Ala Phe Leu Leu Ala Ile Met Phe Val Phe Ser
1               5                   10                  15

Ile Ala Thr Asn Ala Tyr Ala
            20

<210> SEQ ID NO 12
<211> LENGTH: 23
<212> TYPE: PRT
<213> ORGANISM: Artificial Sequence
<220> FEATURE:
<223> OTHER INFORMATION: Synthetic Construct
```

<400> SEQUENCE: 12

Met Lys Lys Asn Ile Ala Phe Leu Leu Ala Ser Met Phe Val Phe Ser
1               5                   10                  15

Ile Ala Thr Asn Ala Ser Ala
            20

<210> SEQ ID NO 13
<211> LENGTH: 19
<212> TYPE: PRT
<213> ORGANISM: Artificial Sequence
<220> FEATURE:
<223> OTHER INFORMATION: Synthetic Construct

<400> SEQUENCE: 13

Met Lys Lys Ile Trp Leu Ala Leu Ala Gly Ile Val Leu Ala Phe Ser
1               5                   10                  15

Ala Ser Ala

<210> SEQ ID NO 14
<211> LENGTH: 19
<212> TYPE: PRT
<213> ORGANISM: Artificial Sequence
<220> FEATURE:
<223> OTHER INFORMATION: Synthetic Construct

<400> SEQUENCE: 14

Met Lys Lys Ile Trp Leu Ala Leu Ala Gly Ser Val Leu Ala Phe Ser
1               5                   10                  15

Ala Ser Ala

<210> SEQ ID NO 15
<211> LENGTH: 19
<212> TYPE: PRT
<213> ORGANISM: Artificial Sequence
<220> FEATURE:
<223> OTHER INFORMATION: Synthetic Construct

<400> SEQUENCE: 15

Met Lys Lys Ile Trp Leu Ala Leu Ala Gly Leu Val Leu Ala Phe Ser
1               5                   10                  15

Ala Tyr Ala

<210> SEQ ID NO 16
<211> LENGTH: 78
<212> TYPE: DNA
<213> ORGANISM: Artificial Sequence
<220> FEATURE:
<223> OTHER INFORMATION: Synthetic Construct

<400> SEQUENCE: 16
gcgcgcatta tgaagaaaaa catcgctttt cttcttgcat ctatgttcgt tttttctatt       60
gctacaaacg cttacgct                                                    78

<210> SEQ ID NO 17
<211> LENGTH: 75
<212> TYPE: DNA
<213> ORGANISM: Artificial Sequence
<220> FEATURE:
<223> OTHER INFORMATION: Synthetic Construct

<400> SEQUENCE: 17
acgcgtatta tgaagaaaaa catcgctttt cttcttgcat ctatgttcgt tttttctatt       60

```
gctacaaacg cttac                                                    75

<210> SEQ ID NO 18
<211> LENGTH: 66
<212> TYPE: DNA
<213> ORGANISM: Artificial Sequence
<220> FEATURE:
<223> OTHER INFORMATION: Synthetic Construct

<400> SEQUENCE: 18
gcgcgcatta tgaaaaaaat ttggctcgcc ctggctggtt tagttttagc gtttagcgca   60
tcggcg                                                              66

<210> SEQ ID NO 19
<211> LENGTH: 72
<212> TYPE: DNA
<213> ORGANISM: Artificial Sequence
<220> FEATURE:
<223> OTHER INFORMATION: Synthetic Construct

<400> SEQUENCE: 19
gcgcgcatta tgaaacaatc cacgattgcc ctggcactct taccgttact gtttacccct   60
gtgacaaaag cc                                                       72

<210> SEQ ID NO 20
<211> LENGTH: 72
<212> TYPE: DNA
<213> ORGANISM: Artificial Sequence
<220> FEATURE:
<223> OTHER INFORMATION: Synthetic Construct

<400> SEQUENCE: 20
acgcgtatta tgaaacagtc tactatcgct ctggcactct taccgttact gtttacccct   60
gtgacaaaag cc                                                       72

<210> SEQ ID NO 21
<211> LENGTH: 87
<212> TYPE: DNA
<213> ORGANISM: Artificial Sequence
<220> FEATURE:
<223> OTHER INFORMATION: Synthetic Construct

<400> SEQUENCE: 21
gcgcgcatta tgaaaattaa gactggagca cgcatcctcg cattatccgc attaacgacg   60
atgatgtttt ccgcctcggc tctcgcc                                       87

<210> SEQ ID NO 22
<211> LENGTH: 87
<212> TYPE: DNA
<213> ORGANISM: Artificial Sequence
<220> FEATURE:
<223> OTHER INFORMATION: Synthetic Construct

<400> SEQUENCE: 22
acgcgtatta tgaagatcaa gacaggcgcg cgcatcctcg cattatccgc attaacgacg   60
atgatgtttt ccgcctcggc tctcgcc                                       87

<210> SEQ ID NO 23
<211> LENGTH: 78
<212> TYPE: DNA
<213> ORGANISM: Artificial Sequence
<220> FEATURE:
```

<223> OTHER INFORMATION: Synthetic Construct

<400> SEQUENCE: 23
gcgcgcatta tgaagaaaaa catcgctttt cttcttgcat taatgttcgt tttttctatt   60
gctacaaacg cttacgct   78

<210> SEQ ID NO 24
<211> LENGTH: 78
<212> TYPE: DNA
<213> ORGANISM: Artificial Sequence
<220> FEATURE:
<223> OTHER INFORMATION: Synthetic Construct

<400> SEQUENCE: 24
gcgcgcatta tgaagaaaaa catcgctttt cttcttgcat tgatgttcgt tttttctatt   60
gctacaaacg cttacgct   78

<210> SEQ ID NO 25
<211> LENGTH: 78
<212> TYPE: DNA
<213> ORGANISM: Artificial Sequence
<220> FEATURE:
<223> OTHER INFORMATION: Synthetic Construct

<400> SEQUENCE: 25
gcgcgcatta tgaagaaaaa catcgctttt cttcttgcac tcatgttcgt tttttctatt   60
gctacaaacg cttacgct   78

<210> SEQ ID NO 26
<211> LENGTH: 78
<212> TYPE: DNA
<213> ORGANISM: Artificial Sequence
<220> FEATURE:
<223> OTHER INFORMATION: Synthetic Construct

<400> SEQUENCE: 26
gcgcgcatta tgaagaaaaa catcgctttt cttcttgcaa ttatgttcgt tttttctatt   60
gctacaaacg cttacgct   78

<210> SEQ ID NO 27
<211> LENGTH: 78
<212> TYPE: DNA
<213> ORGANISM: Artificial Sequence
<220> FEATURE:
<223> OTHER INFORMATION: Synthetic Construct

<400> SEQUENCE: 27
gcgcgcatta tgaagaaaaa catcgctttt cttcttgcat ctatgttcgt tttttctatt   60
gctacaaacg cttcggct   78

<210> SEQ ID NO 28
<211> LENGTH: 66
<212> TYPE: DNA
<213> ORGANISM: Artificial Sequence
<220> FEATURE:
<223> OTHER INFORMATION: Synthetic Construct

<400> SEQUENCE: 28
gcgcgcatta tgaaaaaaat ttggctcgcc ctggctggta ttgttttagc gtttagcgca   60
tcggcg   66

<210> SEQ ID NO 29
<211> LENGTH: 66
<212> TYPE: DNA
<213> ORGANISM: Artificial Sequence
<220> FEATURE:
<223> OTHER INFORMATION: Synthetic Construct

<400> SEQUENCE: 29
gcgcgcatta tgaaaaaaat ttggctcgcc ctggctggtt ctgttttagc gtttagcgca    60
tcggcg                                                              66

<210> SEQ ID NO 30
<211> LENGTH: 66
<212> TYPE: DNA
<213> ORGANISM: Artificial Sequence
<220> FEATURE:
<223> OTHER INFORMATION: Synthetic Construct

<400> SEQUENCE: 30
gcgcgcatta tgaaaaaaat ttggctcgcc ctggctggtt tagttttagc gtttagcgca    60
tacgcg                                                              66

<210> SEQ ID NO 31
<211> LENGTH: 23
<212> TYPE: PRT
<213> ORGANISM: Artificial Sequence
<220> FEATURE:
<223> OTHER INFORMATION: Synthetic Construct

<400> SEQUENCE: 31

Met Lys Lys Asn Ile Ala Phe Leu Leu Ala Ala Met Phe Val Phe Ser
1               5                   10                  15

Ile Ala Thr Asn Ala Tyr Ala
            20

<210> SEQ ID NO 32
<211> LENGTH: 23
<212> TYPE: PRT
<213> ORGANISM: Artificial Sequence
<220> FEATURE:
<223> OTHER INFORMATION: Synthetic Construct

<400> SEQUENCE: 32

Met Lys Lys Asn Ile Ala Phe Leu Leu Ala Gln Met Phe Val Phe Ser
1               5                   10                  15

Ile Ala Thr Asn Ala Tyr Ala
            20

<210> SEQ ID NO 33
<211> LENGTH: 23
<212> TYPE: PRT
<213> ORGANISM: Artificial Sequence
<220> FEATURE:
<223> OTHER INFORMATION: Synthetic Construct

<400> SEQUENCE: 33

Met Lys Lys Asn Ile Leu Phe Leu Leu Leu Met Phe Val Phe Ser
1               5                   10                  15

Ile Ala Thr Asn Ala Tyr Ala
            20

<210> SEQ ID NO 34
<211> LENGTH: 19
<212> TYPE: PRT

<213> ORGANISM: Artificial Sequence
<220> FEATURE:
<223> OTHER INFORMATION: Synthetic Construct

<400> SEQUENCE: 34

Met Lys Lys Ile Trp Leu Ala Leu Ala Gly Ala Val Leu Ala Phe Ser
1               5                   10                  15

Ala Ser Ala

<210> SEQ ID NO 35
<211> LENGTH: 19
<212> TYPE: PRT
<213> ORGANISM: Artificial Sequence
<220> FEATURE:
<223> OTHER INFORMATION: Synthetic Construct

<400> SEQUENCE: 35

Met Lys Lys Ile Trp Leu Ala Leu Ala Gly Gln Val Leu Ala Phe Ser
1               5                   10                  15

Ala Ser Ala

<210> SEQ ID NO 36
<211> LENGTH: 78
<212> TYPE: DNA
<213> ORGANISM: Artificial Sequence
<220> FEATURE:
<223> OTHER INFORMATION: Synthetic Construct

<400> SEQUENCE: 36
gcgcgcatta tgaagaaaaa catcgctttt cttcttgcag caatgttcgt tttttctatt    60
gctacaaacg cttacgct                                                  78

<210> SEQ ID NO 37
<211> LENGTH: 78
<212> TYPE: DNA
<213> ORGANISM: Artificial Sequence
<220> FEATURE:
<223> OTHER INFORMATION: Synthetic Construct

<400> SEQUENCE: 37
gcgcgcatta tgaagaaaaa catcgctttt cttcttgcac aaatgttcgt tttttctatt    60
gctacaaacg cttacgct                                                  78

<210> SEQ ID NO 38
<211> LENGTH: 78
<212> TYPE: DNA
<213> ORGANISM: Artificial Sequence
<220> FEATURE:
<223> OTHER INFORMATION: Synthetic Construct

<400> SEQUENCE: 38
gcgcgcatta tgaagaaaaa catcctcttt cttcttctac taatgttcgt tttttctatt    60
gctacaaacg cttacgct                                                  78

<210> SEQ ID NO 39
<211> LENGTH: 66
<212> TYPE: DNA
<213> ORGANISM: Artificial Sequence
<220> FEATURE:
<223> OTHER INFORMATION: Synthetic Construct

<400> SEQUENCE: 39
gcgcgcatta tgaaaaaaat tggctcgcc ctggctggtg ctgtttttagc gtttagcgca    60

```
tcggcg                                                              66

<210> SEQ ID NO 40
<211> LENGTH: 66
<212> TYPE: DNA
<213> ORGANISM: Artificial Sequence
<220> FEATURE:
<223> OTHER INFORMATION: Synthetic Construct

<400> SEQUENCE: 40
gcgcgcatta tgaaaaaaat ttggctcgcc ctggctggtc aggttttagc gtttagcgca    60
tcggcg                                                              66

<210> SEQ ID NO 41
<211> LENGTH: 23
<212> TYPE: PRT
<213> ORGANISM: Artificial Sequence
<220> FEATURE:
<223> OTHER INFORMATION: Synthetic Construct

<400> SEQUENCE: 41

Met Lys Lys Asn Ile Ala Phe Leu Leu Ala Tyr Met Phe Val Phe Ser
1               5                   10                  15

Ile Ala Thr Asn Ala Tyr Ala
            20

<210> SEQ ID NO 42
<211> LENGTH: 23
<212> TYPE: PRT
<213> ORGANISM: Artificial Sequence
<220> FEATURE:
<223> OTHER INFORMATION: Synthetic Construct

<400> SEQUENCE: 42

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 43
<211> LENGTH: 23
<212> TYPE: PRT
<213> ORGANISM: Artificial Sequence
<220> FEATURE:
<223> OTHER INFORMATION: Synthetic Construct

<400> SEQUENCE: 43

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 44
<211> LENGTH: 78
<212> TYPE: DNA
<213> ORGANISM: Artificial Sequence
<220> FEATURE:
<223> OTHER INFORMATION: Synthetic Construct

<400> SEQUENCE: 44
gcgcgcatta tgaagaaaaa catcgctttt cttcttgcat acatgttcgt tttttctatt    60
gctacaaacg cttacgct                                                 78
```

<210> SEQ ID NO 45
<211> LENGTH: 78
<212> TYPE: DNA
<213> ORGANISM: Artificial Sequence
<220> FEATURE:
<223> OTHER INFORMATION: Synthetic Construct

<400> SEQUENCE: 45
tctagaatta tgatgactaa aatcaagctt ctaatgctca ttatatttta tttaatcatt    60
tcggccagcg cccatgct                                                  78

<210> SEQ ID NO 46
<211> LENGTH: 78
<212> TYPE: DNA
<213> ORGANISM: Artificial Sequence
<220> FEATURE:
<223> OTHER INFORMATION: Synthetic Construct

<400> SEQUENCE: 46
tctagaatta tgatgacgaa aatcaagcta ctgatgctca ttatatttta tttaatcatt    60
tcggccagcg cccatgct                                                  78

<210> SEQ ID NO 47
<211> LENGTH: 19
<212> TYPE: PRT
<213> ORGANISM: Artificial Sequence
<220> FEATURE:
<223> OTHER INFORMATION: Synthetic Construct

<400> SEQUENCE: 47

Met Lys Lys Ile Trp Leu Ala Leu Ala Gly Leu Val Leu Ala Phe Ser
1               5                   10                  15

Ala Ser Ala

<210> SEQ ID NO 48
<211> LENGTH: 11
<212> TYPE: PRT
<213> ORGANISM: Artificial Sequence
<220> FEATURE:
<223> OTHER INFORMATION: Synthetic Construct

<400> SEQUENCE: 48

Asp Ile Cys Leu Pro Arg Trp Gly Cys Leu Trp
1               5                   10

<210> SEQ ID NO 49
<211> LENGTH: 19
<212> TYPE: PRT
<213> ORGANISM: Artificial Sequence
<220> FEATURE:
<223> OTHER INFORMATION: Synthetic Construct

<400> SEQUENCE: 49

Met Lys Lys Ile Trp Leu Ala Leu Ala Gly Ile Val Leu Ala Phe Ser
1               5                   10                  15

Ala Ser Ala

<210> SEQ ID NO 50
<211> LENGTH: 19
<212> TYPE: PRT
<213> ORGANISM: Artificial Sequence
<220> FEATURE:
<223> OTHER INFORMATION: Synthetic Construct

```
<400> SEQUENCE: 50

Met Lys Lys Ile Trp Leu Ala Leu Ala Gly Ser Val Leu Ala Phe Ser
1               5                   10                  15

Ala Ser Ala

<210> SEQ ID NO 51
<211> LENGTH: 23
<212> TYPE: PRT
<213> ORGANISM: Artificial Sequence
<220> FEATURE:
<223> OTHER INFORMATION: Synthetic Construct

<400> SEQUENCE: 51

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 52
<211> LENGTH: 23
<212> TYPE: PRT
<213> ORGANISM: Artificial Sequence
<220> FEATURE:
<223> OTHER INFORMATION: Synthetic Construct

<400> SEQUENCE: 52

Met Lys Lys Asn Ile Ala Phe Leu Leu Ala Leu Met Phe Val Phe Ser
1               5                   10                  15

Ile Ala Thr Asn Ala Tyr Ala
            20

<210> SEQ ID NO 53
<211> LENGTH: 23
<212> TYPE: PRT
<213> ORGANISM: Artificial Sequence
<220> FEATURE:
<223> OTHER INFORMATION: Synthetic Construct

<400> SEQUENCE: 53

Met Lys Lys Asn Ile Ala Phe Leu Leu Ala Ile Met Phe Val Phe Ser
1               5                   10                  15

Ile Ala Thr Asn Ala Tyr Ala
            20

<210> SEQ ID NO 54
<211> LENGTH: 19
<212> TYPE: PRT
<213> ORGANISM: Artificial Sequence
<220> FEATURE:
<223> OTHER INFORMATION: Synthetic Construct

<400> SEQUENCE: 54

Met Lys Lys Ile Trp Leu Ala Leu Ala Gly Leu Val Leu Ala Phe Ser
1               5                   10                  15

Ala Ser Ala

<210> SEQ ID NO 55
<211> LENGTH: 19
<212> TYPE: PRT
<213> ORGANISM: Artificial Sequence
<220> FEATURE:
<223> OTHER INFORMATION: Synthetic Construct

<400> SEQUENCE: 55
```

```
Met Lys Lys Ile Trp Leu Ala Leu Ala Gly Ala Val Leu Ala Phe Ser
1               5                   10                  15

Ala Ser Ala

<210> SEQ ID NO 56
<211> LENGTH: 19
<212> TYPE: PRT
<213> ORGANISM: Artificial Sequence
<220> FEATURE:
<223> OTHER INFORMATION: Synthetic Construct

<400> SEQUENCE: 56

Met Lys Lys Ile Trp Leu Ala Leu Ala Gly Gln Val Leu Ala Phe Ser
1               5                   10                  15

Ala Ser Ala

<210> SEQ ID NO 57
<211> LENGTH: 23
<212> TYPE: PRT
<213> ORGANISM: Artificial Sequence
<220> FEATURE:
<223> OTHER INFORMATION: Synthetic Construct

<400> SEQUENCE: 57

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic Construct

<400> SEQUENCE: 58

Met Lys Lys Asn Ile Ala Phe Leu Leu Ala Ala Met Phe Val Phe Ser
1               5                   10                  15

Ile Ala Thr Asn Ala Tyr Ala
            20

<210> SEQ ID NO 59
<211> LENGTH: 23
<212> TYPE: PRT
<213> ORGANISM: Artificial Sequence
<220> FEATURE:
<223> OTHER INFORMATION: Synthetic Construct

<400> SEQUENCE: 59

Met Lys Lys Asn Ile Ala Phe Leu Leu Ala Gln Met Phe Val Phe Ser
1               5                   10                  15

Ile Ala Thr Asn Ala Tyr Ala
            20

<210> SEQ ID NO 60
<211> LENGTH: 23
<212> TYPE: PRT
<213> ORGANISM: Artificial Sequence
<220> FEATURE:
<223> OTHER INFORMATION: Synthetic Construct

<400> SEQUENCE: 60
```

-continued

```
Met Lys Lys Asn Ile Ala Phe Leu Leu Ala Tyr Met Phe Val Phe Ser
1               5                   10                  15

Ile Ala Thr Asn Ala Tyr Ala
            20

<210> SEQ ID NO 61
<211> LENGTH: 23
<212> TYPE: PRT
<213> ORGANISM: Artificial Sequence
<220> FEATURE:
<223> OTHER INFORMATION: Synthetic Construct

<400> SEQUENCE: 61

Met Lys Lys Asn Ile Leu Phe Leu Leu Leu Leu Met Phe Val Phe Ser
1               5                   10                  15

Ile Ala Thr Asn Ala Tyr Ala
            20

<210> SEQ ID NO 62
<211> LENGTH: 23
<212> TYPE: PRT
<213> ORGANISM: Artificial Sequence
<220> FEATURE:
<223> OTHER INFORMATION: Synthetic Construct

<400> SEQUENCE: 62

Met Met Thr Lys Ile Lys Leu Leu Met Leu Ile Ile Phe Tyr Leu Ile
1               5                   10                  15

Ile Ser Ala Ser Ala His Ala
            20
```